US008067003B2

(12) United States Patent
Chen et al.

(10) Patent No.: US 8,067,003 B2
(45) Date of Patent: Nov. 29, 2011

(54) METHODS OF TREATING CONDITIONS USING ANTI-IL-6 ANTIBODIES

(75) Inventors: Yan Chen, Wayne, PA (US); Debra Gardner, Bear, DE (US); David M. Knight, Berwyn, PA (US); Michael W. Lark, Devon, PA (US); Bailin Liang, Gilbertsville, PA (US); David J. Shealy, Downingtown, PA (US); Xiao-Yu R. Song, West Chester, PA (US); Vedrana Stojanovic-Susulic, Princeton Junction, NJ (US); Raymond W. Sweet, Bryn Mawr, PA (US); Susan H. Tam, Boothwyn, PA (US); Sheng-Jiun Wu, Broomall, PA (US); Jing Yang, Ambler, PA (US); David Matthew Marquis, Encinitas, CA (US); Eric Michael Smith, San Diego, CA (US); Alain Philippe Vasserot, Carlsbad, CA (US)

(73) Assignees: Centocor, Inc., Malvern, PA (US); Applied Molecular Evolution, Inc., San Diego, CA (US)

( * ) Notice: Subject to any disclaimer, the term of this patent is extended or adjusted under 35 U.S.C. 154(b) by 0 days.

(21) Appl. No.: 12/901,200

(22) Filed: Oct. 8, 2010

(65) Prior Publication Data

US 2011/0081355 A1 Apr. 7, 2011

Related U.S. Application Data

(62) Division of application No. 12/470,753, filed on May 22, 2009, now Pat. No. 7,833,755.

(51) Int. Cl.
*A61K 39/395* (2006.01)
(52) U.S. Cl. ............... 424/145.1; 424/130.1; 424/141.1
(58) Field of Classification Search ........................ None
See application file for complete search history.

(56) References Cited

U.S. PATENT DOCUMENTS

| | | | |
|---|---|---|---|
| 5,001,116 A | 3/1991 | Folkman et al. |
| 5,210,075 A | 5/1993 | Scholz et al. |
| 5,326,859 A | 7/1994 | Sugano et al. |
| 5,468,609 A | 11/1995 | Revel et al. |
| 5,530,101 A | 6/1996 | Queen et al. |
| 5,554,513 A | 9/1996 | Revel et al. |
| 5,559,012 A | 9/1996 | Brailly et al. |
| 5,591,827 A | 1/1997 | Brakenhoff et al. |
| 5,618,700 A | 4/1997 | Novick et al. |
| 5,618,920 A | 4/1997 | Robinson et al. |
| 5,639,455 A | 6/1997 | Shimanura et al. |
| 5,723,120 A | 3/1998 | Brakenhoff et al. |
| 5,738,931 A | 4/1998 | Sato et al. |
| 5,789,552 A | 8/1998 | Savino et al. |
| 5,807,715 A | 9/1998 | Morrison et al. |
| 5,817,790 A | 10/1998 | Tsuchiya et al. |
| 5,849,283 A | 12/1998 | Ciliberto |
| 5,854,398 A | 12/1998 | Chang et al. |
| 5,856,135 A | 1/1999 | Tsuchiya et al. |
| 5,871,723 A | 2/1999 | Strieter et al. |
| 5,888,510 A | 3/1999 | Kishimoto et al. |
| 5,888,511 A | 3/1999 | Skurkovich et al. |
| 5,914,106 A | 6/1999 | Ciliberto |
| 5,942,220 A | 8/1999 | Warren et al. |
| 5,958,400 A | 9/1999 | Ruben et al. |
| 5,972,902 A | 10/1999 | Ciliberto |
| 6,010,864 A | 1/2000 | Hoeprich, Jr. |
| 6,086,874 A | 7/2000 | Yoshida et al. |
| 6,121,423 A | 9/2000 | Tsuchiya et al. |
| 6,261,560 B1 | 7/2001 | Tsujinake et al. |
| 6,461,604 B1 | 10/2002 | Somers et al. |
| 6,482,411 B1 | 11/2002 | Ahuja et al. |
| 7,291,721 B2 | 11/2007 | Giles-Komar et al. |
| 2001/0001663 A1 | 5/2001 | Kishimoto et al. |
| 2003/0190316 A1 | 10/2003 | Kakuta et al. |
| 2004/0028681 A1 | 2/2004 | Ito et al. |

FOREIGN PATENT DOCUMENTS

| | | |
|---|---|---|
| EP | 0399429 A1 | 11/1990 |
| EP | 0572118 B1 | 4/1993 |
| EP | 0617126 B1 | 9/1994 |
| EP | 800829 B1 | 10/1997 |
| WO | WO 91/08774 A1 | 6/1991 |
| WO | WO 94/09138 A1 | 4/1994 |
| WO | WO 95/03036 A1 | 2/1995 |
| WO | WO 01/58956 A2 | 8/2001 |
| WO | WO 03/083061 A2 | 10/2003 |
| WO | WO 2004/039826 A1 | 5/2004 |
| WO | WO 2004/096273 A1 | 11/2004 |
| WO | WO 2005/005604 A2 | 1/2005 |
| WO | WO 2005/028514 A1 | 3/2005 |

OTHER PUBLICATIONS

Brakenhoff, et al., "Structure-Function Analysis of Human IL-6 Epitope Mapping of Neutralizing Monoclonal Antibodies with Amino- and Carboxyl-Terminal Deletion Mutants," The Journal of Immunology, 145(2): 561-568 (1990).
Brakenhoff, et al., "Molecular Cloning and Expression of Hybridoma Growth Factor in *Escherichia coli*," The Journal of Immunology, 139(12): 4116-4121 (1987). Van Zaanen, et al., Blocking Interleukin-6 Activity with Chimeric Anti-IL6 Monoclonal Antibodies in Multiple Myeloma: Effects on Soluble IL6 Receptor and Soluble gp130, Leukemia & Lymphoma, 31 (5-6): 551-558 (1998).
Van Zaanen, et al., Endogenous Interleukin 6 Production in Multiple Myeloma Patients Treated with Chimeric Monoclonal Anti-IL6 Antibodies Indicates the Existence of a Positive Feed-back Loop, Journal of Clinical Investigations, The American Society for Clinical Investigation, Inc., 98(6): 1441-1448 (1996).
Van Oers, Chimaeric anti-interleukin 6 monoclonal antibodies in the treatment of advanced multiple myeloma: a Phase I dose-escalating study, British Journal of Haematology, 102(3): 783-790 (1998).
Baselga, et al., "Receptor Blockage with Monoclonal Antibodies as Anti-Cancer Therapy," Pharmaceutical Therapy, 64: 127-154 (1994).
Matsuda, et al., "Establishment of an interleukin 6 (IL6)/B cell stimulatory factor 2-dependent cell line and preparation of anti-IL6 monoclonal antibodies," European Journal of Immunology, 18: 951-956 (1988).

(Continued)

*Primary Examiner* — Prema Mertz
(74) *Attorney, Agent, or Firm* — Eric Dichter

(57) ABSTRACT

Anti-IL-6 antibodies are used to treat IL-6 related conditions, such as rheumatoid arthritis, osteoarthritis, osteolysis, aseptic loosening of orthopedic implants, systemic lupus erythematosus, cutaneous lupus erythematosus, lupus nephritis, type 2 diabetes mellitus, chronic obstructive pulmonary disease, and renal cell carcinoma.

12 Claims, 18 Drawing Sheets

OTHER PUBLICATIONS

Seideman, et al., "A novel monoclonal antibody screening method using the Luminex-100 microsphere system," Journal of Immunology Methods, 267: 165-171 (2002).

Bataille, et al., Biologica Effects of Anti-Interleukin-6 Murine Monoclonal Antibody in Advanced Multiple Myeloma, Blood, 86(2): 685-691 (1995).

Trikha, et al., "Targeted Anti-Interleukin-6 Monoclonal Antibody Therapy for Cancer: A Review of the Rationale and Clinical Evidence," Clinical Cancer Res., 9: 4653-4665 (2003).

Sato, et al., "Humanization of an Anti-Human IL-6 Mouse Monoclonal Antibody Glycosylated in its Heavy Chain Variable Region," Human Antibodies and Hybridomas, 7(4): 175-183 (1996).

Naka, et al., "The Paradigm of IL-6: From Basic Science to Medicine," Arthritis Research, Current Science, 4(3): S233-S242 (2002).

Petrov, "Immunology," Medicine Publishers, 56-58 (1987), Russian Article and English translation.

Paul, "Fv Structure and Diversity in Three Dimensions," Fundamental Immunology, 3$^{rd}$ edition pp. 292-295 (1993).

Rudikoff, et al., "Single amino acid substitution altering antigen-binding specificity," Proceedings of the National Academy of Science, USA 79: 1979-1783 (1982).

Cruse and Lewis, Illustrated Dictionary of Immunology, p. 19 (1995).

Aoki, et al., "Angiogenesis and Hematopoiesis Induced by Kaposi's Sarcoma-Associated Herpesvirus-Encoded Interleukin-6," Blood, 93(12): 4034-4043 (1999).

Pourtau, et al., "Cyclooxygenase-2 activity is necessary for the angiogenic properties of oncostatin M," FEBS Letters, 459: 453-457 (1999).

Wei, et al., "Interleukin-6 promotes cervical tumor growth by VEGF-dependent angiogenesis via a STAT3 pathway," Oncogene, 22:1517-1527 (2003).

Motro, et al., "Pattern of interleukin 6 gene expression in vivo suggests a role for this cytokine in angiogenesis," Proceedings of the National Academy of Science USA, 87: 3092-3096 (1990).

Cohen, et al., "Interleukin 6 Induces the Expression of Vascular Endothelial Growth Factor," The Journal of Biological Chemistry, 271(2): 736-741 (1996).

Chauhan, et al., "SHP2 Mediates the Protective Effect of Interleukin-6 against Dexamethasone-induced Apoptosis in Multiple Myeloma Cells," The Journal of Biological Chemistry, 275(36): 27845-27850 (2000).

Blay, et al., "Serum Level of Interleukin 6 as a Prognosis Factor in Metastic Renal Cell Carcinoma," Cancer Research, 52: 3317-3322 (1992).

Miki, et al., "Interleukin-6 (IL-6) functions as an in vitro autocrine growth factor in renal cell carcinomas," FEBS Letters, 250(2): 607-610 (1989).

Vink, et al., Mouse Plasmacytoma Growth in Vivo: Enhancement by Interleukin 6 (IL-6) and Inhibition by Antibodies Directed against IL-6 or Its Receptor, Journal of Experimental Medicine, 172: 997-1000 (1990).

Sato, et al., "Reshaping a Human Antibody to Inhibit the Interleukin 6-dependent Tumor Cell Growth," Cancer Research, 53: 851-856 (1993).

Shimamura, et al., "Analysis of Interleukin-6 (IL-6)/IL-6 Receptor System Using Monoclonal Anti-IL-6 Antibodies," Molecular Immunology, 28(11): 1155-1161 (1991).

US 6,008,005, 12/1999, Shiraki et al. (withdrawn)

$_{168}$RSFKEFLQSSLRALRQM$_{184}$

FIG. 5A
FIG. 5B
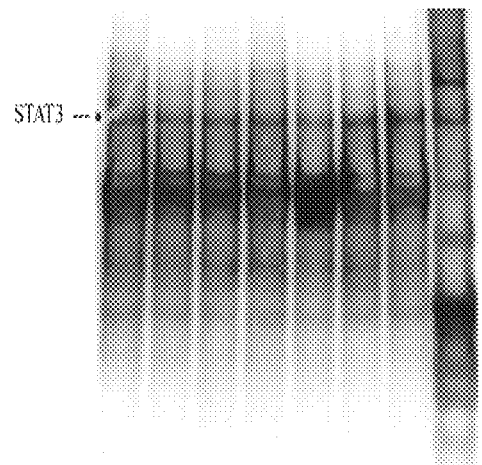
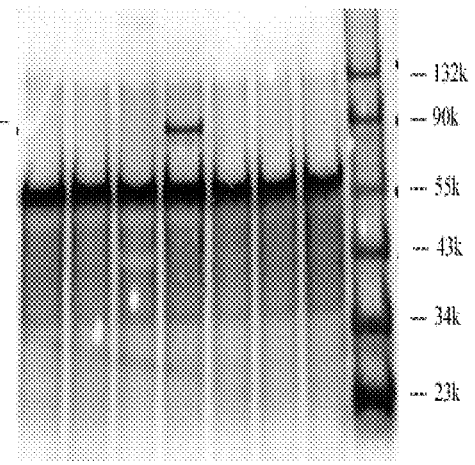

IP: IRS1
IB: p85

← p85

IP: IRS1
IB: IRS1

← IRS-1

| | |
|---|---|
| 1 | control |
| 2 | insulin |
| 3 | insulin + IL6 |
| 4 | insulin + IL6 + IL6 mAb |
| 5 | insulin + IL6 mAb |
| 6 | IL6 |
| 7 | IL6 mAb |

SEQUENCE LISTING

<160> NUMBER OF SEQ ID NOS: 138

<210> SEQ ID NO 1
<211> LENGTH: 10
<212> TYPE: PRT
<213> ORGANISM: Homo sapiens

<400> SEQUENCE: 1

Ser Ala Ser His Ser Val Ser Tyr Met Tyr
 1               5                  10

<210> SEQ ID NO 2
<211> LENGTH: 30
<212> TYPE: DNA
<213> ORGANISM: Homo sapiens

<400> SEQUENCE: 2
agtgccagcc atagtgtaag ttacatgtac                                    30

<210> SEQ ID NO 3
<211> LENGTH: 10
<212> TYPE: PRT
<213> ORGANISM: Homo sapiens

<400> SEQUENCE: 3

Ser Ala Ser Ile Ser Val Ser Tyr Met Tyr
 1               5                  10

<210> SEQ ID NO 4
<211> LENGTH: 30
<212> TYPE: DNA
<213> ORGANISM: Homo sapiens

<400> SEQUENCE: 4
agtgccagca ttagtgtaag ttacatgtac                                    30

<210> SEQ ID NO 5
<211> LENGTH: 10
<212> TYPE: PRT
<213> ORGANISM: Homo sapiens

<400> SEQUENCE: 5

Ser Ala Arg Ser Ser Val Ser Tyr Met Tyr
 1               5                  10

<210> SEQ ID NO 6
<211> LENGTH: 30
<212> TYPE: DNA
<213> ORGANISM: Homo sapiens

<400> SEQUENCE: 6
agtgcccggt caagtgtaag ttacatgtac                                    30

<210> SEQ ID NO 7
<211> LENGTH: 10
<212> TYPE: PRT
<213> ORGANISM: Homo sapiens

<400> SEQUENCE: 7

Ser Ala Ser Tyr Ser Val Ser Tyr Met Tyr
 1               5                  10

<210> SEQ ID NO 8

```
<211> LENGTH: 30
<212> TYPE: DNA
<213> ORGANISM: Homo sapiens

<400> SEQUENCE: 8
agtgccagct atagtgtaag ttacatgtac                                              30

<210> SEQ ID NO 9
<211> LENGTH: 10
<212> TYPE: PRT
<213> ORGANISM: Homo sapiens

<400> SEQUENCE: 9

Ser Ala Ser Ser Ser Val Phe Tyr Met Tyr
1               5                   10

<210> SEQ ID NO 10
<211> LENGTH: 30
<212> TYPE: DNA
<213> ORGANISM: Homo sapiens

<400> SEQUENCE: 10
agtgccagct caagtgtatt ttacatgtac                                              30

<210> SEQ ID NO 11
<211> LENGTH: 10
<212> TYPE: PRT
<213> ORGANISM: Homo sapiens

<400> SEQUENCE: 11

Ser Gly Ser Ser Tyr Val Ser Tyr Met Tyr
1               5                   10

<210> SEQ ID NO 12
<211> LENGTH: 30
<212> TYPE: DNA
<213> ORGANISM: Homo sapiens

<400> SEQUENCE: 12
agtggcagct catatgtaag ttacatgtac                                              30

<210> SEQ ID NO 13
<211> LENGTH: 10
<212> TYPE: PRT
<213> ORGANISM: Homo sapiens

<400> SEQUENCE: 13

Ser Ala Leu Ser Ser Val Ser Tyr Met Tyr
1               5                   10

<210> SEQ ID NO 14
<211> LENGTH: 30
<212> TYPE: DNA
<213> ORGANISM: Homo sapiens

<400> SEQUENCE: 14
agtgccctgt caagtgtaag ttacatgtac                                              30

<210> SEQ ID NO 15
<211> LENGTH: 10
<212> TYPE: PRT
<213> ORGANISM: Homo sapiens

<400> SEQUENCE: 15

Ser Ala Ser Ser Ser Val Ser Tyr Met Tyr
```

```
<210> SEQ ID NO 16
<211> LENGTH: 30
<212> TYPE: DNA
<213> ORGANISM: Homo sapiens

<400> SEQUENCE: 16
agtgccagct caagtgtaag ttacatgtac                                    30

<210> SEQ ID NO 17
<211> LENGTH: 7
<212> TYPE: PRT
<213> ORGANISM: Homo sapiens

<400> SEQUENCE: 17

Asp Phe Ser Asn Leu Ala Ser
 1               5

<210> SEQ ID NO 18
<211> LENGTH: 21
<212> TYPE: DNA
<213> ORGANISM: Homo sapiens

<400> SEQUENCE: 18
gactttccca acctggcttc t                                             21

<210> SEQ ID NO 19
<211> LENGTH: 7
<212> TYPE: PRT
<213> ORGANISM: Homo sapiens

<400> SEQUENCE: 19

Asp Leu Ser Asn Leu Ala Ser
 1               5

<210> SEQ ID NO 20
<211> LENGTH: 21
<212> TYPE: DNA
<213> ORGANISM: Homo sapiens

<400> SEQUENCE: 20
gacctgtcca acctggcttc t                                             21

<210> SEQ ID NO 21
<211> LENGTH: 7
<212> TYPE: PRT
<213> ORGANISM: Homo sapiens

<400> SEQUENCE: 21

Asp Met Ser Asn Leu Ala Ser
 1               5

<210> SEQ ID NO 22
<211> LENGTH: 21
<212> TYPE: DNA
<213> ORGANISM: Homo sapiens

<400> SEQUENCE: 22
gacatgtcca acctggcttc t                                             21

<210> SEQ ID NO 23
<211> LENGTH: 7
<212> TYPE: PRT
<213> ORGANISM: Homo sapiens
```

```
<400> SEQUENCE: 23

Asp Thr Ser Asn Leu Thr Ser
  1               5

<210> SEQ ID NO 24
<211> LENGTH: 21
<212> TYPE: DNA
<213> ORGANISM: Homo sapiens

<400> SEQUENCE: 24
gacacatcca acctgacgtc t                                       21

<210> SEQ ID NO 25
<211> LENGTH: 7
<212> TYPE: PRT
<213> ORGANISM: Homo sapiens

<400> SEQUENCE: 25

Asp Thr Ser Glu Leu Ala Ser
  1               5

<210> SEQ ID NO 26
<211> LENGTH: 21
<212> TYPE: DNA
<213> ORGANISM: Homo sapiens

<400> SEQUENCE: 26
gacacatccg agctggcttc t                                       21

<210> SEQ ID NO 27
<211> LENGTH: 7
<212> TYPE: PRT
<213> ORGANISM: Homo sapiens

<400> SEQUENCE: 27

Asp Thr Ser Asn Leu Ala Ser
  1               5

<210> SEQ ID NO 28
<211> LENGTH: 21
<212> TYPE: DNA
<213> ORGANISM: Homo sapiens

<400> SEQUENCE: 28
gacacatcca acctggcttc t                                       21

<210> SEQ ID NO 29
<211> LENGTH: 9
<212> TYPE: PRT
<213> ORGANISM: Homo sapiens

<400> SEQUENCE: 29

Met Gln Trp Ser Gly Tyr Pro Tyr Thr
  1               5

<210> SEQ ID NO 30
<211> LENGTH: 27
<212> TYPE: DNA
<213> ORGANISM: Homo sapiens

<400> SEQUENCE: 30
atgcagtgga gtggttaccc atacacg                                 27
```

```
<210> SEQ ID NO 31
<211> LENGTH: 9
<212> TYPE: PRT
<213> ORGANISM: Homo sapiens

<400> SEQUENCE: 31

Cys Gln Trp Ser Gly Tyr Pro Tyr Thr
 1               5

<210> SEQ ID NO 32
<211> LENGTH: 27
<212> TYPE: DNA
<213> ORGANISM: Homo sapiens

<400> SEQUENCE: 32
tgtcagtgga gtggttaccc atacacg                                       27

<210> SEQ ID NO 33
<211> LENGTH: 9
<212> TYPE: PRT
<213> ORGANISM: Homo sapiens

<400> SEQUENCE: 33

Ser Cys Trp Ser Gly Tyr Pro Tyr Thr
 1               5

<210> SEQ ID NO 34
<211> LENGTH: 27
<212> TYPE: DNA
<213> ORGANISM: Homo sapiens

<400> SEQUENCE: 34
tctgtgtgga gtggttaccc atacacg                                       27

<210> SEQ ID NO 35
<211> LENGTH: 9
<212> TYPE: PRT
<213> ORGANISM: Homo sapiens

<400> SEQUENCE: 35

Ser Gln Trp Ser Gly Tyr Pro Tyr Thr
 1               5

<210> SEQ ID NO 36
<211> LENGTH: 27
<212> TYPE: DNA
<213> ORGANISM: Homo sapiens

<400> SEQUENCE: 36
tctcagtgga gtggttaccc atacacg                                       27

<210> SEQ ID NO 37
<211> LENGTH: 10
<212> TYPE: PRT
<213> ORGANISM: Homo sapiens

<400> SEQUENCE: 37

Gly Phe Thr Phe Ser Ser Phe Ala Leu Ser
 1               5                  10

<210> SEQ ID NO 38
<211> LENGTH: 30
<212> TYPE: DNA
<213> ORGANISM: Homo sapiens

<400> SEQUENCE: 38
```

```
ggattcacct ttagtagctt tgccctttct                                30
```

<210> SEQ ID NO 39
<211> LENGTH: 10
<212> TYPE: PRT
<213> ORGANISM: Homo sapiens

<400> SEQUENCE: 39

Gly Phe Thr Phe Ser Pro Phe Ala Met Ser
 1               5                  10

<210> SEQ ID NO 40
<211> LENGTH: 30
<212> TYPE: DNA
<213> ORGANISM: Homo sapiens

<400> SEQUENCE: 40

```
ggattcacct ttagtccttt tgccatgtct                                30
```

<210> SEQ ID NO 41
<211> LENGTH: 10
<212> TYPE: PRT
<213> ORGANISM: Homo sapiens

<400> SEQUENCE: 41

Gly Phe Gln Phe Ser Ser Phe Ala Met Ser
 1               5                  10

<210> SEQ ID NO 42
<211> LENGTH: 30
<212> TYPE: DNA
<213> ORGANISM: Homo sapiens

<400> SEQUENCE: 42

```
ggattccagt ttagtagctt tgccatgtct                                30
```

<210> SEQ ID NO 43
<211> LENGTH: 10
<212> TYPE: PRT
<213> ORGANISM: Homo sapiens

<400> SEQUENCE: 43

Gly Phe Thr Thr Ser Ser Phe Ala Met Ser
 1               5                  10

<210> SEQ ID NO 44
<211> LENGTH: 30
<212> TYPE: DNA
<213> ORGANISM: Homo sapiens

<400> SEQUENCE: 44

```
ggattcacca ctagtagctt tgccatgtct                                30
```

<210> SEQ ID NO 45
<211> LENGTH: 10
<212> TYPE: PRT
<213> ORGANISM: Homo sapiens

<400> SEQUENCE: 45

Gly Phe Gln Phe Ser Pro Phe Ala Met Ser
 1               5                  10

<210> SEQ ID NO 46
<211> LENGTH: 30

```
<212> TYPE: DNA
<213> ORGANISM: Homo sapiens

<400> SEQUENCE: 46
ggattccagt ttagtccttt tgccatgtct                                   30

<210> SEQ ID NO 47
<211> LENGTH: 10
<212> TYPE: PRT
<213> ORGANISM: Homo sapiens

<400> SEQUENCE: 47

Gly Phe Thr Phe Ser Ser Phe Ala Met Ser
1               5                   10

<210> SEQ ID NO 48
<211> LENGTH: 30
<212> TYPE: DNA
<213> ORGANISM: Homo sapiens

<400> SEQUENCE: 48
ggattcacct ttagtagctt tgccatgtct                                   30

<210> SEQ ID NO 49
<211> LENGTH: 17
<212> TYPE: PRT
<213> ORGANISM: Homo sapiens

<400> SEQUENCE: 49

Lys Ala Ser Ser Gly Gly Ser Tyr Thr Tyr Tyr Pro Asp Thr Val Thr
1               5                   10                  15

Gly

<210> SEQ ID NO 50
<211> LENGTH: 51
<212> TYPE: DNA
<213> ORGANISM: Homo sapiens

<400> SEQUENCE: 50
aaagcgagta gtggtgggag ttacacctac tatcctgaca ctgtgacggg c           51

<210> SEQ ID NO 51
<211> LENGTH: 17
<212> TYPE: PRT
<213> ORGANISM: Homo sapiens

<400> SEQUENCE: 51

Lys Ile Ser Ser Gly Gly Ser Tyr Glu Tyr Tyr Pro Asp Thr Val Thr
1               5                   10                  15

Gly

<210> SEQ ID NO 52
<211> LENGTH: 51
<212> TYPE: DNA
<213> ORGANISM: Homo sapiens

<400> SEQUENCE: 52
aaaattagta gtggtgggag ttacgagtac tatcctgaca ctgtgacggg c           51

<210> SEQ ID NO 53
<211> LENGTH: 17
<212> TYPE: PRT
<213> ORGANISM: Homo sapiens
```

<400> SEQUENCE: 53

Lys Ile Ser Ser Gly Gly Ser Tyr Tyr Tyr Pro Asp Thr Val Thr
1               5                   10                  15

Gly

<210> SEQ ID NO 54
<211> LENGTH: 51
<212> TYPE: DNA
<213> ORGANISM: Homo sapiens

<400> SEQUENCE: 54
aaaattagta gtggtgggag ttactattac tatcctgaca ctgtgacggg c        51

<210> SEQ ID NO 55
<211> LENGTH: 17
<212> TYPE: PRT
<213> ORGANISM: Homo sapiens

<400> SEQUENCE: 55

Lys Ile Ser Ser Gly Gly Ser Trp Thr Tyr Tyr Pro Asp Thr Val Thr
1               5                   10                  15

Gly

<210> SEQ ID NO 56
<211> LENGTH: 51
<212> TYPE: DNA
<213> ORGANISM: Homo sapiens

<400> SEQUENCE: 56
aaaattagta gtggtgggag ttggacctac tatcctgaca ctgtgacggg c        51

<210> SEQ ID NO 57
<211> LENGTH: 17
<212> TYPE: PRT
<213> ORGANISM: Homo sapiens

<400> SEQUENCE: 57

Lys Ile Ser Pro Gly Gly Ser Tyr Thr Tyr Tyr Pro Asp Thr Val Thr
1               5                   10                  15

Gly

<210> SEQ ID NO 58
<211> LENGTH: 51
<212> TYPE: DNA
<213> ORGANISM: Homo sapiens

<400> SEQUENCE: 58
aaaattagtc cgggtgggag ttacacctac tatcctgaca ctgtgacggg c        51

<210> SEQ ID NO 59
<211> LENGTH: 17
<212> TYPE: PRT
<213> ORGANISM: Homo sapiens

<400> SEQUENCE: 59

Lys Ile Ser Pro Gly Gly Ser Trp Thr Tyr Tyr Ser Asp Thr Val Thr
1               5                   10                  15

Gly

<210> SEQ ID NO 60
<211> LENGTH: 51
<212> TYPE: DNA

<213> ORGANISM: Homo sapiens

<400> SEQUENCE: 60
aaaattagtc cgggtgggag ttggacctac tattctgaca ctgtgacggg c    51

<210> SEQ ID NO 61
<211> LENGTH: 17
<212> TYPE: PRT
<213> ORGANISM: Homo sapiens

<400> SEQUENCE: 61

Lys Ile Ser Ser Gly Gly Ser Tyr Thr Tyr Tyr Pro Asp Thr Val Thr
 1               5                  10                  15
Gly

<210> SEQ ID NO 62
<211> LENGTH: 51
<212> TYPE: DNA
<213> ORGANISM: Homo sapiens

<400> SEQUENCE: 62
aaaattagta gtggtgggag ttacacctac tatcctgaca ctgtgacggg c    51

<210> SEQ ID NO 63
<211> LENGTH: 17
<212> TYPE: PRT
<213> ORGANISM: Homo sapiens

<400> SEQUENCE: 63

Lys Ile Ser Ser Gly Gly Ser Tyr Thr Tyr Phe Pro Asp Thr Val Thr
 1               5                  10                  15
Gly

<210> SEQ ID NO 64
<211> LENGTH: 51
<212> TYPE: DNA
<213> ORGANISM: Homo sapiens

<400> SEQUENCE: 64
aaaattagta gtggtgggag ttacacctac tttcctgaca ctgtgacggg c    51

<210> SEQ ID NO 65
<211> LENGTH: 17
<212> TYPE: PRT
<213> ORGANISM: Homo sapiens

<400> SEQUENCE: 65

Lys Ile Ser Ser Gly Gly Ser Tyr Thr Tyr Tyr Pro Asp Thr Val Ala
 1               5                  10                  15
Gly

<210> SEQ ID NO 66
<211> LENGTH: 51
<212> TYPE: DNA
<213> ORGANISM: Homo sapiens

<400> SEQUENCE: 66
aaaattagta gtggtgggag ttacacctac tatcctgaca ctgtggctgg c    51

<210> SEQ ID NO 67
<211> LENGTH: 17
<212> TYPE: PRT

<400> SEQUENCE: 67

Lys Ile Ser Ser Gly Gly Ser Tyr Thr Tyr Tyr Asp Asp Thr Val Thr
1               5                   10                  15

Gly

<210> SEQ ID NO 68
<211> LENGTH: 51
<212> TYPE: DNA
<213> ORGANISM: Homo sapiens

<400> SEQUENCE: 68
aaaattagta gtggtgggag ttacacctac tatgatgaca ctgtgacggg c          51

<210> SEQ ID NO 69
<211> LENGTH: 17
<212> TYPE: PRT
<213> ORGANISM: Homo sapiens

<400> SEQUENCE: 69

Lys Ile Ser Ser Gly Gly Ser Tyr Thr Tyr Tyr Ser Asp Thr Val Thr
1               5                   10                  15

Gly

<210> SEQ ID NO 70
<211> LENGTH: 51
<212> TYPE: DNA
<213> ORGANISM: Homo sapiens

<400> SEQUENCE: 70
aaaattagta gtggtgggag ttacacctac tattctgaca ctgtgacggg c          51

<210> SEQ ID NO 71
<211> LENGTH: 17
<212> TYPE: PRT
<213> ORGANISM: Homo sapiens

<400> SEQUENCE: 71

Lys Ile Ser Ser Gly Gly Ser Tyr Thr Tyr Tyr Pro Asp Thr Val Thr
1               5                   10                  15

Pro

<210> SEQ ID NO 72
<211> LENGTH: 51
<212> TYPE: DNA
<213> ORGANISM: Homo sapiens

<400> SEQUENCE: 72
aaaattagta gtggtgggag ttacacctac tatcctgaca ctgtgacgcc g          51

<210> SEQ ID NO 73
<211> LENGTH: 17
<212> TYPE: PRT
<213> ORGANISM: Homo sapiens

<400> SEQUENCE: 73

Lys Ile Ser Ser Gly Gly Ser Tyr Thr Tyr Tyr Pro Asp Thr Asp Thr
1               5                   10                  15

Gly

<210> SEQ ID NO 74
<211> LENGTH: 51

-continued

```
<212> TYPE: DNA
<213> ORGANISM: Homo sapiens

<400> SEQUENCE: 74
aaaattagta gtggtgggag ttacacctac tatcctgaca ctgatacggg c         51

<210> SEQ ID NO 75
<211> LENGTH: 17
<212> TYPE: PRT
<213> ORGANISM: Homo sapiens

<400> SEQUENCE: 75

Lys Ile Ser Pro Gly Gly Ser Tyr Thr Tyr Tyr Ser Asp Thr Val Thr
1               5                   10                  15

Gly

<210> SEQ ID NO 76
<211> LENGTH: 51
<212> TYPE: DNA
<213> ORGANISM: Homo sapiens

<400> SEQUENCE: 76
aaaattagtc cgggtgggag ttacacctac tattctgaca ctgtgacggg c         51

<210> SEQ ID NO 77
<211> LENGTH: 17
<212> TYPE: PRT
<213> ORGANISM: Homo sapiens

<400> SEQUENCE: 77

Lys Ile Ser Pro Gly Gly Ser Trp Thr Tyr Tyr Asp Asp Thr Val Thr
1               5                   10                  15

Gly

<210> SEQ ID NO 78
<211> LENGTH: 51
<212> TYPE: DNA
<213> ORGANISM: Homo sapiens

<400> SEQUENCE: 78
aaaattagtc cgggtgggag ttggacctac tatgatgaca ctgtgacggg c         51

<210> SEQ ID NO 79
<211> LENGTH: 10
<212> TYPE: PRT
<213> ORGANISM: Homo sapiens

<400> SEQUENCE: 79

Gln Leu Trp Gly Ser Tyr Ala Leu Asp Tyr
1               5                   10

<210> SEQ ID NO 80
<211> LENGTH: 30
<212> TYPE: DNA
<213> ORGANISM: Homo sapiens

<400> SEQUENCE: 80
cagttatggg ggtcgtatgc tcttgactac                                 30

<210> SEQ ID NO 81
<211> LENGTH: 10
<212> TYPE: PRT
<213> ORGANISM: Homo sapiens
```

```
<400> SEQUENCE: 81

Gln Leu Trp Gly Tyr Tyr Ala Leu Asp Thr
 1               5                  10

<210> SEQ ID NO 82
<211> LENGTH: 30
<212> TYPE: DNA
<213> ORGANISM: Homo sapiens

<400> SEQUENCE: 82
cagttatggg ggtactatgc tcttgacacg                              30

<210> SEQ ID NO 83
<211> LENGTH: 10
<212> TYPE: PRT
<213> ORGANISM: Homo sapiens

<400> SEQUENCE: 83

Gln Leu Trp Gly Thr Tyr Ala Leu Asp Tyr
 1               5                  10

<210> SEQ ID NO 84
<211> LENGTH: 30
<212> TYPE: DNA
<213> ORGANISM: Homo sapiens

<400> SEQUENCE: 84
cagttatggg ggacttatgc tcttgactac                              30

<210> SEQ ID NO 85
<211> LENGTH: 10
<212> TYPE: PRT
<213> ORGANISM: Homo sapiens

<400> SEQUENCE: 85

Gln Leu Trp Gly Asn Tyr Ala Leu Asp Tyr
 1               5                  10

<210> SEQ ID NO 86
<211> LENGTH: 30
<212> TYPE: DNA
<213> ORGANISM: Homo sapiens

<400> SEQUENCE: 86
cagttatggg ggaattatgc tcttgactac                              30

<210> SEQ ID NO 87
<211> LENGTH: 10
<212> TYPE: PRT
<213> ORGANISM: Homo sapiens

<400> SEQUENCE: 87

Gln Leu Trp Gly Tyr Tyr Ala Leu Asp Phe
 1               5                  10

<210> SEQ ID NO 88
<211> LENGTH: 30
<212> TYPE: DNA
<213> ORGANISM: Homo sapiens

<400> SEQUENCE: 88
cagttatggg ggtactatgc tcttgactttt                             30

<210> SEQ ID NO 89
```

```
<211> LENGTH: 10
<212> TYPE: PRT
<213> ORGANISM: Homo sapiens

<400> SEQUENCE: 89

Gln Leu Trp Gly Tyr Tyr Ala Leu Asp Ile
1               5                   10

<210> SEQ ID NO 90
<211> LENGTH: 30
<212> TYPE: DNA
<213> ORGANISM: Homo sapiens

<400> SEQUENCE: 90
cagttatggg ggtactatgc tcttgacatt                                    30

<210> SEQ ID NO 91
<211> LENGTH: 10
<212> TYPE: PRT
<213> ORGANISM: Homo sapiens

<400> SEQUENCE: 91

Gln Leu Trp Gly Tyr Tyr Ala Leu Asp Tyr
1               5                   10

<210> SEQ ID NO 92
<211> LENGTH: 30
<212> TYPE: DNA
<213> ORGANISM: Homo sapiens

<400> SEQUENCE: 92
cagttatggg ggtactatgc tcttgactac                                    30

<210> SEQ ID NO 93
<211> LENGTH: 106
<212> TYPE: PRT
<213> ORGANISM: Homo sapiens

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Ser Gln Trp Ser Gly Tyr Pro Tyr Thr
                85                  90                  95

Phe Gly Gly Gly Thr Lys Val Glu Ile Lys
            100                 105

<210> SEQ ID NO 94
<211> LENGTH: 318
<212> TYPE: DNA
<213> ORGANISM: Homo sapiens

<400> SEQUENCE: 94
gaaattgtgt tgacacagtc tccagccacc ctgtctttgt ctccagggga aagagccacc      60
ctctcctgca gtgccagctc aagtgtaagt tacatgtact ggtaccaaca gaaacctggc     120
```

```
caggctccca ggctcctcat ctatgacaca tccaacctgg cttctggcat cccagccagg      180
ttcagtggca gtgggtctgg gacagacttc actctcacca tcagcagcct agagcctgaa      240
gattttgcag tttattactg ttctcagtgg agtggttacc catacacgtt cggcggaggg      300
accaaggtgg agatcaaa                                                   318

<210> SEQ ID NO 95
<211> LENGTH: 119
<212> TYPE: PRT
<213> ORGANISM: Homo sapiens

<400> SEQUENCE: 95

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ala Lys Ile Ser Ser Gly Gly Ser Tyr Thr Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Leu Trp Gly Tyr Tyr Ala Leu Asp Tyr Trp Gly Gln Gly
            100                 105                 110

Thr Thr Val Thr Val Ser Ser
        115

<210> SEQ ID NO 96
<211> LENGTH: 357
<212> TYPE: DNA
<213> ORGANISM: Homo sapiens

<400> SEQUENCE: 96
gaggtgcagc tggtggagtc tgggggaggc ttggtccagc ctggggggtc cctgagactc       60
tcctgtgcag cctctggatt cacctttagt agctttgcca tgtcttgggt ccgccaggct      120
ccagggaagg ggctggagtg ggtggccaaa attagtagtg gtgggagtta cacctactat      180
cctgacactg tgacgggccg attcaccatc tccagagaca acgccaagaa ctcactgtat      240
ctgcaaatga acagcctgag agccgaggac acggctgtgt attactgtgc gagacagtta      300
tgggggtact atgctcttga ctactggggc caagggacca cggtcaccgt ctcctca        357

<210> SEQ ID NO 97
<211> LENGTH: 106
<212> TYPE: PRT
<213> ORGANISM: Homo sapiens

<400> SEQUENCE: 97

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ile Ser Val Ser Tyr Met
             20                  25                  30

Tyr Trp Tyr Gln Gln Lys Pro Gly Gln Ala Pro Arg Leu Leu Ile Tyr
         35                  40                  45

Asp Met Ser Asn Leu Ala Ser Gly Ile Pro Ala Arg Phe Ser Gly Ser
     50                  55                  60
```

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys
            100                 105

<210> SEQ ID NO 98
<211> LENGTH: 318
<212> TYPE: DNA
<213> ORGANISM: Homo sapiens

<400> SEQUENCE: 98
gaaattgtgt tgacacagtc tccagccacc ctgtctttgt ctccagggga aagagccacc       60
ctctcctgca gtgccagcat tagtgtaagt tacatgtact ggtaccaaca gaaacctggc      120
caggctccca ggctcctcat ctatgacatg tccaacctgg cttctggcat cccagccagg      180
ttcagtggca gtgggtctgg gacagacttc actctcacca tcagcagcct agagcctgaa      240
gattttgcag tttattactg tatgcagtgg agtggttacc catacacgtt cggcggaggg      300
accaaggtgg agatcaaa                                                    318

<210> SEQ ID NO 99
<211> LENGTH: 119
<212> TYPE: PRT
<213> ORGANISM: Homo sapiens

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Ile Trp Gly Gln Gly
            100                 105                 110

Thr Thr Val Thr Val Ser Ser
        115

<210> SEQ ID NO 100
<211> LENGTH: 357
<212> TYPE: DNA
<213> ORGANISM: Homo sapiens

<400> SEQUENCE: 100
gaggtgcagc tggtggagtc tgggggaggc ttggtccagc ctggggggtc cctgagactc       60
tcctgtgcag cctctggatt cacctttagt ccttttgcca tgtcttgggt ccgccaggct      120
ccagggaagg gctggagtg gtggccaaa attagtccgg gtgggagttg gacctactat      180
tctgacactg tgacgggccg attcaccatc tccagagaca cgccaagaa ctcactgtat      240 ctgcaaatga acagcctgag agccgaggac acggctgtgt attactgtgc gagacagtta      300

```
tgggggtact atgctcttga catttggggc caagggacca cggtcaccgt ctcctca      357
```

<210> SEQ ID NO 101
<211> LENGTH: 106
<212> TYPE: PRT
<213> ORGANISM: Homo sapiens

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Tyr Ser Val Ser Tyr Met
            20                  25                  30

Tyr Trp Tyr Gln Gln Lys Pro Gly Gln Ala Pro Arg Leu Leu Ile Tyr
        35                  40                  45

Asp Met Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys
            100                 105

<210> SEQ ID NO 102
<211> LENGTH: 318
<212> TYPE: DNA
<213> ORGANISM: Homo sapiens

<400> SEQUENCE: 102

```
gaaattgtgt tgacacagtc tccagccacc ctgtctttgt ctccagggga aagagccacc     60
ctctcctgca gtgccagcta tagtgtaagt tacatgtact ggtaccaaca gaaacctggc    120
caggctccca ggctcctcat ctatgacatg tccaacctgg cttctggcat cccagccagg    180
ttcagtggca gtgggtctgg gacagacttc actctcacca tcagcagcct agagcctgaa    240
gattttgcag tttattactg tatgcagtgg agtggttacc catacacgtt cggcggaggg    300
accaaggtgg agatcaaa                                                  318
```

<210> SEQ ID NO 103
<211> LENGTH: 119
<212> TYPE: PRT
<213> ORGANISM: Homo sapiens

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Gln Phe Ser Ser Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Tyr Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Phe Trp Gly Gln Gly
            100                 105                 110

Thr Thr Val Thr Val Ser Ser
        115

<210> SEQ ID NO 104
<211> LENGTH: 357
<212> TYPE: DNA
<213> ORGANISM: Homo sapiens

<400> SEQUENCE: 104
gaggtgcagc tggtggagtc tgggggaggc ttggtccagc ctggggggtc cctgagactc      60
tcctgtgcag cctctggatt ccagtttagt agctttgcca tgtcttgggt ccgccaggct     120
ccagggaagg ggctggagtg ggtggccaaa attagtccgg gtgggagtta cacctactat     180
tctgacactg tgacgggccg attcaccatc tccagagaca acgccaagaa ctcactgtat     240
ctgcaaatga acagcctgag agccgaggac acggctgtgt attactgtgc gagacagtta     300
tgggggtact atgctcttga cttttggggc caagggacca cggtcaccgt ctcctca        357

<210> SEQ ID NO 105
<211> LENGTH: 23
<212> TYPE: PRT
<213> ORGANISM: Homo sapiens

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 106
<211> LENGTH: 15
<212> TYPE: PRT
<213> ORGANISM: Homo sapiens

<400> SEQUENCE: 106

Trp Tyr Gln Gln Lys Pro Gly Gln Ala Pro Arg Leu Leu Ile Tyr
1               5                   10                  15

<210> SEQ ID NO 107
<211> LENGTH: 32
<212> TYPE: PRT
<213> ORGANISM: Homo sapiens

<400> SEQUENCE: 107

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 108
<211> LENGTH: 10
<212> TYPE: PRT
<213> ORGANISM: Homo sapiens

<400> SEQUENCE: 108

Phe Gly Gly Gly Thr Lys Val Glu Ile Lys
1               5                   10

<210> SEQ ID NO 109
<211> LENGTH: 25
<212> TYPE: PRT
<213> ORGANISM: Homo sapiens

<400> SEQUENCE: 109

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 110
<211> LENGTH: 14
<212> TYPE: PRT
<213> ORGANISM: Homo sapiens

<400> SEQUENCE: 110

Trp Val Arg Gln Ala Pro Gly Lys Gly Leu Glu Trp Val Ala
1               5                   10

<210> SEQ ID NO 111
<211> LENGTH: 32
<212> TYPE: PRT
<213> ORGANISM: Homo sapiens

<400> SEQUENCE: 111

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 112
<211> LENGTH: 11
<212> TYPE: PRT
<213> ORGANISM: Homo sapiens

<400> SEQUENCE: 112

Trp Gly Gln Gly Thr Thr Val Thr Val Ser Ser
1               5                   10

<210> SEQ ID NO 113
<211> LENGTH: 17
<212> TYPE: PRT
<213> ORGANISM: Homo sapiens

<400> SEQUENCE: 113

Glu Ile Ser Ser Gly Gly Ser Tyr Thr Tyr Tyr Pro Asp Thr Val Thr
1               5                   10                  15

Gly

<210> SEQ ID NO 114
<211> LENGTH: 10
<212> TYPE: PRT
<213> ORGANISM: Homo sapiens

<400> SEQUENCE: 114

Gly Leu Trp Gly Tyr Tyr Ala Leu Asp Tyr
1               5                   10

<210> SEQ ID NO 115
<211> LENGTH: 212
<212> TYPE: PRT
<213> ORGANISM: Homo sapiens

<400> SEQUENCE: 115

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30
```

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
            130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 116
<211> LENGTH: 106
<212> TYPE: PRT
<213> ORGANISM: Homo sapiens

<400> SEQUENCE: 116

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Val Ser Tyr Met
             20                  25                  30

Tyr Trp Tyr Gln Gln Lys Pro Gly Gln Ala Pro Arg Leu Leu Ile Tyr
             35                  40                  45

Asp Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Ser Gln Trp Ser Gly Tyr Pro Tyr Thr
                 85                  90                  95

Phe Gly Gly Gly Thr Lys Val Glu Ile Lys
            100                 105

<210> SEQ ID NO 117
<211> LENGTH: 378
<212> TYPE: DNA
<213> ORGANISM: Homo sapiens

<400> SEQUENCE: 117
atggaagccc cagcgcagct tctcttcctc ctgctactct ggctcccaga taccaccgga      60
gaaattgtgt tgacacagtc tccagccacc ctgtctttgt ctccagggga aagagccacc     120
ctctcctgca gtgccagctc aagtgtaagt tacatgtact ggtaccaaca gaaacctggc     180

```
caggctccca ggctcctcat ctatgacaca tccaacctgg cttctggcat cccagccagg      240
ttcagtggca gtgggtctgg gacagacttc actctcacca tcagcagcct agagcctgaa      300
gattttgcag tttattactg ttctcagtgg agtggttacc catacacgtt cggcggaggg      360
accaaggtgg agatcaaa                                                    378
```

<210> SEQ ID NO 118
<211> LENGTH: 119
<212> TYPE: PRT
<213> ORGANISM: Homo sapiens

<400> SEQUENCE: 118

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ala Lys Ile Ser Pro Gly Gly Ser Tyr Thr Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Leu Trp Gly Tyr Tyr Ala Leu Asp Tyr Trp Gly Gln Gly
            100                 105                 110

Thr Thr Val Thr Val Ser Ser
        115
```

<210> SEQ ID NO 119
<211> LENGTH: 414
<212> TYPE: DNA
<213> ORGANISM: Homo sapiens

<400> SEQUENCE: 119

```
atggagtttg gcctgagctg ggttttcctt gttgctattt tagaaggtgt ccagtgtgag      60
gtgcagctgg tggagtctgg gggaggcttg gtccagcctg gggggtccct gagactctcc      120
tgtgcagcct ctggattcac ctttagtagc tttgccatgt cttgggtccg ccaggctcca      180
gggaaggggc tggagtgggt ggccaaaatt agtcccggtg gaagttacac ctactatcct      240
gacactgtga cgggccgatt caccatctcc agagacaacg ccaagaactc actgtatctg      300
caaatgaaca gcctgagagc cgaggacacg gctgtgtatt actgtgcgag acagttatgg      360
gggtactatg ctcttgacta ctggggccaa gggaccacgg tcaccgtctc ctca           414
```

<210> SEQ ID NO 120
<211> LENGTH: 106
<212> TYPE: PRT
<213> ORGANISM: Homo sapiens

<400> SEQUENCE: 120

```
Glu Ile Val Leu Thr Gln Ser Pro Ala Thr Leu Ser Leu Ser Pro Gly
  1               5                  10                  15

Glu Arg Ala Thr Leu Ser Cys Ala Ser Ser Ser Val Ser Tyr Met
             20                  25                  30

Tyr Trp Tyr Gln Gln Lys Pro Gly Gln Ala Pro Arg Leu Leu Ile Tyr
         35                  40                  45

Asp Phe Ser Asn Leu Ala Ser Gly Ile Pro Ala Arg Phe Ser Gly Ser
```

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys
            100                 105

<210> SEQ ID NO 121
<211> LENGTH: 378
<212> TYPE: DNA
<213> ORGANISM: Homo sapiens

<400> SEQUENCE: 121
atggaagccc cagcgcagct tctcttcctc ctgctactct ggctcccaga taccaccgga      60
gaaattgtgt tgacacagtc tccagccacc ctgtctttgt ctccagggga aagagccacc     120
ctctcctgca gtgccagctc aagtgtaagt tacatgtact ggtaccaaca gaaacctggc     180
caggctccca ggctcctcat ctatgacttc tccaacctgg cttctggcat cccagccagg     240
ttcagtggca gtgggtctgg gacagacttc actctcacca tcagcagcct agagcctgaa     300
gattttgcag tttattactg tatgcagtgg agtggttacc catacacgtt cggcggaggg     360
accaaggtgg agatcaaa                                                    378

<210> SEQ ID NO 122
<211> LENGTH: 119
<212> TYPE: PRT
<213> ORGANISM: Homo sapiens

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Gln Phe Ser Pro Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Ile Trp Gly Gln Gly
            100                 105                 110

Thr Thr Val Thr Val Ser Ser
        115

<210> SEQ ID NO 123
<211> LENGTH: 414
<212> TYPE: DNA
<213> ORGANISM: Homo sapiens

<400> SEQUENCE: 123
atggagtttg gcctgagctg ggttttcctt gttgctattt tagaaggtgt ccagtgtgag      60
gtgcagctgg tggagtctgg gggaggcttg gtccagcctg gggggtccct gagactctcc     120
tgtgcagcct ctggattcca gtttagtccc tttgccatgt cttgggtccg ccaggctcca     180
gggaaggggc tggagtgggt ggccaaaatt agtcccggtg ggagttggac ctactatagc     240

```
gacactgtga cgggccgatt caccatctcc agagacaacg ccaagaactc actgtatctg    300
caaatgaaca gcctgagagc cgaggacacg gctgtgtatt actgtgcgag acagttatgg    360
gggtactatg ctcttgacat ttggggccaa gggaccacgg tcaccgtctc ctca          414
```

<210> SEQ ID NO 124
<211> LENGTH: 106
<212> TYPE: PRT
<213> ORGANISM: Homo sapiens

<400> SEQUENCE: 124

```
Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ile Ser Val Ser Tyr Met
            20                  25                  30

Tyr Trp Tyr Gln Gln Lys Pro Gly Gln Ala Pro Arg Leu Leu Ile Tyr
        35                  40                  45

Asp Met Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys
           100                 105
```

<210> SEQ ID NO 125
<211> LENGTH: 378
<212> TYPE: DNA
<213> ORGANISM: Homo sapiens

<400> SEQUENCE: 125

```
atggaagccc agcgcagct tctcttcctc ctgctactct ggctcccaga taccaccgga    60
gaaattgtgt tgacacagtc tccagccacc ctgtctttgt ctccagggga aagagccacc   120
ctctcctgca gtgccagcat tagtgtaagt tacatgtact ggtaccaaca gaaacctggc   180
caggctccca ggctcctcat ctatgacatg tccaacctgg cttctggcat cccagccagg   240
ttcagtggca gtgggtctgg gacagacttc actctcacca tcagcagcct agagcctgaa   300
gattttgcag tttattactg tatgcagtgg agtggttacc catacacgtt cggcggaggg   360
accaaggtgg agatcaaa                                                  378
```

<210> SEQ ID NO 126
<211> LENGTH: 119
<212> TYPE: PRT
<213> ORGANISM: Homo sapiens

<400> SEQUENCE: 126

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Gln Phe Ser Ser Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Tyr Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                    85                  90                  95

Ala Arg Gln Leu Trp Gly Tyr Tyr Ala Leu Asp Ile Trp Gly Gln Gly
                100                 105                 110

Thr Thr Val Thr Val Ser Ser
            115

<210> SEQ ID NO 127
<211> LENGTH: 414
<212> TYPE: DNA
<213> ORGANISM: Homo sapiens

<400> SEQUENCE: 127

```
atggagtttg gcctgagctg ggttttcctt gttgctattt tagaaggtgt ccagtgtgag    60
gtgcagctgg tggagtctgg gggaggcttg gtccagcctg gggggtccct gagactctcc   120
tgtgcagcct ctggattcca gtttagtagc tttgccatgt cttgggtccg ccaggctcca   180
gggaaggggc tggagtgggt ggccaaaatt agtcccggtg ggagttacac ctactatagc   240
gacactgtga cgggccgatt caccatctcc agagacaacg ccaagaactc actgtatctg   300
caaatgaaca gcctgagagc cgaggacacg gctgtgtatt actgtgcgag acagttatgg   360
gggtactatg ctcttgacat ttggggccaa gggaccacgg tcaccgtctc ctca         414
```

<210> SEQ ID NO 128
<211> LENGTH: 106
<212> TYPE: PRT
<213> ORGANISM: Homo sapiens

<400> SEQUENCE: 128

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Tyr Ser Val Ser Tyr Met
                20                  25                  30

Tyr Trp Tyr Gln Gln Lys Pro Gly Gln Ala Pro Arg Leu Leu Ile Tyr
            35                  40                  45

Asp Phe Ser Asn Leu Ala Ser Gly Ile Pro Ala Arg Phe Ser Gly Ser
 50                 55                  60

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys
            100                 105

<210> SEQ ID NO 129
<211> LENGTH: 378
<212> TYPE: DNA
<213> ORGANISM: Homo sapiens

<400> SEQUENCE: 129

```
atggaagccc cagcgcagct tctcttcctc ctgctactct ggctcccaga taccaccgga    60
gaaattgtgt tgacacagtc tccagccacc ctgtctttgt ctccagggga aagagccacc   120
ctctcctgca gtgccagcta cagtgtaagt tacatgtact ggtaccaaca gaaacctggc   180
caggctccca ggctcctcat ctatgacttc tccaacctgg cttctggcat cccagccagg   240
ttcagtggca gtgggtctgg gacagacttc actctcacca tcagcagcct agagcctgaa   300
gattttgcag tttattactg tatgcagtgg agtggttacc catacacgtt cggcggaggg   360
```

-continued

```
accaaggtgg agatcaaa                                                 378

<210> SEQ ID NO 130
<211> LENGTH: 119
<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Gln Phe Ser Pro Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Trp Thr Tyr Tyr Pro Asp Thr Asp
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Phe Trp Gly Gln Gly
            100                 105                 110

Thr Thr Val Thr Val Ser Ser
        115

<210> SEQ ID NO 131
<211> LENGTH: 414
<212> TYPE: DNA
<213> ORGANISM: Homo sapiens

<400> SEQUENCE: 131
atggagtttg gcctgagctg ggttttcctt gttgctattt tagaaggtgt ccagtgtgag    60
gtgcagctgg tggagtctgg gggaggcttg gtccagcctg ggggtccct gagactctcc    120 tgtgcagcct ctggattcca gtttagtccc tttgccatgt cttgggtccg ccaggctcca    180
gggaaggggc tggagtgggt ggccaaaatt agtcccggtg ggagttggac ctactatcct    240
gacactgaca cgggccgatt caccatctcc agagacaacg ccaagaactc actgtatctg    300
caaatgaaca gcctgagagc cgaggacacg gctgtgtatt actgtgcgag acagttatgg    360
gggtactatg ctcttgactt ctggggccaa gggaccacgg tcaccgtctc ctca        414

<210> SEQ ID NO 132
<211> LENGTH: 10
<212> TYPE: PRT
<213> ORGANISM: Homo sapiens
<220> FEATURE:
<221> NAME/KEY: unsure
<222> LOCATION: (2)(3)(4)(5)(7)
<223> OTHER INFORMATION: Wherein Xaa can be any one of the twenty
      naturally occurring amino acids.

<400> SEQUENCE: 132

Ser Xaa Xaa Xaa Xaa Val Xaa Tyr Met Tyr
 1               5                  10

<210> SEQ ID NO 133
<211> LENGTH: 7
<212> TYPE: PRT
<213> ORGANISM: Homo sapiens
<220> FEATURE:
<221> NAME/KEY: unsure
```

```
<222> LOCATION: (2)(4)(6)
<223> OTHER INFORMATION: Wherein Xaa can be any one of the twenty
      naturally occurring amino acids.

<400> SEQUENCE: 133

Asp Xaa Ser Xaa Leu Xaa Ser
 1               5

<210> SEQ ID NO 134
<211> LENGTH: 9
<212> TYPE: PRT
<213> ORGANISM: Homo sapiens
<220> FEATURE:
<221> NAME/KEY: unsure
<222> LOCATION: (1)(2)
<223> OTHER INFORMATION: Wherein Xaa can be any one of the twenty
      naturally occurring amino acids.

<400> SEQUENCE: 134

Xaa Xaa Trp Ser Gly Tyr Pro Tyr Thr
 1               5

<210> SEQ ID NO 135
<211> LENGTH: 10
<212> TYPE: PRT
<213> ORGANISM: Homo sapiens
<220> FEATURE:
<221> NAME/KEY: unsure
<222> LOCATION: (3)(4)(6)(9)
<223> OTHER INFORMATION: Wherein Xaa can be any one of the twenty
      naturally occurring amino acids.

<400> SEQUENCE: 135

Gly Phe Xaa Xaa Ser Xaa Phe Ala Xaa Ser
 1               5                  10

<210> SEQ ID NO 136
<211> LENGTH: 17
<212> TYPE: PRT
<213> ORGANISM: Homo sapiens
<220> FEATURE:
<221> NAME/KEY: unsure
<222> LOCATION: (2)(4)(8)(9)(11)(12)(15)(16)(17)
<223> OTHER INFORMATION: Wherein Xaa can be any one of the twenty
      naturally occurring amino acids.

<400> SEQUENCE: 136

Lys Xaa Ser Xaa Gly Gly Ser Xaa Xaa Tyr Xaa Xaa Asp Thr Xaa Xaa
 1               5                  10                  15

Xaa

<210> SEQ ID NO 137
<211> LENGTH: 10
<212> TYPE: PRT
<213> ORGANISM: Homo sapiens
<220> FEATURE:
<221> NAME/KEY: unsure
<222> LOCATION: (5)(10)
<223> OTHER INFORMATION: Wherein Xaa can be any one of the twenty
      naturally occurring amino acids.

<400> SEQUENCE: 137

Gln Leu Trp Gly Xaa Tyr Ala Leu Asp Xaa
 1               5                  10

<210> SEQ ID NO 138
<211> LENGTH: 9
<212> TYPE: PRT
<213> ORGANISM: Homo sapiens
```

<400> SEQUENCE: 138

Gln Gln Trp Ser Gly Tyr Pro Tyr Thr
1               5

METHODS OF TREATING CONDITIONS USING ANTI-IL-6 ANTIBODIES

CROSS-REFERENCE TO RELATED APPLICATIONS

This application is a divisional of U.S. patent application Ser. No. 12/470,753, filed 22 May 2009, now U.S. Pat. No. 7,833,755 currently allowed, which claims priority to U.S. patent application Ser. No. 11/413,561, filed 28 Apr. 2006, now U.S. Pat. No. 7,566,112, issued 14 Jul. 2009, which claims priority to U.S. Provisional Application Nos. 60/676,498, filed 29 Apr. 2005 and 60/677,319, filed 3 May 2005. The entire content of each of the aforesaid applications is incorporated herein by reference in their entireties.

FIELD OF THE INVENTION

The present invention relates to antibodies, including specified portions or variants, specific for at least one IL-6 protein or fragment thereof, as well as anti-idiotype antibodies, and nucleic acids encoding such anti-IL-6 antibodies, complementary nucleic acids, vectors, host cells, and methods of making and using thereof, including therapeutic formulations, administration and devices.

BACKGROUND OF THE INVENTION

IL-6 is a pleiotropic proinflammatory cytokine produced and secreted by a wide variety of cell types most notably antigen presenting cells, T and B cells. IL-6 is involved in such diverse activities as B cell growth and differentiation, T cell activation, hematopoiesis, osteoclast activation, keratinocyte growth, neuronal growth and hepatocyte activation. IL-6 binds to transmembrane or soluble IL-6R and signals through gp130, which is shared by several other cytokines.

IL-6 plays an important role in B cell abnormalities as demonstrated in systemic lupus erythematosus, multiple myeloma and lymphoproliferative disorders. Similarly, IL-6 is also implicated in the pathogenesis of autoimmune and inflammatory diseases such as rheumatoid arthritis and osteoarthritis. Recently, indirect evidence suggests an association between IL-6 and chronic obstructive pulmonary disease and insulin resistance in type 2 diabetes. IL-6 has both pro-inflammatory and anti-inflammatory effects in the immune system, indicating that this cytokine likely plays a central role in regulating the physiological response to disease. Therefore, targeting IL-6 can potentially provide therapeutic benefit in a variety of disease areas.

An increase in the production of IL-6 has been observed in a number of diseases including: Alzheimer's disease, autoimmune diseases, such as rheumatoid arthritis, inflammation, myocardial infarction, Paget's disease, osteoporosis, solid tumors (renal cell carcinoma), prostatic and bladder cancers, neurological cancers, and B-cell malignancies (e.g., Casteleman's disease, certain lymphomas, chronic lymphocytic leukemia, and multiple myeloma). Research has indicated that IL-6 is linked to the pathogenesis of many of these diseases, particularly, cancer and, therefore, blocking IL-6 should translate into clinical benefits.

Murine, chimeric, and other non-human anti-IL-6 antibodies have been developed; however, they may be limited in their potency, effectiveness, may often trigger an unacceptable immune response (i.e., immunogenicity) and/or require a high dosage (See, Trikha et al., Clin. Can. Res. 9, 4653-4665, October 2003, herein incorporated by reference). For example, antibodies containing non-human portions often give rise to an immune response in humans. Accordingly, repeated antibody administration is unsuitable as therapy and immune complex mediated clearance of antibodies from circulation can reduce the potency/effectiveness of the antibody. Serum sickness and anaphylaxis are two exemplary conditions that may be caused by repeat administration of antibodies having non-human portions. In this regard, an anti-IL-6 antibody with less potential for immunogenicity, i.e., more tolerable in humans, and that is more potent such that it requires a smaller dosage as compared to previously used anti-IL-6 antibodies is needed.

SUMMARY OF THE INVENTION

The present invention provides isolated human engineered, anti-IL-6 antibodies (also referred to as IL-6 antibodies), immunoglobulins, fragments, cleavage products and other specified portions and variants thereof, as well as anti-IL-6 antibody compositions, IL-6 anti-idiotype antibody, encoding or complementary nucleic acids, vectors, host cells, compositions, formulations, devices, transgenic animals, transgenic plants, and methods of making and using them.

The present invention provides, in one aspect, isolated nucleic acid molecules comprising, complementary, or hybridizing to, a polynucleotide encoding specific anti-IL-6 antibodies or anti-idiotype antibodies, comprising at least one specified sequence, domain, portion or variant thereof. The present invention further provides recombinant vectors comprising said anti-IL-6 antibody nucleic acid molecules, host cells containing such nucleic acids and/or recombinant vectors, as well as methods of making and/or using such antibody nucleic acids, vectors and/or host cells.

The present invention also provides at least one method for expressing at least one anti-IL-6 antibody, or IL-6 anti-idiotype antibody, in a host cell, comprising culturing a host cell as described herein under conditions wherein at least one anti-IL-6 antibody is expressed in detectable and/or recoverable amounts.

The present invention also provides at least one composition comprising (a) an isolated anti-IL-6 antibody encoding nucleic acid and/or antibody as described herein; and (b) a suitable and/or pharmaceutically acceptable carrier or diluent.

The present invention further provides at least one anti-IL-6 antibody method or composition, for administering a therapeutically effective amount to modulate or treat at least one IL-6 related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-IL-6 antibody, according to the present invention.

The present invention further provides at least one anti-IL-6 antibody method or composition, for diagnosing at least one IL-6 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-IL-6 antibody, according to the present invention.

Also provided is a medical device, comprising at least one isolated mammalian anti-IL-6 antibody of the invention, wherein the device is suitable for contacting or administering the at least one anti-IL-6 antibody, IL-6 anti-idiotypic antibody, nucleic acid molecule, compound, protein, and/or composition.

Also provided is an article of manufacture for human pharmaceutical or diagnostic use, comprising packaging material and a container comprising a solution or a lyophilized form of at least one isolated anti-IL-6 antibody of the present invention. The article of manufacture can optionally have the container as a component of a delivery device or system.

The present invention further provides any invention described herein.

DESCRIPTION OF THE FIGURES

FIGS. 5A and 5B show that human engineered anti-IL-6 antibody blocked IL-6-mediated stat3 phosphorylation as measured by Western Blot analysis shown through gel electrophoresis.

DESCRIPTION OF THE INVENTION

Figure 1:
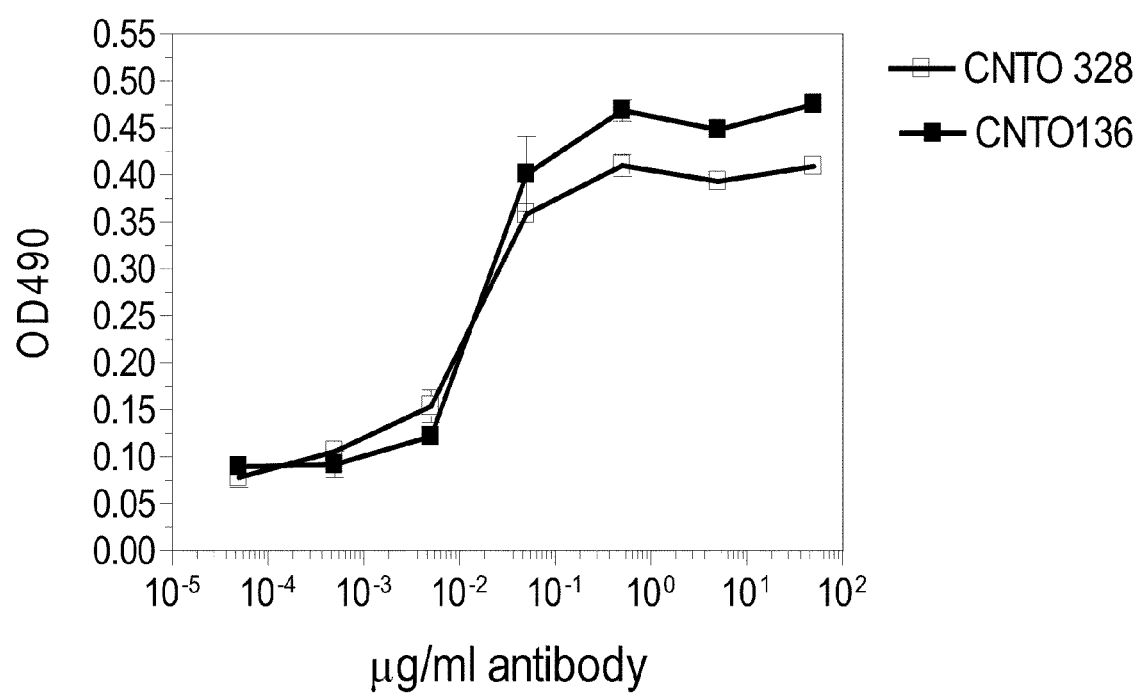
FIG. 1 shows the binding of human engineered and chimeric anti-IL-6 antibody to IL-6/IL-6R complex.
Figure 2:
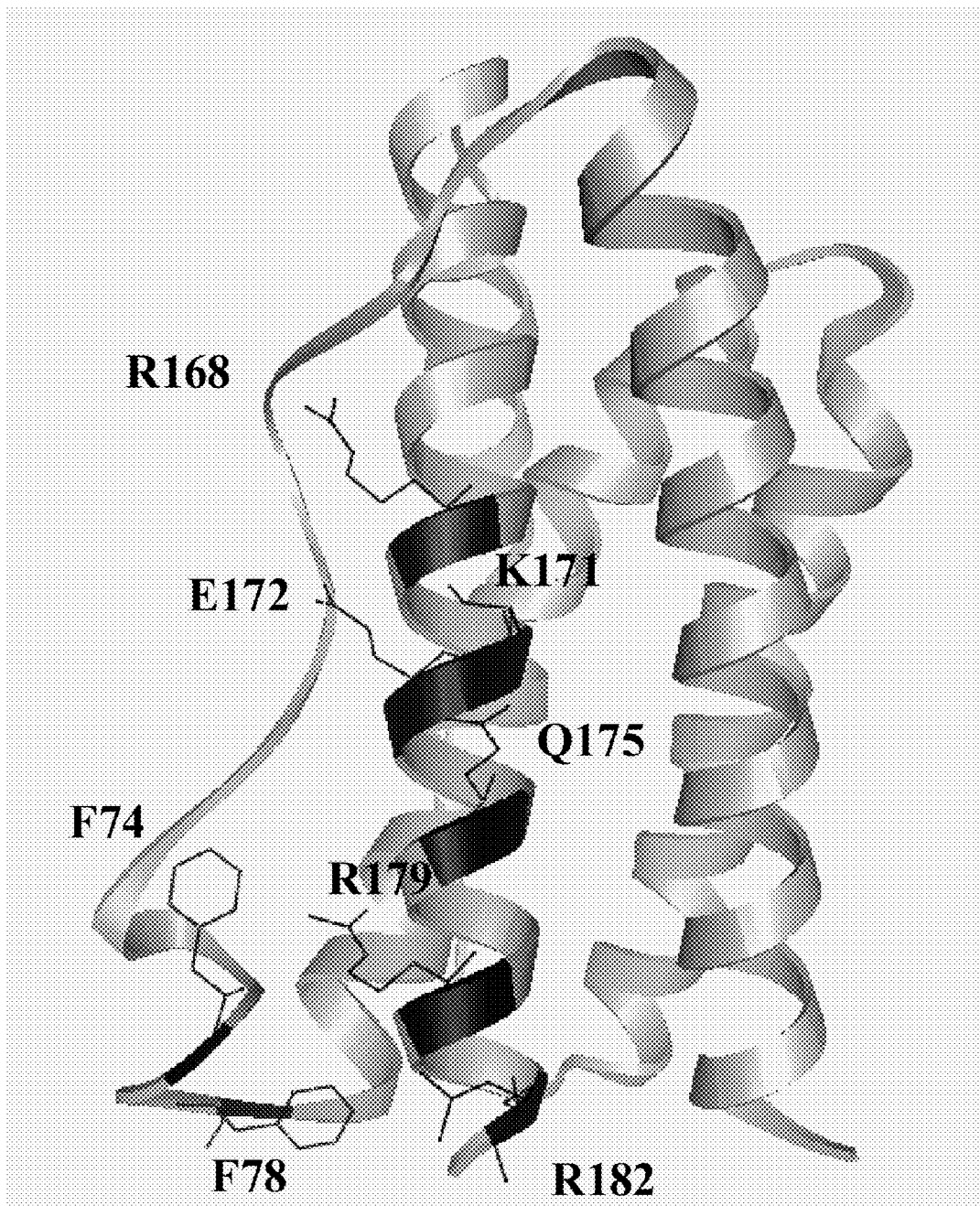
FIG. 2 shows the binding epitope for the human engineered anti-IL-6 antibody of the present invention.

The present invention provides isolated, recombinant and/or synthetic anti-IL-6 human engineered antibodies and IL-6 anti-idiotype antibodies thereto, as well as compositions and encoding nucleic acid molecules comprising at least one polynucleotide encoding at least one anti-IL-6 antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-IL-6 antibody," "IL-6 antibody," "anti-IL-6 antibody portion," or "anti-IL-6 antibody fragment" and/or "anti-IL-6 antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-6 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-6 activity or binding, or with IL-6 receptor activity or binding, in vitro, in situ and/or in vivo. As a non-limiting example, a suitable anti-IL-6 antibody, specified portion or variant of the present invention can bind at least one IL-6 molecule, or specified portions, variants or domains thereof. A suitable anti-IL-6 antibody, specified portion, or variant can also optionally affect at least one of IL-6 activity or function, such as but not limited to, RNA, DNA or protein synthesis, IL-6 release, IL-6 receptor signaling, membrane IL-6 cleavage, IL-6 activity, IL-6 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-6. For example, antibody fragments capable of binding to IL-6 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human engineered antibody" is an antibody with at least fully human frameworks and constant regions ($C_L$, $C_H$ domains (e.g., $C_H1$, $C_H2$, $C_H3$), and hinge), and CDRs derived from antigen binding antibodies. Fully human frameworks comprise frameworks that correspond to human germline sequences as well as sequences with somatic mutations. CDRs may be derived from one or more CDRs that bind to IL-6 in the context of any antibody framework. For example, the CDRs of the human engineered antibody of the present invention may be derived from CDRs that bind IL-6 in the context of a mouse antibody framework and then are engineered to bind IL-6 in the context of a fully human framework. Often, the human engineered antibody is substantially non-immunogenic in humans.

Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human engineered antibody is distinct from a chimeric or humanized antibody.

It is pointed out that a human engineered antibody can be produced by a non-human animal or prokaryotic or eukaryotic cell that is capable of expressing functionally rearranged human or human engineered immunoglobulin (e.g., heavy chain and/or light chain) genes. Further, when a human engineered antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human, human engineered, or humanized, antibodies that have binding specificities for at least two different antigens. In the present case, one of the binding specificities is for at least one IL-6 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule is usually done by affinity chromatography steps. Similar procedures are disclosed, e.g., in WO 93/08829, U.S. Pat. Nos. 6,210, 668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-6 antibodies useful in the methods and compositions of the present invention can optionally be characterized by high affinity binding to IL-6 and, optionally and preferably, as having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as the incidence of titrable levels of antibodies to the anti-IL-6 antibody in patients treated with anti-IL-6 antibody as occurring in less than 25% of patients treated, preferably, in less than 10% of patients treated with the recommended dose for the recommended course of therapy during the treatment period.

The isolated nucleic acids of the present invention can be used for production of at least one anti-IL-6 antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-6 condition, selected from, but not limited to, at least one of an immune disorder or disease, a cardiovascular disorder or disease, an infectious, malignant, and/or neurologic disorder or disease, or other known or specified IL-6 related condition.

Such a method can comprise administering an effective amount of a composition or a pharmaceutical composition comprising at least one anti-IL-6 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Antibodies of the Present Invention—Production and Generation

At least one anti-IL-6 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Human engineered antibodies that are specific for human IL-6 proteins or fragments thereof can be raised against an appropriate immunogenic antigen, such as an isolated IL-6 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Methods for engineering or humanizing non-human or human antibodies can also be used and are well known in the art. A humanized or engineered antibody may have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.html; www hhmi.org/grants/lectures/1996/vlab; www.path.cam.ac.uk/~mrc7/mikeimages.html; mcb.harvard.edu/BioLinks/Immunology.html; www.immunology link.com; pathbox.wustl.edu/~hcenter/index.html; www.appliedbiosystems.com; www.nal.usda.gov/awic/pubs/antibody; www.m.ehime-u.acjp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or engineered or human antibodies engineered with retention of high affinity for the antigen and other favorable biological properties. To achieve this goal, humanized (or human) or engineered antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human engineered IL-6 antibody of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In other embodiments, the human engineered IL-6 antibody of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a human framework region (e.g., the human framework regions shown below in Tables 13 and 14). In some embodiments, the framework region comprises SEQ ID NOS: 105, 106, 107, 108, 109, 110, 111, 112, or combinations thereof.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

Alternatively or additionally, it may be useful to combine amino acid modifications with one or more further amino acid modifications that alter C1q binding and/or the complement dependent cytotoxicity (CDC) function of the Fc region of an IL-6 binding molecule. The starting polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human engineered IL-6 antibody of the present invention with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human engineered IL-6 antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human engineered IL-6 antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of a human engineered IL-6 antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human engineered IL-6 antibody of the present invention is expressed in cells that express beta (1,4)-N-acetylglucosaminyltransferase III (GnT III), such that GnT III adds GlcNAc to the human engineered IL-6 antibody. Methods for producing antibodies in such a fashion are provided in WO/9954342, WO/03011878, patent publication 20030003097A1, and Umana et al., Nature Biotechnology, 17:176-180, February 1999.

A human anti-IL-6 antibody can be optionally generated by immunization of a transgenic animal (e.g., mouse, rat, hamster, non-human primate, and the like) capable of producing a repertoire of human antibodies, as described herein and/or as known in the art. Cells that produce a human anti-IL-6 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770, 428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature*

*Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; 5,223,409, 5,403,484, 5,571, 698, 5,837,500, assigned to Dyax, 5,427,908, 5,580,717, assigned to Affymax; 5,885,793, assigned to Cambridge Antibody Technologies; 5,750,373, assigned to Genentech, 5,618,920, 5,595,898, 5,576,195, 5,698,435, 5,693,493, 5,698,417, assigned to Xoma, Colligan, supra; Ausubel, supra; or Sambrook, supra. Antibodies of the present invention can also be prepared using at least one anti-IL-6 antibody encoding nucleic acid to provide transgenic animals or mammals, such as goats, cows, horses, sheep, rabbits and the like, that produce such antibodies in their milk. Such animals can be provided using known methods. See, e.g., but not limited to, U.S. Pat. Nos. 5,827,690; 5,849,992; 4,873,316; 5,849, 992; 5,994,616; 5,565,362; 5,304,489, and the like, each of which is entirely incorporated herein by reference.

Antibodies of the present invention can additionally be prepared using at least one anti-IL-6 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbiol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein.

The antibodies of the invention can bind human IL-6 with a wide range of affinities ($K_D$). In a preferred embodiment, at least one human mAb of the present invention can optionally bind human IL-6 with high affinity. For example, a human or human engineered mAb can bind human IL-6 with a $K_D$ equal to or less than about $10^{-7}$ M, such as but not limited to, 0.1-9.9 (or any range or value therein) X $10^{-7}$, $10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_{on}$, $K_{off}$) are preferably made with standardized solutions of antibody and antigen, and a standardized buffer, such as the buffer described herein.

Competitive assays can be performed with the antibody of the present invention in order to determine what proteins, antibodies, and other antagonists compete for binding to IL-6 with the antibody of the present invention and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to IL-6 is separated from the unbound sample, for example, by decanting (where the protein/antibody was pre-insolubilized) or by centrifuging (where the protein/antibody was precipitated after the competitive reaction). Also, the competitive binding may be determined by whether function is altered by the binding or lack of binding of the antibody to the protein, e.g., whether the antibody molecule inhibits or potentiates the enzymatic activity of, for example, a label. ELISA and other functional assays may be used, as well known in the art.

Preferred anti-IL-6 antibodies of the invention have the sequences shown in Tables 1-5 and 12-14 below. For example, an anti-IL-6 antibody of the invention has one of the light chain CDR sequences shown in Table 1 (i.e., CDRL1, CDRL2, and CDRL3) and one of the heavy chain CDR sequences shown in Table 2 (i.e., CDRH1, CDRH2, and CDRH3). More specifically, an anti-IL-6 antibody (molecule AME-A9) has the CDRL1 of SEQ ID NO:15, CDRL2 of SEQ ID NO:27, CDRL3 of SEQ ID NO:35, CDRH1 of SEQ ID NO:47, CDRH2 of SEQ ID NO:61, CDRH3 of SEQ ID NO:91.

Nucleic Acid Molecules

Using the information provided herein, for example, the nucleotide sequences encoding at least 70-100% of the contiguous amino acids of at least one of the light chain variable regions of SEQ ID NOS: 93, 97, and 101, among other sequences disclosed herein, and at least one of the heavy chain variable regions of SEQ ID NOS: 95, 99, and 103, among other sequences disclosed herein, specified fragments, variants or consensus sequences thereof, or a deposited vector comprising at least one of these sequences, a nucleic acid molecule of the present invention encoding at least one anti-IL-6 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain (e.g., SEQ ID NOS: 38, 40, 42, 44, etc.) or light chain (e.g., SEQ ID NOS: 2, 4, 6, 8, etc.); nucleic acid molecules comprising the coding sequence for an anti-IL-6 antibody or variable region (e.g., light chain variable regions of SEQ ID NOS: 94, 98, and 102, among other sequences disclosed herein, and heavy chain variable regions of SEQ ID NOS: 96, 100, and 104); and nucleic acid molecules which comprise a nucleotide sequence substantially different from those described above but which, due to the degeneracy of the genetic code, still encode at least one anti-IL-6 antibody as described herein and/or as known in the art. Of course, the genetic code is well known in the art. Thus, it would be routine for one skilled in the art to generate such degenerate nucleic acid variants that code for specific anti-IL-6 antibodies of the present invention. See, e.g., Ausubel, et al., supra, and such nucleic acid variants are included in the present invention.

As indicated herein, nucleic acid molecules of the present invention which comprise a nucleic acid encoding an anti-IL-6 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example, a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells

The present invention also relates to vectors that include isolated nucleic acid molecules of the present invention, host cells that are genetically engineered with the recombinant vectors, and the production of at least one anti-IL-6 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134;

4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenylation or transcription terminator sequences are typically incorporated into the vector. An example of a terminator sequence is the polyadenylation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-6 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-6 Antibodies

An anti-IL-6 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, or as shown in SEQ ID NOS: 105-112, further optionally comprising at least one substitution, insertion or deletion), a heavy chain or light chain constant region, (e.g., comprising at least one CH1, hinge1, hinge2, hinge3, hinge4, CH2, or CH3 or fragment thereof, further optionally comprising at least one substitution, insertion or deletion), or any portion thereof, that can be incorporated into an antibody of the present invention. An antibody of the invention can include or be derived from any mammal, such as but not limited to, a human, a mouse, a rabbit, a rat, a rodent, a primate, or any combination thereof, and the like.

The isolated antibodies of the present invention comprise the antibody amino acid sequences disclosed herein encoded by any suitable polynucleotide, or any isolated or prepared antibody. Preferably, the human antibody or antigen-binding fragment binds human IL-6 and, thereby, partially or substantially neutralizes at least one biological activity of the protein. An antibody, or specified portion or variant thereof, that partially or preferably substantially neutralizes at least one biological activity of at least one IL-6 protein or fragment can bind the protein or fragment and thereby inhibit activities mediated through the binding of IL-6 to the IL-6 receptor or through other IL-6-dependent or mediated mechanisms. As used herein, the term "neutralizing antibody" refers to an antibody that can inhibit an IL-6-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-6 antibody to inhibit an IL-6-dependent activity is preferably assessed by at least one suitable IL-6 protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, or γ4). Antibodies of this type can be prepared by employing a transgenic mouse or other transgenic non-human mammal comprising at least one human light chain (e.g., IgG, IgA, and IgM) transgenes as described herein and/or as known in the art. In another embodiment, the anti-human IL-6 human antibody comprises an IgG1 heavy chain and an IgG1 light chain.

At least one antibody of the invention binds at least one specified epitope specific to at least one IL-6 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. The at least one specified epitope can comprise any combination of at least one amino acid sequence of at least 1-3 amino acids to the entire specified portion of contiguous amino acids of SEQ ID NO:115, for example, amino acid residues 151-178, more specifically, residues 171-182.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original mouse CDRs can be used. These CDRs may be formed by incorporation of conservative substitutions from the original mouse sequence. As a non-limiting example, the antibody or antigen-binding portion or variant can comprise at least one of the heavy chain CDR3 having an amino acid sequence selected from the group consisting of SEQ ID NOS: 79, 81, 83, 85, 87, 89, and 91, and/or a light chain CDR3 having an amino acid sequence selected from the group consisting of SEQ ID NOS:29, 31, 33, and 35. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2, and/or 3 (e.g., SEQ ID NOS:37, 49, and 79). In another particular embodiment, the antibody or anti-gen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS:1, 17, and 29).

In a preferred embodiment, the three heavy chain CDRs and the three light chain CDRs of the antibody or antigen-binding fragment have the amino acid sequence of the corresponding CDR of at least one of mAb AME-A9, AME-1b, AME-18a, AME-22a, AME-20b, AME-23a, and AME-19a, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-6 antibody can comprise at least one of a heavy or light chain variable region having a defined amino acid sequence. For example, in a preferred embodiment, the anti-IL-6 antibody comprises at least one of at least one heavy chain variable region, optionally having an amino acid sequence selected from the group consisting of SEQ ID NOS: 95, 99, 103, 118, 122, 126, and 130, and/or at least one light chain variable region, optionally having an amino acid sequence selected from the group consisting of SEQ ID NOS: 93, 97, 101, 116, 120, 124, and 128. Antibodies that bind to human IL-6 and that comprise a defined heavy or light chain variable region can be prepared using suitable methods, such as phage display (Katsube, Y., et al., *Int J Mol. Med*, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-6 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

Amino Acid Codes

The amino acids that make up anti-IL-6 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994)

An anti-IL-6 antibody of the present invention can include one or more amino acid substitutions, deletions or additions, either from natural mutations or human manipulation, as specified herein. Amino acids in an anti-IL-6 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244: 1081-1085 (1989)). The latter procedure introduces single alanine mutations at every residue in the molecule. The resulting mutant molecules are then tested for biological activity, such as, but not limited to, at least one IL-6 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-6 antibodies of the present invention can include, but are not limited to, at least one portion, sequence or combination selected from 5 to all of the contiguous amino acids of at least one of SEQ ID NOS: 91, 93, 95, 97, 99, etc.

Non-limiting variants that can enhance or maintain at least one of the listed activities include, but are not limited to, any of the above polypeptides, further comprising at least one mutation corresponding to at least one substitution in the residues varied among the disclosed variant amino acid sequences.

An anti-IL-6 antibody can further optionally comprise a polypeptide with an amino acid sequence that varies from the sequence of the contiguous amino acids of at least one of SEQ ID NOS:95, 99, and 103, etc (e.g., one or more conservative substitutions from the sequences provided herein). Also, the present invention comprises variants of the amino acid sequence of a light chain variable region of SEQ ID NOS:93, 97, or 101, or the amino acid sequence of a heavy chain of SEQ ID NOS: 79, 81, 83, 85, 87, 89, or 91.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-1000% or more of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphoramide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

Anti-Idiotype Antibodies to Anti-Il-6 Antibody Compositions

In addition to monoclonal anti-IL-6 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g., mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

The present invention also provides at least one anti-IL-6 antibody composition comprising at least one, at least two, at least three, at least four, at least five, at least six or more anti-IL-6 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-6 antibody amino acid sequence selected from the group consisting of 70-100% of the contiguous amino acids of SEQ ID NOS:1-114 and 116-138, or specified fragments, domains or variants thereof. Preferred anti-IL-6 antibody compositions include at least one or two full length, fragments, domains or variants as at least one CDR or LBP containing portions of the anti-IL-6 antibody sequence described herein, for example, 70-100% of SEQ ID NOS:15, 27, 35, 47, 61, and 91, or specified fragments, domains or variants thereof. Further preferred compositions comprise, for example, 40-99% of at least one of 70-100% of SEQ ID NOS: 93, 95, 97, 99, 101, 103, etc., or specified fragments, domains or variants thereof. Such composition percentages are by weight, volume, concentration, molarity, or molarity as liquid or dry solutions, mixtures, suspension, emulsions, particles, powder, or colloids, as known in the art or as described herein.

Antibody Compositions Comprising Further Therapeutically Active Ingredients

The antibody compositions of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, optic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from nonnarcotic analgesics or at least one selected from antipyretics, nonsteroidal anti-inflammatory drugs, narcotic or at least one opiod analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antiitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, optic, and nasal drugs can be at least one selected from ophthalmic anti-infectives, ophthalmic anti-inflammatories, miotics, mydriatics, ophthalmic vasoconstrictors, miscellaneous ophthalmics, optics, and nasal drugs. The topical drug can be at least one selected from local anti-infectives, scabicides or at least one pediculicide or topical corticosteroid. The nutritional drug can be at least one selected from vitamins, minerals, or calories. See, e.g., contents of *Nursing* 2001 *Drug Handbook*, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxicillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of *Nursing* 2001 *Drug Handbook*.)

The at least one inotropic can be at least one selected from amrinone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecaimide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocainide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrochloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of *Nursing* 2001 *Drug Handbook*.)

The at least one nonnarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenytoin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of *Nursing* 2001 *Drug Handbook*.)

The at least one cholinergic (e.g., parasymathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of *Nursing* 2001 *Drug Handbook*.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, dornase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of *Nursing* 2001 *Drug Handbook*.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluid extract, cascara sagrada fluid extract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondensetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of *Nursing* 2001 *Drug Handbook*.)

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide $^{131}$I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of *Nursing* 2001 *Drug Handbook*.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of *Nursing* 2001 *Drug Handbook*.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of *Nursing* 2001 *Drug Handbook*.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, *bacillus* Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of *Nursing* 2001 *Drug Handbook*.)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatitis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), and *Micrurus fulvius* antivenin. The at least one immune serum can be at least one selected from cytomegalovirus immune globulin (intravenous), hepatitis B immune globulin (human), immune globulin intramuscular, immune globulin intravenous, rabies immune globulin (human), respiratory syncytial virus immune globulin intravenous (human), $Rh_0(D)$ immune globulin (human), $Rh_0(D)$ immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of *Nursing* 2001 *Drug Handbook*.)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylcholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one optic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of *Nursing* 2001 *Drug Handbook*.)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocortisone valerate, mometasone furoate, and triamcinolone acetonide. (See, e.g., pp. 1098-1136 of *Nursing* 2001 *Drug Handbook*.)

The at least one vitamin or mineral can be at least one selected from vitamin A, vitamin B complex, cyancobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of *Nursing* 2001 *Drug Handbook*.)

Anti-IL-6 antibody compositions of the present invention can further comprise at least one of any suitable and effective amount of a composition or pharmaceutical composition comprising at least one anti-IL-6 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23 (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholera, Vibrios parahemolyticus*), *Klebsiella* species, *Pseudomonas aeruginosa,* and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-IL-6 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the anti-IL-6 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-6 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-6 antibody compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-6 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-6 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used as known in the art, such as about 0.0015%, or any range, value, or fraction therein. Non-limiting examples include, no preservative, about 0.1-2% m-cresol (e.g., 0.2, 0.3, 0.4, 0.5, 0.9, 1.0%), about 0.1-3% benzyl alcohol (e.g., 0.5, 0.9, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-IL-6 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-IL-6 antibody, and a second vial comprising an aqueous diluent of prescribed buffer or preservative, wherein said packaging material comprises a label that instructs a patient to reconstitute the at least one anti-IL-6 antibody in the aqueous diluent to form a solution that can be held over a period of twenty-four hours or greater.

The at least one anti-IL-6 antibody used in accordance with the present invention can be produced by recombinant means, including from mammalian cell or transgenic preparations, or can be purified from other biological sources, as described herein or as known in the art.

The range of at least one anti-IL-6 antibody in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-IL-6 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-6 antibody and preservative in an aqueous diluent is carried out using conventional dissolution and mixing procedures. To prepare a suitable formulation, for example, a measured amount of at least one anti-IL-6 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-IL-6 antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biological activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-IL-6 antibody of the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-6 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-6 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject® NovoPen®, B-D®Pen, AutoPen®, and OptiPen® GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors and needle free IV infusion sets.

The products presently claimed include packaging material. The packaging material provides, in addition to the information required by the regulatory agencies, the conditions under which the product can be used. The packaging material of the present invention provides instructions to the patient to reconstitute the at least one anti-IL-6 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-IL-6 antibody and a selected buffer, preferably, a phosphate buffer containing saline or a chosen salt. Mixing the at least one anti-IL-6 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-IL-6 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-6 antibody may result in other than a clear solution of lyophilized powder comprising the antibody. Among non-clear solutions are formulations comprising particulate suspensions, said particulates being a composition containing the anti-IL-6 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gelatin agar, starch, arabinogalactan, albumin, collagen, polyglycolic acid, polylactic aced, glycolide-L(−) lactide poly(epsilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(epsilon-caprolactone, poly (epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one anti-IL-6 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one IL-6 related disease, in a cell, tissue, organ, animal, or patient, as known in the art or as described herein, using at least one IL-6 antibody of the present invention, e.g., administering or contacting the cell, tissue, organ, animal, or patient with a therapeutic effective amount of IL-6 antibody. The present invention also provides a method for modulating or treating at least one IL-6 related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one IL-6 related immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondylitis, gastric ulcer, seronegative arthropathies, osteoarthritis, osteolysis, aseptic loosening of orthopedic implants, inflammatory bowel disease, ulcerative colitis, systemic lupus erythematosus, cutaneous lupus erythematosus, lupus nephritis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemochromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, acute coronary syndrome, arteriosclerosis, atherosclerosis, restenosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aortic and peripheral aneurysms, aortic dissection, inflammation of the aorta, occlusion of the abdominal aorta and its branches, peripheral vascular disorders, occlusive arterial disorders, peripheral atherosclerotic disease, thromboangiitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-IL-6 antibody to a cell, tissue, organ, animal or patient in need of such modulation, treatment or therapy.

The present invention also provides a method for modulating or treating at least one IL-6 related infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidydimitis, *legionella*, lyme disease, influenza a, epstein-barr virus, viral-associated hemaphagocytic syndrome, viral encephalitis/aseptic meningitis, and the like.

The present invention also provides a method for modulating or treating at least one IL-6 related malignant disease in a cell, tissue, organ, animal or patient, including, but not limited to, at least one of: leukemia, acute leukemia, acute lymphoblastic leukemia (ALL), acute lymphocytic leukemia, B-cell, T-cell or FAB ALL, acute myeloid leukemia (AML), acute myelogenous leukemia, chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary non-polyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

The present invention also provides a method for modulating or treating at least one IL-6 related neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; Dementia pugilistica; neurotraumatic injury (e.g., spinal cord injury, brain injury, concussion, repetitive concussion); pain; inflammatory pain; autism; depression; stroke; cognitive disorders; epilepsy; and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, $16^{th}$ Edition, Merck & Company, Rahway, N.J. (1992).

The present invention also provides a method for modulating or treating at least one IL-6 related wound, trauma or tissue injury or related chronic condition, in a cell, tissue, organ, animal or patient, including, but not limited to, at least one of: bodily injury or a trauma associated with oral surgery including periodontal surgery, tooth extraction(s), endodontic treatment, insertion of tooth implants, application and use of tooth prosthesis; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is an aphthous wound, a traumatic wound or a herpes associated wound.

Wounds and/or ulcers are normally found protruding from the skin or on a mucosal surface or as a result of an infarction in an organ ("stroke"). A wound may be a result of a soft tissue defect or a lesion or of an underlying condition. In the present context, the term "skin" relates to the outermost surface of the body of an animal, including a human, and embraces intact or almost intact skin as well as an injured skin surface. The term "mucosa" relates to undamaged or damaged mucosa of an animal, such as a human, and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore," "lesion," "necrosis," and "ulcer." Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

The term "wound" used in the present context denotes any wound (see below for a classification of wounds) and at any particular stage in the healing process, including the stage before any healing has initiated or even before a specific wound like a surgical incision is made (prophylactic treatment). Examples of wounds which can be prevented and/or treated in accordance with the present invention are, e.g., aseptic wounds, contused wounds, incised wounds, lacerated wounds, non-penetrating wounds (i.e., wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores, etc. Examples of ulcers are, e.g., a peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, and veneral ulcer, e.g., caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore, as mentioned above, in the present context the term "wound" encompasses the terms "ulcer," "lesion," "sore" and "infarction," and the terms are indiscriminately used unless otherwise indicated.

The kinds of wounds to be treated according to the invention include also (i) general wounds, such as, e.g., surgical, traumatic, infectious, ischemic, thermal, chemical and bullous wounds; (ii) wounds specific for the oral cavity, such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotizing ulcerative gingivitis and burning mouth syndrome are specific examples; and (iii) wounds on the skin, such as, e.g., neoplasm, burns (e.g. chemical, thermal), lesions (bacterial, viral, autoimmunological), bites and surgical incisions. Another way of classifying wounds is as (i) small tissue loss due to surgical incisions, minor abrasions and minor bites, or as (ii) significant tissue loss. The latter group includes ischemic ulcers, pressure sores, fistulae, lacerations, severe bites, thermal burns and donor site wounds (in soft and hard tissues) and infarctions.

Other wounds that are of importance in connection with the present invention are wounds like ischemic ulcers, pressure sores, fistulae, severe bites, thermal burns and donor site wounds. Ischemic ulcers and pressure sores are wounds which normally only heal very slowly and especially in such cases, an improved and more rapid healing process is of course of great importance for the patient. Furthermore, the costs involved in the treatment of patients suffering from such wounds are markedly reduced when the healing is improved and takes place more rapidly.

Donor site wounds are wounds which, e.g., occur in connection with removal of hard tissue from one part of the body to another part of the body, e.g., in connection with transplantation. The wounds resulting from such operations are very painful and an improved healing is therefore most valuable. The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

The present invention also provides a method for modulating or treating osteoarthritis, systemic lupus erythematosus, cutaneous lupus erythematosus, lupus nephritis, type II diabetes mellitus, and chronic obstructive pulmonary disorder, among the other diseases listed above as IL-6 related, in a cell, tissue, organ, animal, or patient including, but not limited to, at least one of immune related disease, cardiovascular disease, infectious, malignant and/or neurologic disease. Such a method can optionally comprise administering an effective amount of at least one composition or pharmaceutical composition comprising at least one anti-IL-6 antibody to a cell, tissue, organ, animal or patient in need of such modulation, treatment or therapy.

Any method of the present invention can comprise administering an effective amount of a composition or pharmaceutical composition comprising at least one anti-IL-6 antibody to a cell, tissue, organ, animal or patient in need of such modulation, treatment or therapy. Such a method can optionally further comprise co-administration or combination therapy for treating such diseases or disorders, wherein the administering of said at least one anti-IL-6 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept (Enbrel™), adalimumab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J. each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF antibodies (e.g., at least one TNF antagonist as defined above), antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or, preferably, in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

An example of a TNF antibody or antagonist is the chimeric antibody cA2. Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention.

TNF receptor multimeric molecules useful in the present invention comprise all or a functional portion of the ECD of two or more TNF receptors linked via one or more polypeptide linkers or other nonpeptide linkers, such as polyethylene glycol (PEG). An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116, 964; Capon et al., U.S. Pat. No. 5,225,538; and Capon et al., *Nature* 337:525-531 (1989), which references are entirely incorporated herein by reference.

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments

Any method of the present invention can comprise a method for treating an IL-6 mediated disorder, comprising administering an effective amount of a composition or pharmaceutical composition comprising at least one anti-IL-6 antibody to a cell, tissue, organ, animal or patient in need of such modulation, treatment or therapy. Such a method can optionally further comprise co-administration or combination therapy for treating such diseases or disorders, wherein the administering of said at least one anti-IL-6 antibody, specified portion or variant thereof, further comprises administering before, concurrently, and/or after, at least one selected from an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, optic or nasal drug, a topical drug, a nutritional drug or the like, at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Such drugs are well known in the art, including formulations, indications, dosing and administration for each presented herein (see., e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

Typically, treatment of pathologic conditions is effected by administering an effective amount or dosage of at least one anti-IL-6 antibody composition that total, on average, a range from at least about 0.01 to 500 milligrams of at least one anti-IL-6 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include about 0.1-99 and/or 100-500 mg/kg/administration, or any range, value or fraction thereof, or to achieve a serum concentration of about 0.1-5000 µg/ml serum concentration per single or multiple administration, or any range, value or fraction thereof. A preferred dosage range for the anti-IL-6 antibody of the present invention is from about 1 mg/kg, up to about 3, about 6 or about 12 mg/kg of body weight of the patient.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention about 0.1 to 100 mg/kg or any range, value or fraction thereof per day, on at least one of day 1-40, or, alternatively or additionally, at least one of week 1 52, or, alternatively or additionally, at least one of 1-20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and about 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of at least one anti-IL-6 antibody according to the present invention. While pulmonary administration is used in the following description, other modes of administration can be used according to the present invention with suitable results. IL-6 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-IL-6 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. At least one anti-IL-6 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Pulmonary/Nasal Administration

For pulmonary administration, preferably, at least one anti-IL-6 antibody composition is delivered in a particle size effective for reaching the lower airways of the lung or sinuses. According to the invention, at least one anti-IL-6 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use formulations suitable for the administration for the dispensing of antibody in an aerosol. Such aerosols can be comprised of either solutions (both aqueous and non aqueous) or solid particles.

Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention.

Preferably, a composition comprising at least one anti-IL-6 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g., less than about 10 µm, preferably about 1-5 µm, for good respirability.

Administration of IL-6 Antibody Compositions as a Spray

A spray including IL-6 antibody composition can be produced by forcing a suspension or solution of at least one anti-IL-6 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-IL-6 antibody composition delivered by a sprayer have a particle size less than about 10 µm, preferably, in the range of about 1 µm to about 5 µm, and, most preferably, about 2 µm to about 3 µm.

Formulations of at least one anti-IL-6 antibody composition suitable for use with a sprayer typically include antibody composition in an aqueous solution at a concentration of about 0.1 mg to about 100 mg of at least one anti-IL-6 antibody composition per ml of solution or mg/gm, or any range, value, or fraction therein. The formulation can include agents, such as an excipient, a buffer, an isotonicity agent, a preservative, a surfactant, and, preferably, zinc. The formulation can also include an excipient or agent for stabilization of the antibody composition, such as a buffer, a reducing agent, a bulk protein, or a carbohydrate. Bulk proteins useful in formulating antibody compositions include albumin, protamine, or the like. Typical carbohydrates useful in formulating antibody compositions include sucrose, mannitol, lactose, trehalose, glucose, or the like. The antibody composition formulation can also include a surfactant, which can reduce or prevent surface-induced aggregation of the antibody composition caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein, such as IL-6 antibodies, or specified portions or variants, can also be included in the formulation.

Administration of IL-6 Antibody Compositions by a Nebulizer

Antibody compositions of the invention can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition either directly or through a coupling fluid, creating an aerosol including the antibody composition. Advantageously, particles of antibody composition delivered by a nebulizer have a particle size less than about 10 μm, preferably, in the range of about 1 μm to about 5 μm, and, most preferably, about 2 μm to about 3 μm.

Formulations of at least one anti-IL-6 antibody suitable for use with a nebulizer, either jet or ultrasonic, typically include a concentration of about 0.1 mg to about 100 mg of at least one anti-IL-6 antibody protein per ml of solution. The formulation can include agents, such as an excipient, a buffer, an isotonicity agent, a preservative, a surfactant, and, preferably, zinc. The formulation can also include an excipient or agent for stabilization of the at least one anti-IL-6 antibody composition, such as a buffer, a reducing agent, a bulk protein, or a carbohydrate. Bulk proteins useful in formulating at least one anti-IL-6 antibody compositions include albumin, protamine, or the like. Typical carbohydrates useful in formulating at least one anti-IL-6 antibody include sucrose, mannitol, lactose, trehalose, glucose, or the like. The at least one anti-IL-6 antibody formulation can also include a surfactant, which can reduce or prevent surface-induced aggregation of the at least one anti-IL-6 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein, such as antibody protein, can also be included in the formulation.

Administration of IL-6 Antibody Compositions by a Metered Dose Inhaler

In a metered dose inhaler (MDI), a propellant, at least one anti-IL-6 antibody, and any excipients or other additives are contained in a canister as a mixture including a liquefied compressed gas. Actuation of the metering valve releases the mixture as an aerosol, preferably containing particles in the size range of less than about 10 μm, preferably, about 1 μm to about 5 μm, and, most preferably, about 2 μm to about 3 μm. The desired aerosol particle size can be obtained by employing a formulation of antibody composition produced by various methods known to those of skill in the art, including jet-milling, spray drying, critical point condensation, or the like. Preferred metered dose inhalers include those manufactured by 3M or Glaxo and employing a hydrofluorocarbon propellant. Formulations of at least one anti-IL-6 antibody for use with a metered-dose inhaler device will generally include a finely divided powder containing at least one anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably, the propellant is a hydrofluorocarbon. The surfactant can be chosen to stabilize the at least one anti-IL-6 antibody as a suspension in the propellant, to protect the active agent against chemical degradation, and the like. Suitable surfactants include sorbitan trioleate, soya lecithin, oleic acid, or the like. In some cases, solution aerosols are preferred using solvents, such as ethanol. Additional agents known in the art for formulation of a protein can also be included in the formulation. One of ordinary skill in the art will recognize that the methods of the current invention can be achieved by pulmonary administration of at least one anti-IL-6 antibody composition via devices not described herein.

Oral Formulations and Administration

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and antibodies and a combination of at least two surfactants intended for oral, buccal, mucosal, nasal, pulmonary, vaginal transmembrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,5,871,753 and used to deliver biologically active agents orally are known in the art.

Mucosal Formulations and Administration

A formulation for orally administering a bioactive agent encapsulated in one or more biocompatible polymer or copolymer excipients, preferably, a biodegradable polymer or copolymer, affording microcapsules which due to the proper size of the resultant microcapsules results in the agent reaching and being taken up by the folliculi lymphatic aggregati, otherwise known as the "Peyer's patch," or "GALT" of the animal without loss of effectiveness due to the agent having passed through the gastrointestinal tract. Similar folliculi lymphatic aggregati can be found in the bronchei tubes (BALT) and the large intestine. The above-described tissues are referred to in general as mucosally associated lymphoreticular tissues (MALT). For absorption through mucosal surfaces, compositions and methods of administering at least one anti-IL-6 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695).

Transdermal Formulations and Administration

For transdermal administration, the at least one anti-IL-6 antibody is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599).

Prolonged Administration and Formulations

It can be desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the compounds of the present invention or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

Indications

Rheumatoid Arthritis (RA)

Rheumatoid arthritis (RA) is a chronic systemic inflammatory disease with autoimmune features. A number of the features of RA may be explained through an action of dysregulated IL-6.

IL-6 actions of potential relevance in RA include induction of polyclonal hypergammaglobulinemia and autoantibody production (rheumatoid factor), through the actions of IL-6 as a B cell differentiation factor; the promotion of cytotoxic T cell development, in concert with IL-2; the production of acute phase proteins (CRP, SAA, fibrinogen), through hepatocyte stimulating activity; osteoclast activation, leading to periarticular osteoporosis and bone destruction; the induction of thrombocytosis, through action as megakaryocyte differentiation factor; and regulation of VEGF, and therefore potentially angiogenesis, in concert with IL-1β and TNFα.

IL-6 is produced by RA synovial fibroblasts stimulated by TNFα or IL-1, and is present at high concentration in both synovial fluid (SF) and serum in RA. Correlations exist between serum levels and clinical/laboratory indices of disease activity.

Anti-IL-6/IL-6R mAbs were studied in several clinical studies in patients with active RA. Results to date are briefly described below.

Phase I/II studies

In the first of these studies, a murine anti-IL-6 mAb (BE-8) was administered daily for 10 consecutive days in 5 patients with RA and was associated with transitory clinical and laboratory improvement (9) (Wendling, D; et al. 1993 *J. Rheumatol.* 20:259). The humanized anti-IL-6R (80 kDa) mAb (MRA; Chugai) was tested in several phase I/II studies in patients with RA. In the first of these, MRA was administered by IV infusion at doses of 1-50 mg once or twice a week, with maintenance treatment of 50 mg per week for up to 6 months. This resulted in rapid decreases in the acute phase measures, C-reactive protein (CRP) and fibrinogen, and in low-grade fever, fatigue, and clinical scores, such as morning stiffness and swollen and tender joint counts. Also noted were improvements in anemia, thrombocytosis and hypergammaglobulinemia. In a subsequent study, 45 patients were treated with a single IV infusion of MRA at a dose of 0.1-10 mg/kg, and resulted in trends of improvement in clinical scores at higher dose levels, plus reductions in acute phase reactants.

Phase II studies

In the first of these studies, 15 patients were treated with MRA (dose levels 2, 4 or 8 mg/kg biweekly for 24 weeks), and showed ACR20 responses in 13/15 at week 24, with normalization of CRP/Serum Amyloid A (SAA). Although there were no major acute safety concerns, up to two thirds of patients showed markedly increased LDL cholesterol levels. In a second phase II study, 164 patents with RA resistant to DMARDs were treated with placebo or MRA by IV infusion (dose levels 4 or 8 mg/kg, given every 4 weeks for 3 months), and showed ACR20 response rates at week 12 of 11%, 57%, and 78% for placebo, 4 and 8 mg/kg, respectively. Finally, 359 patients with active RA received MTX alone (10-25 mg/week), MRA alone (dose levels 2, 4 or 8 mg/kg, administered monthly by IV infusion) or MTX plus MRA. MRA and MRA+MTX were more effective than MTX alone, as determined by ACR20 response.

Systemic Lupus Erythematosus (SLE)

SLE is a chronic, potentially fatal, autoimmune disease with multiple protean manifestations. The etiology is unknown. One hallmark of the disease involves B cell hyper-proliferation, activation, and autoantibody production against a variety of self-antigens.

IL-6 induces B cells to differentiate into antibody forming cells. In SLE, there is increased production of autoantibodies (ANA, anti-dsDNA) by these antibody forming cells and immune complex deposition. IL-6 promotes cytotoxic T cell development, increases hepatic acute phase reactants, mesangial cell proliferation, keratinocyte growth, megakaryocytic differentiation and thrombosis.

IL-6 levels are elevated in both SLE patients and murine SLE models. It was demonstrated that IL-6 receptor binding on B cells induces terminal differentiation of B cells into autoantibody producing cells. Linker-Israeli et al. (Linker-Israeli M et al., 1991 *J Immunol* 147: 117-123) have shown decreases in spontaneous polyclonal antibody production when neutralizing antibodies against IL-6 were used. Kitani and others (Kitani A, et al., 1992 *Clin Exp Immunol* 88: 75-83) supported these findings by demonstrating that in vitro T cell production of IL-6 doubled in SLE cultures and that SLE B cells had five fold more IL-6 production than control B cells. However, the pathologic production of autoantibodies in SLE is not solely limited to the effects of IL-6. The role of the IL-6 receptor has been studied also. Nagafuchi and others showed IL-6 receptor up regulation in the majority of SLE B cells vs. normal B cells. Anti-IL-6 receptor antibody inhibited terminal differentiation of these B cells into antibody forming cells. The role of the soluble IL-6 receptor in SLE has yet to be determined.

Type II Diabetes Mellitus (T2DM)

Insulin resistance (impaired insulin action) and impaired β-cell function (functional deficit of pancreatic β-cells to secrete insulin) are considered to be the main causes of T2DM development. Insulin resistance is manifested as an inability of peripheral tissues to respond adequately to insulin challenge, thus causing an increase in blood glucose levels. The increase in insulin resistance and blood glucose levels is followed by compensatory hyper-secretion of insulin by pancreatic β-cells in the early stages of the disease. As T2DM progresses, the ability of β-cells to secrete insulin deteriorates.

The underlining mechanisms responsible for the development of insulin resistance are unclear. The one condition most commonly associated with the development of T2DM is obesity and even a modest weight loss significantly improves glucose levels in patients with T2DM.

Both obesity and insulin resistance/hyperinsulinemia, in combination with dyslipidemia, impaired glucose tolerance and hypertension characterized the condition called Metabolic Syndrome. The natural progression of Metabolic Syndrome to T2DM predisposes individuals to development of micro- and macro-vascular changes that may lead to cardiovascular (CV) disease and ultimately death. Obesity, insulin resistance, and hyper-insulinemia have been suggested to be the most likely links between T2DM and CV disease.

Adipose tissue has been identified as one of the major organs that regulates metabolism, being both an energy storage depot and endocrine organ that secretes numerous molecules involved in insulin sensitivity regulation. In addition to leptin, resistin, adiponectin, and TNFα, adipose tissue secretes IL-6, which has been suggested to represent the link between obesity, inflammation, T2DM and cardiovascular (CV) disease.

A positive correlation between adiposity and IL-6 levels has been documented. It is possible that increased adipose tissue in obesity may provide sustained increases in circulating IL-6 that could decrease insulin sensitivity by promoting inflammation in insulin-responsive tissues or cause insulin resistance by interfering with activity and expression of proteins involved in the insulin-signaling cascade. Both in vitro and in vivo data that support or oppose the potential role of IL-6 in the development of insulin resistance exist.

In vitro data using well-defined cell systems including liver (HepG2)(44), fat (3T3L1) or isolated rat pancreatic islet cells show a direct negative effect of IL-6 on insulin signaling, glucose uptake and insulin secretion, respectively. On the other hand, data obtained from experiments done on skeletal muscle biopsies suggest that IL-6 may increase glucose uptake in exercising muscle.

In vivo data on the association between IL-6 levels and insulin sensitivity are equally mixed. Models of IL-6 over-expression or complete ablation suggest that complete inhibition of IL-6 activity might not have a beneficial effect. For example, in transgenic non-obese diabetic (NOD) mice, over-expression of human IL-6 delays the onset of diabetes and prolongs survival. In addition, data from IL-6 null mice suggest that IL-6 may play a role in energy balance regulation since these animals develop late-onset obesity and higher glucose levels.

In humans, a naturally occurring mutation within the region of the IL-6 promoter leads to an increase in IL-6 secretion rate. This mutation has been associated with both an increase and a decrease in insulin sensitivity.

In another set of experiments, the effect of exogenous IL-6 has been evaluated. In normal subjects, IL-6 administration led to increases in glucose levels without affecting plasma insulin concentrations, whereas, in cancer patients, addition of IL-6 increased glucose disposal. In addition, the correlation between IL-6 levels and insulin resistance has been examined. Data from these experiments suggested that in both men and women, higher circulating levels of IL-6 were correlated with higher insulin resistance although a cause-and-effect relationship remains to be determined.

IL-6 has been indicated to play an important role in the development of obesity-associated insulin resistance. However, conflicting in vitro and in vivo data exist that both support or oppose its potential role in insulin resistance.

Osteoarthritis (OA)

OA is a chronic, degenerative joint disorder, characterized by loss of articular cartilage, and related changes in subchondral bone. Although varying degrees of inflammation are observed on arthroscopy or in synovial biopsy specimens, the disease is not primarily inflammatory. Rather, it is thought to originate from changes in chondrocyte and/or osteoblast metabolism. TNF, IL-1 and IL-6 are the cytokines most strongly associated with these changes.

IL-6 is detectable in synovial fluid from patients with OA, although at levels substantially below those seen in inflammatory arthropathies (Bertazzolo, N. et al. 1994 *Agents and Actions* 41: 90-92). IL-6 is recognized to be a primary stimulus for hepatic acute phase protein synthesis, and CRP levels are associated with the presence of knee OA, even after taking into account the known association between CRP and obesity (Mohtai, M. et al. 1996 *J Orthopedic Research* 14: 67-73).

IL-6 is expressed in chondrocytes from OA cartilage, but not normal cartilage (Sowers, M. et al. 2002 *Osteoarthritis and Cartilage* 10: 595-601). In experiments testing the effects of mechanical stress on chondrocyte cytokine expression in vitro, fluid induced shear stress markedly upregulated IL-6 mRNA and protein. This suggests that IL-6 expression in OA cartilage may result from mechanical loading. IL-6 may also be produced in response to IL-1 action on chondrocytes (Dozin, B. et al. 2002 *Matrix Biology* 21: 449-459).

In other experiments, IL-6, in combination with sIL-6R, led to inhibition of proteoglycan synthesis by human articular chondrocytes cultured ex vivo, although the effect was modest compared with IL-1 (Guerne, P. et al. 1999 *Matrix Biology* 18: 253-260).

Chronic Obstructive Pulmonary Disease (COPD)

COPD is a disease state characterized by airflow limitation that is not fully reversible. The airflow limitation is usually progressive and associated with abnormal inflammatory response of the lungs to noxious particles and gases (Pauwels R A et al. 2001 *Am. J. Respir Crit Care Med* 163:1256-1276). COPD is characterized by acceleration in the normal decline in lung function seen with aging. The slowly progressive airflow limitation leads to disability and premature death. COPD is a leading cause of death and disability, but has only recently been extensively explored from a cellular and molecular perspective (Barnes P. J. et al. 2003 *Eur Respir J* 22:672-688). In COPD, there is a chronic inflammation that leads to fixed narrowing of small airways and alveolar destruction (emphysema). The inflammatory response is characterized by an increased number of alveolar macrophages, neutrophils and cytotoxic T-lymphocytes and the release of multiple inflammatory mediators (chemokines, cytokines, growth factors and lipids). A high level of oxidative stress may amplify the inflammation. There is also increased elastolysis and evidence for involvement of several elastolytic enzymes. The inflammation and proteolysis in COPD is an amplification of the normal inflammatory response to cigarette smoke. In contrast to asthma, the inflammation appears to be resistant to corticosteroids (Barnes P. J. et al. 2003).

In animal models, bacterial endotoxin or lipopolysaccharides (LPS) and cigarette smoke exposure induce neutrophilia and increased production of IL-6 in the bronchioalveolar lavage (BAL) fluid (Underwood D. C. et al. 2000 *AJPLCMP* 279:L895-902). Over-expression of IL-6 in mouse lungs induces emphysema (Kuhn III Ch. et al. 2000 *AJRCMB* 22:289-295). In humans, forced expiratory volume in one second (FEV1) is inversely correlated with IL-6, IL-8 levels and polymorphonuclear cell counts in the BAL (Soler N. et al. 1999 *Eur Respir J* 14:1015-1022). Plasma TNFα, IL-6 and CRP levels are increased in subjects with mild to severe COPD (Yasuda N. et al. 1998 *Respir Med* 92:993-999).

Acute exacerbation of COPD is defined as sustained worsening of the patient's condition, from the stable state and beyond normal day-to-day variations, that is acute in onset and necessitates a change in regular medication (Burge S. et al. 2003 *Eur Respir J* 21: Suppl. 41, 46s-53s). Although increased symptoms and worsening of lung function are a common cause of hospital admission (approximately 500,000 each year in the US), the underlying cellular and molecular mechanisms have not been widely investigated and are poorly understood (Wedzicha, J. A. 2002 *Chest* 121: 136S-141S). Acute exacerbations may be prolonged and have profound effect on quality of life and may accelerate the progression of COPD (Soto F. J. et al. 2003 *Pulm Med* 9:117-124). Respiratory infections are the most common causes of COPD exacerbations. The majority of these infections are caused by bacteria, but many of them are due to viral infections, particularly rhinovirus (Soto F. J. et al. 2003). Environmental factors, air pollutants and temperature may also play a role.

During exacerbation, there is an increase in neutrophils and concentrations of IL-6, IL-8, TNFα and LTB4 in sputum of patients with COPD. Some patients with moderate-to-severe COPD are prone to frequent exacerbations (three or more exacerbations per year). This group of patients ("frequent exacerbators") has a higher level of IL-6 and a lower level of secretory leukocyte protease inhibitor even when COPD is stable (Bhowmik A. et al. 2000 *Thorax* 55: 114-120; Gompertz S. et al. 2001 *Thorax* 56: 36-41; Gompertz S. et al. 2001 *Eur Respir J* 17: 1112-1119).

A number of other mechanisms, such as oxidative stress and bacterial colonization, have been implicated in the pathophysiology of COPD exacerbation as well.

Example 1

Cloning and Expression of IL-6 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors, such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Suitable mammalian and other host cells include human Hela, 293, H9 and Jurkat cells, mouse NIH3T3 and C127 cells, Cos 1, Cos 7 and CV 1, quail QC1-3 cells, mouse L cells and Chinese hamster ovary (CHO) cells. Alternatively, the gene can be expressed in stable cell lines that contain the gene integrated into a chromosome. The co-transfection with a selectable marker, such as dhfr, gpt, neomycin, or hygromycin, allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10: 169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Mol. Cell. Biol. 5:438-447 (1985)) plus a fragment of the CMV-enhancer (Boshart, et al., Cell 41:521-530 (1985)).

Multiple cloning sites, e.g., with the restriction enzyme cleavage sites BamHI, XbaI and Asp718, facilitate the cloning of the gene of interest. The vectors contain in addition to the 3' intron, the polyadenylation and termination signal of the rat preproinsulin gene.

Cloning and Expression in CHO Cells.

The vector pC4 can be used for the expression of IL-6 antibody. Plasmid pC4 is a derivative of the plasmid pSV2-dhfr (ATCC Accession No. 37146). The plasmid contains the mouse DHFR gene under control of the SV40 early promoter. Chinese hamster ovary or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

High efficiency promoters other than the strong promoter of the long terminal repeat (LTR) of the Rous Sarcoma Virus can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the IL-6 antibody in a regulated way in mammalian cells (M. Gossen, and H. Bujard, Proc. Natl. Acad. Sci. USA 89: 5547-5551 (1992)). For the polyadenylation of the mRNA, other signals, e.g., from the human growth hormone or globin genes, can be used as well. Stable cell lines carrying a gene of interest integrated into the chromosomes can also be selected upon co-transfection with a selectable marker, such as gpt, G418 or hygromycin. It is advantageous to use more than one selectable marker in the beginning, e.g., G418 plus methotrexate. The plasmid pC4 is digested with restriction enzymes and then dephosphorylated using calf intestinal phosphatase by procedures known in the art. The vector is then isolated from a 1% agarose gel.

The DNA sequence encoding the complete IL-6 antibody is used, e.g., as presented in SEQ ID NOS: 98 and 96, corresponding to HC and LC variable regions of an IL-6 antibody of the present invention, respectively, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 micrograms of the expression plasmid pC4 are cotransfected with 0.5 microgram of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 microgram/ml G418. After 2 days, the cells are trypsinized and seeded in hybridoma cloning plates (Greiner, Germany) in alpha minus MEM supplemented with 10, 25, or 50 ng/ml of methotrexate plus 1 microgram/ml G418. After about 10-14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Example 2

Construction and Screening of Anti-IL-6 Antibodies

Variants of the IL-6 antibody (clone AME-A9) were constructed and screened for activity. In this example and otherwise herein, the CDRs are as defined by Kabat with the exception of CDRH1 which is the sum of Kabat and Chothia definitions. The length of CDRH2 made it necessary to construct two separate libraries to cover the entire region. Clones of interest were sequenced and further characterized by ELISA and in a cell based assay and kinetic constants were determined.

Figure 9:
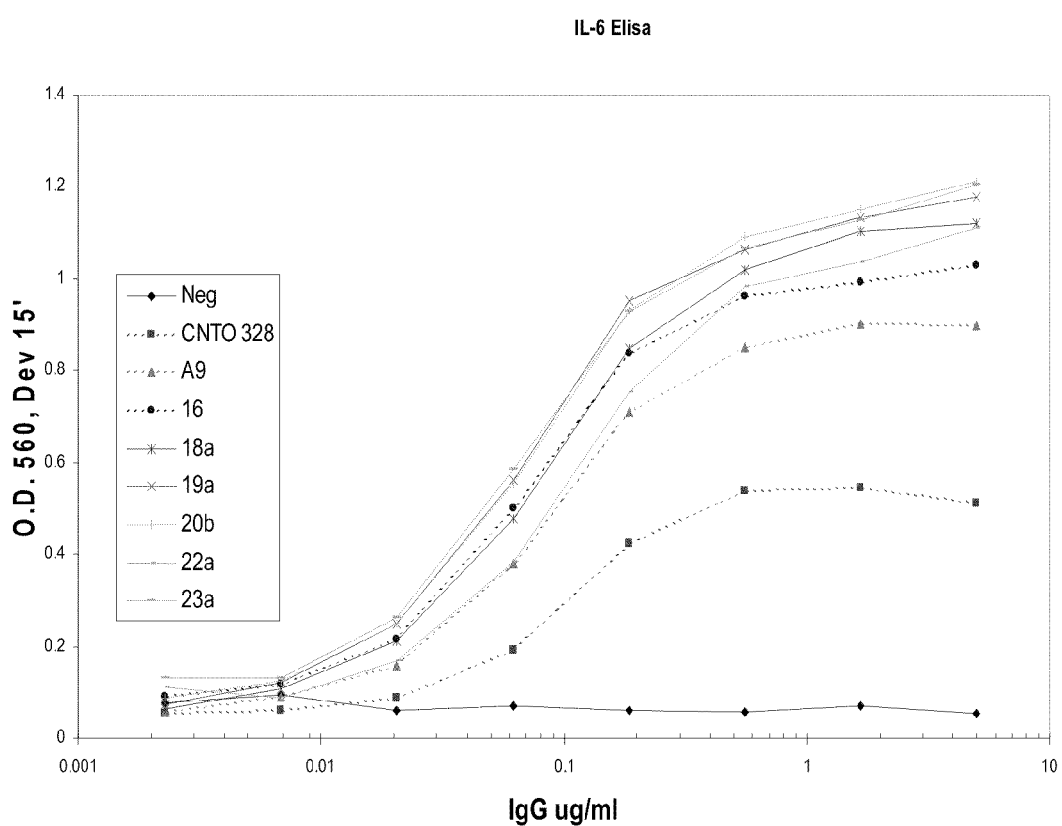
FIG. 9 shows the results of the ELISA binding assay described in Example 3.

An example of an ELISA done with the purified IgGs is shown in FIG. 9. The ELISA generally used Costar 3366 microtiter plates coated with a goat anti-human kappa antibody. Dilutions of Fab (or IgG) were incubated in the coated wells for 1 hr at 22° C. The wells were then washed with PBS, 0.1% Tween 20 and biotinylated IL-6 at 200 ng/ml was added for 1 hour. After washing, an alkaline phosphatase conjugate of NeutrAvidin was added and incubated for 1 hour at 22° C. A colorimetric substrate was added after extensive washing and the bound IL-6 was determined. A variation of this ELISA included an extended wash step in a beaker of PBS, 0.01% BSA at 37° C. after the biotinylated IL-6 incubation, e.g., an 18 hour extended wash step.

Several of the generated human engineered IL-6 reactive IgG monoclonal antibodies of the invention have affinity constants between $1 \times 10^9$ and $9 \times 10^{12}$. The high affinities of these human engineered monoclonal antibodies make them suitable for therapeutic applications in IL-6-dependent diseases, pathologies or related conditions.

Multiple different human engineered anti-IL-6 antibody variants were obtained by altering one or more of the CDR regions of the antibody. Table 3 below shows a summary of the beneficial mutations that were found in the individual CDR libraries (amino acid changes are relative to the AME-A9 variant). In addition, Table 13 below shows the amino acid sequences for the light and heavy chain CDRs with the possible substitution positions (marked as "X").

A "combinatorial" library was constructed based on the best clones (i.e., variants) found in the individual CDR libraries. Table 4 lists the mutations that were included in the "combinatorial" library. The combinatorial library was screened and characterized as described above. The mutations found in six of the better clones are shown in Table 5A below, while the sequence ID numbers for the CDRs in these clones are shown in Table 5B.

Assaying Anti-IL-6 IgGs in a Cell-Based Assay

The chimeric anti-IL-6 and human engineered anti-IL-6 (clone AME-19a) antibodies were tested for the ability to prevent the growth of an IL-6 dependent cell line. 7TD1 cells were plated into a Costar 3610 96 well plate at 200 cells per well. Antibodies, diluted in IMDM media, were added to the wells followed by the addition of human IL-6 to a final concentration of 500 pg/ml and plates were incubated in a tissue culture incubator for 64-72 hours. At that time, 50 µl of cell lysis buffer from the ATPlite kit (Packard Bioscience) were added to all wells and the plates were agitated for 3 minutes. 50 µl of ATPlite substrate were added and the covered plates were shaken for 1 minute. Chemiluminescence was determined on a luminometer.

Figure 10:
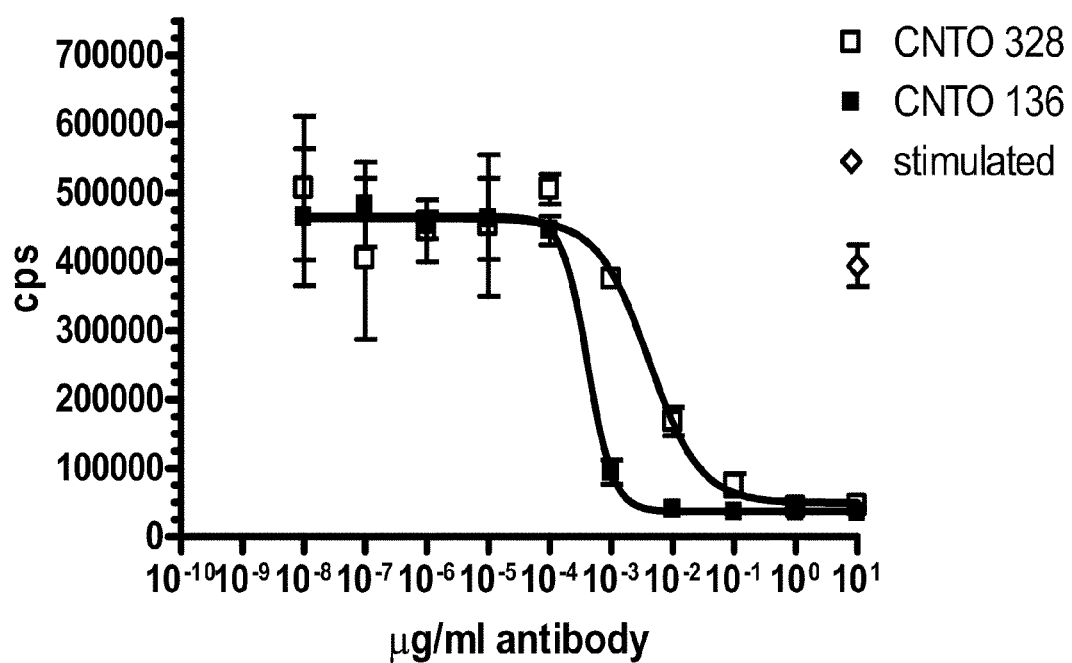
FIG. 10 shows the results of an anti-proliferation assay using the IL-6 dependent cell line described in Example 3.

The results of a cell-based assay are shown in FIG. 10, with the calculated $EC_{50}$ values shown in Table 6 below. The $EC_{50}$ value of the chimeric anti-IL-6 antibody is $2.7 \times 10^{-11}$ M (4.09 ng/ml) and that of the human engineered anti-IL-6 (clone AME-19a) antibody is $2.7 \times 10^{-12}$ M (0.41 ng/ml). The $EC_{50}$ value of the human engineered antibody shows about a 10-fold improvement, although it may be possible to obtain from about a 10-fold up to about a 60-fold improvement, including intervening values, in the $EC_{50}$ value.

Example 3

Binding Kinetics of Human Engineered Anti-Human IL-6 Antibodies

ELISA analysis confirms that purified antibody from these host cells bind IL-6 in a concentration-dependent manner. In this case, the affinity of the antibody for its cognate antigen (epitope) is measured. Quantitative binding constants are obtained using BIAcore analysis and the KinExA 3000 instrument. The results indicate that several of the human engineered monoclonal antibodies are very high affinity with $K_D$ in the range of $1 \times 10^{-9}$ to $3 \times 10^{-14}$.

An enzyme immunoassay (EIA) that uses anti-human IL-6 monoclonal antibodies (AME-A9, AME-A16, AME-18a, AME-20b, AME-22a, and AME-23a) and CNTO 328 used as a positive control to detect the bound IL-6 to the soluble IL-6 receptor, sIL-6R, was performed. The soluble human IL-6 receptor, sIL-6R, and recombinant human IL-6 were obtained from R&D Systems (Minneapolis, Minn.) (Catalog #227-SR-025 and 206-IL-010, respectively). Goat anti-human IgG-horseradish peroxidase-linked (H+L chain) was obtained from Jackson Immunoresearch (West Grove, Pa.) (Catalog #109-035-003). Hydrogen Peroxide and OPD tablets were obtained from Sigma (St. Louis, Mo.) (Catalog #H-1009 and P-8287, respectively).

Enzyme Linked Immunoassay for sgp80/IL-6/Anti-IL-6 mAb Complex Formation

Costar EIA plates (Corning/Costar, Acton, Mass.) (Catalog #9018) were coated with sIL-6R (10 µg/ml in PBS, 100 µl/well) overnight at 4° C. The plates were washed with 0.15M saline containing 0.02% (v/v) Tween 20 and wells were blocked with 1% (w/v) BSA in PBS, 200 µl/well for one hour at room temperature. The wells were washed again then in the sequential format incubated with 200 ng/ml human IL-6 (100 µl/well) in PBS for one hour at room temperature. Antibody was added to all wells in 10-fold serial dilutions from a starting concentration of 10 µg/ml in 100 µl/well for one hour at room temperature. After washing, the wells were incubated with goat anti-human IgG (H+L)-HRP-linked, (10 µg/ml in PBS) for 30 minutes at room temperature. The wells were washed and 100 µl/well of citrate-phosphate substrates solution (0.1M Citric Acid and 0.2M Sodium Phosphate, 0.01% $H_2O_2$ and 1 mg/ml OPD) was added for 15 minutes at room temperature. The reaction was stopped by addition of 25 µl/well of 4N sulfuric acid and the $OD_{490}$ was read via an automated ELISA plate reader (Molecular Devices Spectromax Plus, Sunnyvale, Calif.).

To test the effect of preincubation of IL-6 with anti hIL-6 monoclonal antibodies or CNTO 328, 200 ng/ml IL-6 (100 µl) was incubated with ten-fold serial dilutions of antibody (100 µl), starting with 10 µg/ml for one hour at room temperature. This pre-incubated mixture was then incubated with sIL-6R for one hour at room temperature and detection of the sIL-6R/IL-6/anti human IL-6 complex was detected using goat anti-human IgG (H+L)-HRP-linked, (10 µg/ml in PBS) for 30 minutes at room temperature. The remainder of the assay conditions was the same as described in the previous paragraph.

Previous studies have shown that CNTO 328 can detect IL-6 when it is captured by sIL-6R that is coated on an EIA plate internal technical report. In addition, AME-A9, AME-A16, AME-18a, AME-20b, AME-22a, and AME-23a can detect IL-6 bound to sgp80 (sIL-6R) in a dose dependent manner using EIA. Each human engineered anti-IL-6 antibody was evaluated in reference to CNTO 328. However, preincubation of IL-6 and any of these anti hIL-6 monoclonal antibodies precludes the ability of sIL-6R to bind IL-6.

Measuring Kinetic Constants for Anti-IL-6 IgGs

The KinExA 3000 instrument, manufactured by Sapidyne, was used to measure binding kinetics. Briefly, human IL-6 was covalently coupled to azlactone beads and the binding of free IgG to the beads was detected on the instrument. To measure $K_D$, individual tubes containing a constant concentration of either 0.5, 1 or 5 pM of IgG with decreasing serially diluted human IL-6, were incubated for 3-4 days at 20° C. in 0.1% BSA, PBS. A total of 13 tubes were used for each $K_D$ determination. For example, the chimeric anti-IL-6 antibody was used at a constant concentration of 5 pM and individual tubes were incubated with 0-200 pM of IL-6. Incubations for the other IgGs were set in a similar manner. After the incubation, free IgG in each equilibrated sample was determined on the KinExA 3000 instrument according to the manufacturer's instructions. $K_D$ values were determined by the KinExA 3000 software using the KinExA 3000 instrument, as described in more detail below.

To measure $k_{on}$, individual IgGs at 200 pM were mixed with 100-200 pM of human IL-6 and the unbound IgG was detected by binding to human IL-6 covalently coupled to azlactone beads on the KinExA 3000 instrument. A series of measurements were taken over time. The resulting data was used to calculate the $k_{on}$ with the KinExA 3000 software. $k_{off}$ was calculated by using the formula $K_D = k_{off}/k_{on}$. A summary of the kinetic constants for the anti-IL-6 IgGs is shown in Table 7.

Example 4

In Vitro Characterization of Anti-IL-6 Antibody

In vitro studies were conducted to characterize the sequence, epitope specificity, affinity, and biologic activity of the anti-IL-6 antibody.

Human Engineered mAb

Sequence analysis confirms that the anti-IL-6 antibody of the present invention (embodied in different variants/clones) contains fully human frameworks. Table 5a shows a total of 10 amino acid residues changed in both the heavy and light chains of CDR1, 2, and 3 in the anti-IL-6 antibody of the present invention (in different variants of the antibody) as compared with the chimeric anti-IL-6 antibody (described in PCT WO 04/039826).

Epitope Specificity

The anti-IL-6 antibody of the present invention and the chimeric anti-IL-6 antibody recognize a similar epitope on human IL-6. These antibodies do not compete with the commercial mouse anti-human IL-6 mAb from R&D Systems #MAB-206 suggesting that they recognize an epitope that is uniquely different from that of the R&D anti-IL-6 mAb. The anti-IL-6 antibody of the present invention and the chimeric anti-IL-6 antibody do not compete with R&D rat anti-human IL-6 mAb.

Human IL-6 (200 ng/ml) was captured by plate-bound anti-IL-6 mAb (mouse anti-human IL-6 mAb, MAB-206, which was used only as plate bound mAb to capture human IL-6) (10 µg/ml) and serial dilutions of the anti-IL-6 antibody of the present invention and the chimeric anti-IL-6 antibody, as indicated along the X-axis were then added to the plate. Binding to IL-6 was measured as increase in $OD_{490}$ along the Y-axis. Both the anti-IL-6 antibody of the present invention and the chimeric anti-IL-6 antibody show dose-dependent binding to IL-6.

Conversely, the anti-IL-6 antibody of the present invention and the chimeric anti-IL-6 antibody competitively bind for human IL-6, suggesting that the two molecules share a similar binding epitope on IL-6. Human IL-6 (200 ng/ml) was captured by plate-bound MAB-206 (10 µg/ml). Serial dilutions of the anti-IL-6 antibody of the present invention as indicated along the X-axis and 50 ng/ml of biotinylated chimeric anti-IL-6 antibody were then added to the plate. Binding of biotinylated chimeric anti-IL-6 antibody to IL-6 was detected by streptavidin-HRP and measured as $OD_{490}$ readings along the Y-axis.

Moreover, the human engineered and chimeric antibodies exhibit similar properties for binding to the sIL-6/sIL-6R complex (FIG. 1). The anti-IL-6 antibody of the present invention binds to sIL-6/SIL-6R complex. Soluble IL-6 receptor (sIL-6R) was coated on the plate at 10 µg/ml concentration. Human IL-6 was then added to the plate at 200 ng/ml concentration. Serial dilutions of the anti-IL-6 antibody of the present invention or the chimeric anti-IL-6 antibody, as indicated along the X-axis, were then added to the plate and binding to the IL-6/sIL-6R complex was detected using HRP-anti-human IgG and measured as $OD_{490}$ readings along the Y-axis.

To further confirm the above findings, cross-species reactivity testing was conducted using IL-6-containing conditional supernatant generated from LPS and IFNγ-stimulated PBMCs of different species in a 7TD1 (IL-6 dependent murine hybridoma cell line) cell-based proliferation assay. The human engineered antibody of the invention was shown to neutralize the activity of the conditioned supernatants in stimulating 7TD1 cell proliferation from a variety of primate species, including human, marmoset, cynomolgus monkey, chimpanzee, rhesus monkey, baboon, pigtail monkey, and cotton top monkey, and displayed a similar cross-species reactivity pattern compared with the chimeric antibody (Table 8).

Figure 3:
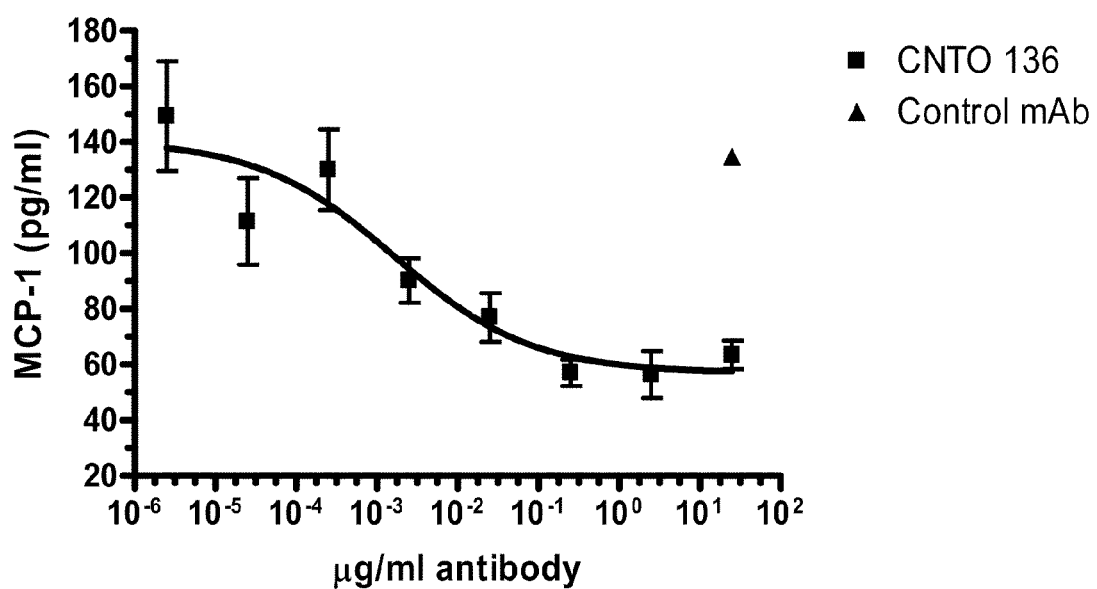
FIG. 3 demonstrates that human engineered anti-IL-6 antibody inhibits IL-6 stimulated MCP-1 secretion from U937 cells as measured by ELISA.

Finally, when epitope mapping was conducted using the tryptic digest method, the same binding epitope for the human engineered and chimeric antibodies on human IL-6 was observed and is located on the Helix D spanning amino acid residues 168-184 (FIG. 3). Recent mutational analysis confirmed that residues 179 and 182 are essential for the antibody of the invention to bind to IL-6. The epitope (amino acid residues 168-184) was identified as the surface of IL-6 that retained deuterium in the presence of human engineered anti-IL-6 antibody.

Biologic Activity

The IL-6 neutralization potency of human engineered anti-IL-6 antibody was determined by 7TD1 cell-based bioassay. Human engineered anti-IL-6 antibody demonstrated a 10-fold higher neutralization potency as compared with chimeric anti-IL-6 antibody in the 7TD1 cell proliferation assay. 7TD1 cells were stimulated with 500 pg/ml of hIL-6 in the presence of serial dilutions of human engineered anti-IL-6 antibody or chimeric anti-IL-6 antibody or isotype control mAb for 72 hours. Cell proliferation was measured as counts per second as indicated on the Y-axis. Error bars indicate the SD of duplicate samples. A closed circle indicates cells without IL-6; open circle indicates cells stimulated with 500 pg/ml of hIL-6.

Figure 4:
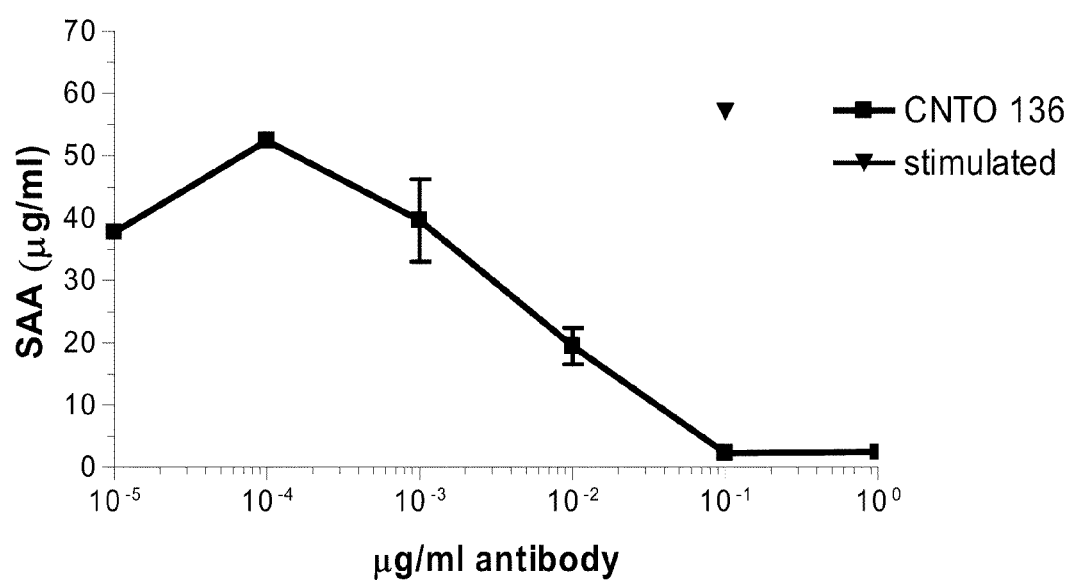
FIG. 4 shows that the human engineered anti-IL-6 antibody inhibits IL-6 and IL-1β stimulated SAA secretion from HepG2 cells as measured by ELISA.

Human engineered anti-IL-6 antibody also inhibits IL-6-induced monocyte chemoattractant protein-1 (MCP-1) production from U937 cells (FIG. 3) and IL-6/IL-1β-induced serum amyloid A (SAA) production from HepG2 human hepatoma cells (FIG. 4). FIG. 3 demonstrates that human engineered anti-IL-6 antibody inhibits IL-6 stimulated MCP-1 secretion from U937 cells. $5 \times 10^5$ cells/well were treated with 1 ng/ml of hIL-6 and serial dilutions of human engineered anti-IL-6 antibody for 72 hours. Cell culture supernatants were analyzed in triplicates by ELISA for the presence of MCP-1.

FIG. 4 shows that the human engineered anti-IL-6 antibody inhibits IL-6 and IL-1β stimulated SAA secretion from HepG2 cells. $2.25 \times 10^5$ cells were stimulated with 100 ng/ml of hIL-6, 200 ng/ml of sIL-6R and 1 ng/ml of IL-1β in the presence of serial dilutions of human engineered anti-IL-6 antibody for 24 hours. Cell culture supernatants were then analyzed in duplicates by ELISA for the presence of SAA.

IL-6 Dependent Stat3 Phosphorylation

To assess the ability of human engineered anti-IL-6 antibody to block the signaling cascade resulting from IL-6 binding to IL-6R and gp130, an immuno-precipitation assay was performed to test the effect on IL-6 dependent STAT3 phosphorylation in THP-1 cells, which express gp130 on the cell surface.

The mAbs are sterile-filtered filter-sterilized and stored in PBS at 4° C. Recombinant human IL-6 (206-IL-010) and sIL-6R (227-SR-025) from R&D Systems (Minneapolis, Minn.) were used. RPMI media (11875-085), heat-inactivated fetal bovine serum (16000-069), L-Glutamine (25030-081), non-essential amino acids (11140-050), and sodium pyruvate (11360-070) were obtained from Invitrogen (Carlsbad, Calif.). TBS (10 mM Tris, pH7.5, 100 mM NaCl) was also used.

THP-1, a human acute monocytic leukemia cell line received from research cell banks, was tested to be mycoplasma negative and bacteria free. These cells were cultured in RPMI media containing 10% fetal bovine serum, 2 mM glutamine, and 1 mM sodium pyruvate. Cells were subcultured or harvested when cultures reached approximately 85% confluence. Cells were routinely split 1:5 every three days.

For tyrosine phosphorylation, cells were grown to 80-90% confluence in T-225 flasks. The media was removed and replaced with fresh media without serum and incubated for overnight. Following serum starvation, cells were harvested from each flask, pelleted and a final concentration of $20 \times 10^6$ cells per condition was resuspended in 0.5 ml media without serum.

RhIL-6 (0.1 µg/ml) was pre-incubated at 37° C. for 15 minutes with the following reagents: 0.5 ml media alone, anti-IL-6 Ab (10 µg/ml); and sIL-6R (0.2 µg/ml). SIL-6R (0.2 µg/ml) and anti-IL-6 Ab (10 µg/ml) were then added to cells preincubated with anti-IL-6 Ab and sIL-6R, respectively, for incubation at 37° C. for 15 minutes. The cells were then combined with medium as negative control and the IL-6/Ab/sIL-6R complex and incubated at 37° C. for 6 minutes. The cells were washed twice in ice-cold TBS and cell pellets were either processed as described in Section 5.4 or stored at −70° C.

For immunoprecipitation, the cell pellets were lysed in 1 ml lysis buffer (50 mM Tris, pH7.5, 300 mM NaCl, 0.5% Triton-X-100) (T-9284, Sigma, St. Louis, Mo.) containing complete protease inhibitor cocktail tablet (1697498, Roche, Basel, Switzerland). The cells were vortexed for 30 seconds and incubated at −70° C. for 20-60 minutes. Cellular debris was removed by centrifugation at 13,000 rpm for 20 minutes. To reduce non-specific background staining, the samples were pre-cleared by incubation with 2 µg rabbit IgG (15006, Sigma, St. Louis, Mo.) plus 50 µl Protein A agarose (SC-2001, Santa Cruz Biotechnology, Santa Cruz, Calif.) for 1 hr at 4° C. on an orbital mixer. The agarose beads were removed by centrifugation at 2500 rpm for 5 minutes. The cleared lysates were transferred to microcentrifuge tubes and incubated with anti-STAT3 (2 µg/ml) (SC-7179, Santa Cruz Biotechnology) overnight at 4° C. on an orbital mixer, followed by addition of 50µ Protein A agarose beads and incubated for 2 hours at 4° C. on an orbital shaker. The agarose beads were collected by centrifugation at 2500 rpm for 5 minutes and washed 5 times in ice-cold TBS at 4° C. The agarose beads were then resuspended in 40 µl Laemmli sample buffer plus DTT (NP0007-465030, Invitrogen, Carlsbad, Calif.) and heated at 95° C. for 5 minutes.

The samples were resolved on a 3-8% NuPage Bis-Tris gel (EA0375BOX, Invitrogen, Carlsbad, Calif.) with running buffer (NP0002-465026, Invitrogen, Carlsbad, Calif.) at 100 V for 1 hour. The proteins were transferred to a Nitrocellulose membrane (LC2001, Invitrogen, Carlsbad, Calif.) using transfer buffer (NP0006-465029, Invitrogen, Carlsbad, Calif.) at 30 V for 1 hour. The membranes were blocked in 10% fat free dry milk (Nestle, Glendale, Calif.) in TBS-T for overnight at 4° C. Following several washes in TBS-T at room temperature, the membranes were incubated with mouse monoclonal anti-p-STAT3 Ab (SC-8059, Santa Cruz Biotechnology, Santa Cruz, Calif.), which was diluted 1:1000 in TBS-T for 4 hrs at 4° C. on an orbital shaker. After several washes, the membranes were then incubated with donkey anti-mouse IgG-HRP (1:1000) (SC-2318, Santa Cruz Biotechnology, Santa Cruz, Calif.) at room temperature for 2 hr on an orbital mixer. After several washes, the samples were detected using ECLplus Western Blot Detection Reagents and analysis kit (RPN2108, Amersham Biosciences, Piscataway, N.J.) following manufacturer's protocol and visualized by exposure to ECL film. The membranes were then stripped of Ab by submerging in 100 mM DTT, 2% SDS, 62.5% mM Tris-HCI, pH 6.7 at 100° C. for 30 minutes with agitation. The membranes were then washed in TBS-T and blocked overnight with the 10% fat free dry milk. The membranes were washed and incubated with anti-STAT3 (1:1000) (SC-7179, Santa Cruz Biotechnology) in TBS-T for 2 hours at 4° C., washed 5 times followed by a 1 hour incubation with goat anti-rabbit IgG-HRP (1:1000) (SC2030, Santa Cruz Biotechnology, Santa Cruz, Calif.) and detected using ECLplus. All membranes were routinely stripped and reprobed with STAT3 to demonstrate the presence of STAT3 protein.

The results showed that human engineered anti-IL-6 antibody blocked IL-6-mediated stat3 phosphorylation, a key component in the IL-6 signaling pathway (FIGS. 5A and 5B). Human engineered anti-IL-6 antibody (AME-19A) inhibits IL-6/sIL-6R-induced stat3 phosphorylation. Recombinant human IL-6/sIL-6R-induced stat3 phosphorylation was detected in THP-1 cells (FIG. 5B). The addition of 10 µg/ml of human engineered anti-IL-6 antibody (AME-19A) or chimeric anti-IL-6 antibody completely inhibited stat3 phosphorylation (FIG. 5B). FIG. 5A shows the presence of a similar amount of unphosphorylated stat3 protein in all samples corresponding to the different human engineered anti-IL-6 clones. As used herein, CNTO328 (or 328) designates the chimeric, human-murine antibody (also referred to as wild type (WT)), 150 designates clone AME-22a, 143 designates clone AME-23a, 140 designates clone AME-20b, 136 designates clone AME-19a, 130 designates clone AME-18a, 106 designates clone AME-A16, 104 designates clone AME-A9.

In Vivo Efficacy of Human Engineered Anti-IL-6 Antibody

The efficacy of human engineered anti-IL-6 antibody was assessed in two different in vivo models. First, the effects of human engineered and chimeric anti-IL-6 antibody were tested and compared in a human IL-6-induced Matrigel angiogenesis assay in mice. 200 ng/ml of human IL-6 was included in the Matrigel plug. Two Matrigel plugs were injected into each nude mouse. Groups of six mice received an i.v. injection of 1, 3, or 6 mg/kg of human engineered or chimeric anti-IL-6 antibody. PBS or an isotype control mAb was also administered for control groups. Plugs were removed on day 7 and angiogenesis was measured by hemoglobin content, microvessel length, and microvessel number in the plugs. Results showed that human IL-6 (PBS group) stimulated angiogenesis in the Matrigel plug model as measured by all three parameters.

Human engineered anti-IL-6 antibody (AME-19A) inhibits the mean number of microvessels in Matrigel plugs. In addition, human engineered anti-IL-6 antibody (AME-19A) inhibits mean length of microvessels in Matrigel plugs. Also, human engineered anti-IL-6 antibody (AME-19A) inhibits hemoglobin level in Matrigel plugs.

In addition, both human engineered (AME-19A) and chimeric anti-IL-6 antibody dose-dependently inhibited IL-6-mediated angiogenesis in nude mice. Finally, human engineered and chimeric anti-IL-6 antibody exhibited comparable activity in inhibiting IL-6-induced angiogenesis at 6 mg/kg, the highest dose tested. Although chimeric anti-IL-6 antibody significantly inhibited human IL-6-induced angiogenesis at 3 mg/kg as measured by vessel length and vessel number, no statistically significant differences were detected between human engineered and chimeric anti-IL-6 antibody at these doses.

Figure 6:
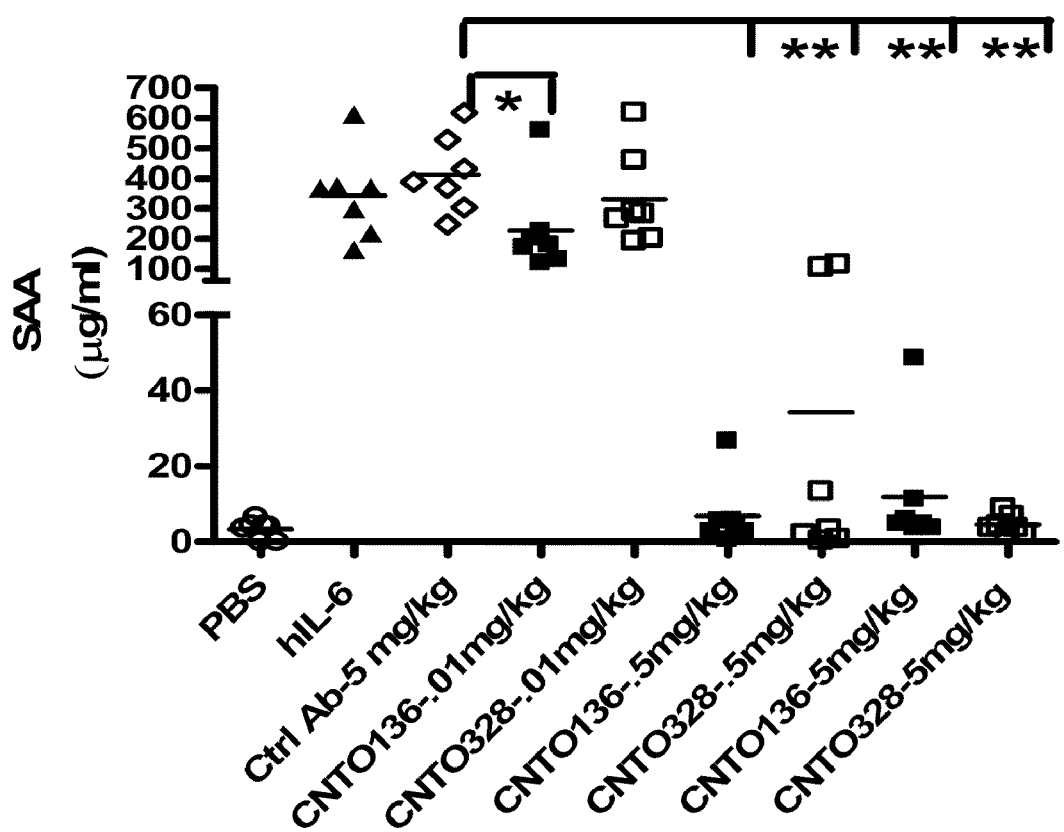
FIG. 6 shows the inhibition by human engineered and chimeric anti-IL-6 antibody of human IL-6-induced SAA production in Balb/C mice.

An additional in vivo model was developed to further evaluate the effect of human engineered anti-IL-6 antibody on human IL-6-induced acute phase reactant, serum amyloid protein A (SAA) production in Balb/C mice. Mice received an i.p. administration of 0.01, 0.5 or 5 mg/kg of human engineered anti-IL-6 antibody 4 hours prior to an i.v. administration of 5 µg/kg of human IL-6 (FIG. 6). PBS and isotype control mAb were used as controls. Serum SAA levels were determined at 16 hours post-IL-6 injection. Both human engineered and chimeric anti-IL-6 antibody significantly inhibited human IL-6-induced SAA production in Balb/C mice at 0.5 and 5 mg/kg, and human engineered anti-IL-6 antibody significantly inhibited SAA production at the lowest dose tested. However, no statistically significant differences were observed between human engineered and chimeric anti-IL-6 antibody at all three doses tested (FIG. 6).

FIG. 6 shows that human engineered anti-IL-6 antibody inhibits human IL-6-induced SAA production. Each point represents the mean value of SAA for each animal and the line represents the mean of all the data points in each group. Pair-wise comparison was conducted and Tukey's 95% simultaneous confidence intervals were used in order to control the overall type I error. (**p<0.001, *p<0.05).

Example 5

Therapeutic Rationale for Anti-IL-6 mAb

Rheumatoid Arthritis. Effect of Anti-IL-6 mAb on Collagen Induced Arthritis (CIA)—an Animal Model of Rheumatoid Arthritis Preclinical In Vivo Disease Models IL-6 has been targeted in a variety of in vivo models. Either rat anti-mouse IL-6 antibody was used in standard murine models or humanized anti-IL-6R (80 kDa) mAb (MRA; Chugai) was used in primate models and in the human/mouse SCID model. In murine collagen induced arthritis (CIA), anti-IL-6 was effective in preventing disease if used early (day 0 or 3 post immunization with collagen), but not at later time points. In the human/mouse SCID transplant model, in which human synovial tissue is transplanted into immunodeficient mice, MRA treatment led to shrinkage of tissue implants and reduced inflammatory cells and osteoclasts. In CIA in cynomolgus monkeys, MRA inhibited development of arthritis, and improved acute phase measures.

The effect of a surrogate anti-mouse IL-6 mAb on disease development has been evaluated in a CIA model. The results indicate that i.p. administration of anti-mouse IL-6 at 1 mg/mouse/week prior to disease induction significantly suppressed the development of collagen-induced arthritis as reflected by the marked reduction in disease severity. Arthritis was induced in 8-week old DBA/1 LacJ mice with 100 µg of bovine type II collagen in Freund's complete adjuvant (FCA) intradermally at the base of the tail. Mice were clinically monitored daily for the onset of disease. Anti-IL-6 mAb or isotype control mAb was administered i.p. 2 days prior to CIA induction and weekly thereafter at 1 mg/mouse. The arthritis score was determined based on swelling, erythema, and disfiguration of the joint.

The histopathological data confirmed the clinical observation that weekly i.p. injection of anti-mouse IL-6 mAb significantly improved the parameters of collagen induced arthritis. All of the parameters of arthritis examined including the inflammatory response (synovitis and pannus formation) and the erosive changes (erosions and overall joint architecture) were significantly improved in anti-mouse IL-6 treated mice as compared with control mAb-treated animals. The anti-IL-6 mAb suppressed arthritis at a histopathological level. Synovitis was scored based on the thickness of the synovial membrane; pannus formation was scored based on the extent of pannus relative to joint space; and erosions were scored based on the extent into the cartilage and subchondral bone.

The loss of cartilage matrix proteins was significantly reduced in mice treated with anti-mouse IL-6 mAb. Representative joint sections obtained from control and anti-IL-6 mAb treated animals at the end of the study (day 53) were examined by Toluidine Blue staining for cartilage matrix.

Micro-CT analysis supported the clinical observation that the effect of anti-mouse IL-6 therapy was exerted at the level of the progression of disease within the individual joint. Visual inspection of typical 3D CT images indicates the marked degree of erosive changes that occur in the isotype control mAb-treated group as compared with the predominantly mild soft tissue inflammatory changes in joints from anti-mouse IL-6 treated animals. The experiments were performed with representative animals treated with control mAb and anti-mouse IL-6 mAb treated animals.

Lupus. Effect of Anti-IL-6 in NZB/W F1 Mice

Pre-Clinical In Vivo Disease Models

Murine models exist for SLE and these have close similarities to human disease. Studies of MRL/lpr and NZB/W F1 strains demonstrated B cell hyperproliferation, autoantibody production, and immune complex deposition that closely resemble the human disease. Anti-IL-6 mAb was shown to be effective in inhibiting autoantibody production, reducing proteinuria, and improving animal survival in NZB/W F1 mice.

Figure 7:
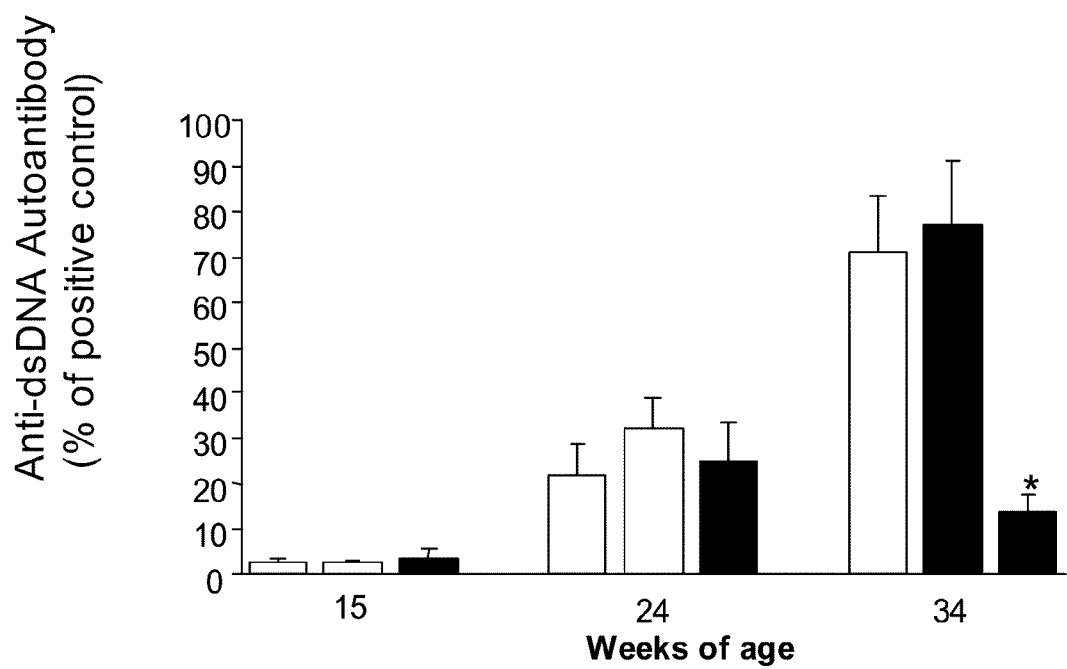
FIG. 7 shows the inhibition of anti-dsDNA autoantibody production by anti-IL-6 mAb in NZB/W F1 mice.

The effect of a surrogate anti-mouse IL-6 mAb on lupus disease development has been evaluated in NZB/W F1 mice. The preliminary results demonstrated that i.p. administration of anti-mouse IL-6 mAb at 1 mg/mouse/week for 22 weeks suppressed the production of anti-dsDNA autoantibody, a major pathogenic autoantibody in this disease model (FIG. 7). Anti-dsDNA autoantibody levels in anti-IL-6 mAb treated animals were consistently lower throughout the study as compared to that in saline and control Ab treated animals.

As discussed above, FIG. 7 shows the inhibition of anti-dsDNA autoantibody production by anti-IL-6 mAb in NZB/W F1 mice. An Individual O.D. value for each sample was normalized to a positive control serum and presented as % positive control. Each point represents the % positive control of each sample and the line represents the mean of all the data points in each group. Significant difference is indicated as *p<0.01.

In addition, anti-IL-6 mAb inhibited B-cell proliferation and reduced kidney damage when a small subset of the animals was examined. While there was no significant difference in T cell proliferation among the different treatment groups at the end of the study, B-cell proliferation induced by anti-IgM and anti-CD40 was lower in anti-IL-6 mAb treated mice compared with that of saline-treated mice over time, specifically, after 34 weeks. This result is consistent with the reduced anti-dsDNA autoantibody production reported above and suggests that autoreactive B cells might be the direct and dominant targets for anti-IL-6 mAb treatment.

Histopathological analysis indicated that animals in the study could be categorized into 3 kidney disease severity groups (mild, moderate, and severe) (Table 9). The renal disease pathology in NZB/W F1 mice indicate mixed lymphoid hyperplasia and immune complex deposition in the glomerular basement membrane.

Animals treated with anti-IL-6 mAb developed less severe kidney disease. Perivascular mixed lymphoid hyperplasia and protein deposition were absent in the anti-IL-6 mAb treated animals while animals treated with saline and control Ab developed moderate and severe perivascular mixed lymphoid hyperplasia and protein deposition. Furthermore, immune complex deposition in the glomerular basement membrane was mild in the anti-IL-6 mAb treated animals as compared with that in the other two treatment groups. Further dissection of the mechanism of action of anti-IL-6 mAb on B, T, and macrophage cell functions is performed as these cells play critical roles in the pathogenesis of SLE.

Type II Diabetes Mellitus

IL-6 has been indicated to play an important role in development of insulin resistance associated with obesity. However, in vitro and in vivo data generated to date both support and oppose its potential role in insulin resistance.

In Vitro Experiments

Experiments have been performed to better understand the effects that IL-6 may have on insulin signaling and on the biological effects and function of insulin, such as glucose up-take, gene regulation, and related mechanisms using in vitro models of insulin responsive tissues (3T3 L1 cells for adipose tissue, HepG2 cells for hepatic cells, C2C12 cells for skeletal muscle) and in vivo models of insulin resistance and T2DM, such as db/db mice.

The in vitro data suggest that IL-6 exerts its primary effect on insulin signaling in the liver. IL-6 treatment of HepG2 cells leads to the inhibition of insulin induced Akt phosphorylation. This inhibitory effect of IL-6 on insulin signaling is blocked by an anti-IL-6 antibody. Changes in glucose metabolism and insulin effects in the liver have been suggested to be driving causes of the development of insulin resistance and T2D. The effects of IL-6 on insulin signaling in 3T3 L1 cells (adipocyte cell line) and C2C12 (skeletal muscle cell line) are examined to determine mechanisms of IL-6 in T2D.

3T3 L1. Experiments were conducted using 3T3 L1 mouse adipocyte cell line. In 90% differentiated 3T3 L1 cells, the effect of IL-6 on insulin induced glucose uptake was evaluated. In these experiments, treatment with 10 ng/ml of TNFα for 24 hours consistently inhibits insulin induced glucose uptake while 20 ng/ml of IL-6 did not have any effect. These data suggest that IL-6 activity on adipose tissue is not the primary mechanism of IL-6 mediated insulin resistance, but rather adipose tissue may be a main source of IL-6 that then interferes with insulin sensitivity in liver and muscle. The same data were obtained using differentiated primary human adipocytes from subcutaneous depot. The IL-6 effects on glucose uptake using human primary adipocytes from a visceral fat depot is tested because that depot could be more relevant for obesity associated insulin resistance.

HepG2. HepG2 cells were chosen as an in vitro representative of liver tissue. HepG2 cells are human hepatoma cell line where the effect of IL-6 on insulin signaling has been previously shown. In the experiments, 20 ng/ml of IL-6 blocked the insulin induced Akt phosphorylation, a crucial kinase in insulin signaling pathway, with the maximum effect being observed after 60 minutes of incubation; this is consistent with results reported in the scientific literature.

Akt phosphorylation on sub-confluent HepG2 cells in 10 cm dishes was measured after rh IL-6 (20 ng/ml) incubation for 30, 60, 90 and 120 minutes. During the last 5 minutes of incubation, 0.5 nM, 1 nM and 5 nM insulin were added to induce Akt phosphorylation. Cells were lysed using modified RIPA lysis buffer and Akt phosphorylation was measured using Ser-Phospho-Akt ELISA. Results were obtained using pAkt and Akt ELISA kits (BioSource). At 60 minutes of IL-6 treatment, in the presence of a physiological concentration of insulin (0.5-1 nM), Akt phosphorylation was inhibited ~50% compared to the control group. Protein concentrations were quantitated with the Pierce BCA protein assay kit.

Effect of IL-6 Antibody

Figure 8A:
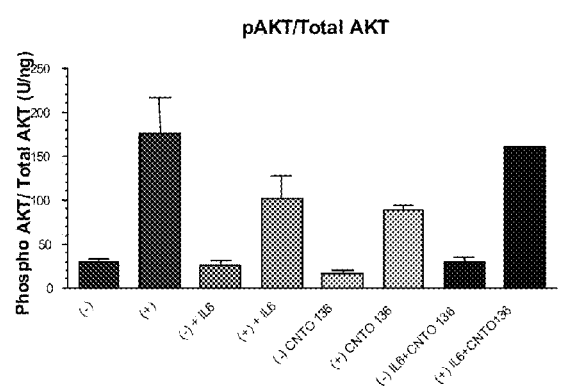
FIG. 8A shows the effect of IL-6 in the presence and absence of human engineered anti-IL-6 antibody on insulin induced Akt phosphorylation.
Figure 8B:
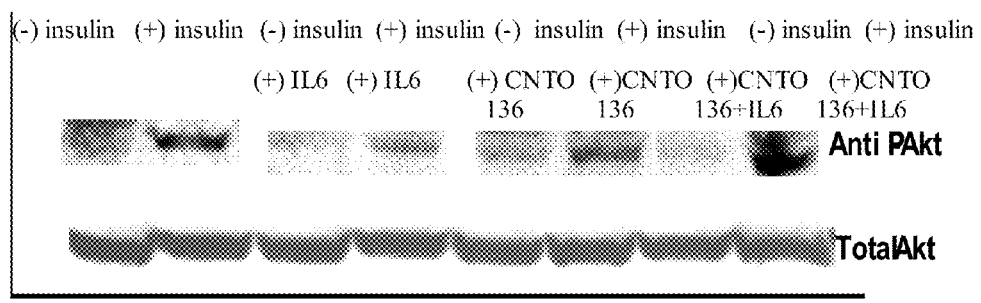
FIG. 8B shows a western blot analysis of the effect of IL-6 in the presence and absence of human engineered anti-IL-6 antibody on insulin induced Akt phosphorylation.

The ability of human engineered anti-IL-6 antibody to inhibit IL-6 effects on insulin-induced Akt-phosphorylation was measured. 20 μg/ml of human engineered anti-IL-6 antibody was able to inhibit the IL-6 effects in HepG2 cells. FIGS. 8A and 8B show the effect of IL-6 in the presence and absence of human engineered anti-IL-6 antibody on insulin induced Akt phosphorylation.

In the top image (FIG. 8A), data represent mean+/−SEM. (*Significant compared to (+) insulin, IL-6, P=0.029; **Significant compared to (+) insulin+IL-6, P=0.02). Sub-confluent HepG2 cells were treated with 20 ng/ml of IL-6 for 60 minutes. During the last 5 minutes of treatment, 1 nM insulin was added and cells were lysed using modified RIPA buffer. Samples were analyzed by ELISA that detects phosphorylation at Ser 473 of Akt. All data were normalized to total Akt measured by ELISA. AME-19a treatment was able to restore normal Akt signaling.

In the bottom image (FIG. 8B), a representative western blot is shown. Top bands include samples treated with IL-6 (20 ng/ml, 60 min, 5 min with 1 nM insulin), AME-19a (20 ug/ml+/−L-6 at 20 ng/ml for 60 minutes, 5 minutes with 1 nM insulin) or buffer. Blot was probed with anti-phospho Ser/Akt antibody (upper panel) (pS473, Biosource). The lower bands (the same blot was stripped and reprobed with anti-Akt from BioSource) demonstrate that equivalent protein was loaded per lane.

Method: HEPG2 cells were grown in 100 mm tissue culture dishes until confluency. Cells were starved overnight in DMEM-1% BSA. AME-19a (20 ug/ml) was incubated on cells for ~30 minutes prior to IL-6 addition. IL-6 (20 ng/ml)+/−AME-19a (20 ug/ml) were incubated for ~30 minutes prior to addition to cells. Samples were incubated on cells for 60 minutes, at 37° C.; then 1 nM insulin (final concentration) was added to cells for 5 minutes, at room temperature. Cells were washed immediately with 3 rinses of ice cold PBS. Plates were frozen until lysis. Phospho Akt and total Akt were determined using ELISA kits (BioSource and Sigma). Reference: J J Senn, P J Kover, I A Nowak and R A Mooney. Interleukin 6 induces cellular insulin resistance in hepatocytes. *Diabetes*. 51:3391-3399, 2002.

Primary Rat Hepatocytes

Figure 11A:
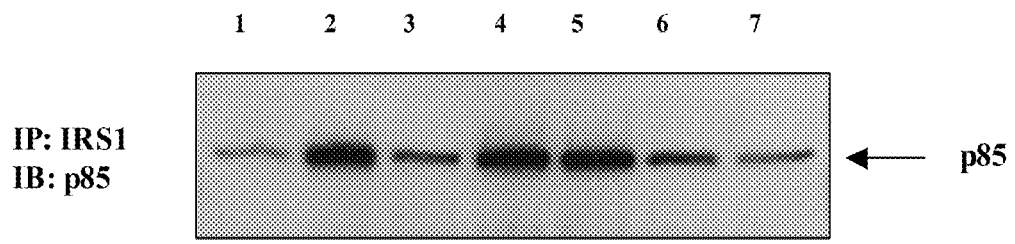
FIG. 11A shows PI3 kinase activation in rat hepatocytes treated with insulin, IL-6 protein, and anti-IL-6 antibody.
Figure 12A:
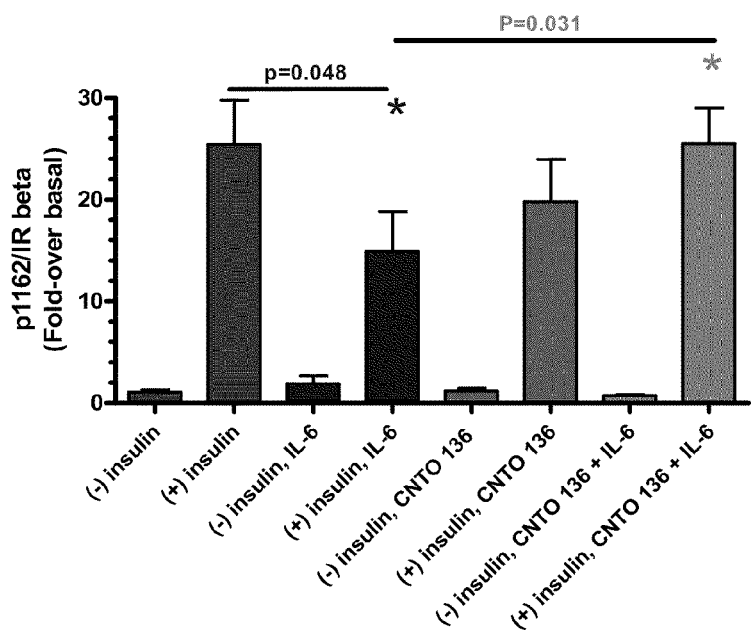
FIG. 12A shows the effect of IL-6 on signaling in rat hepatocytes with respect to the insulin-induced phosphorylation of IR.
Figure 12B:
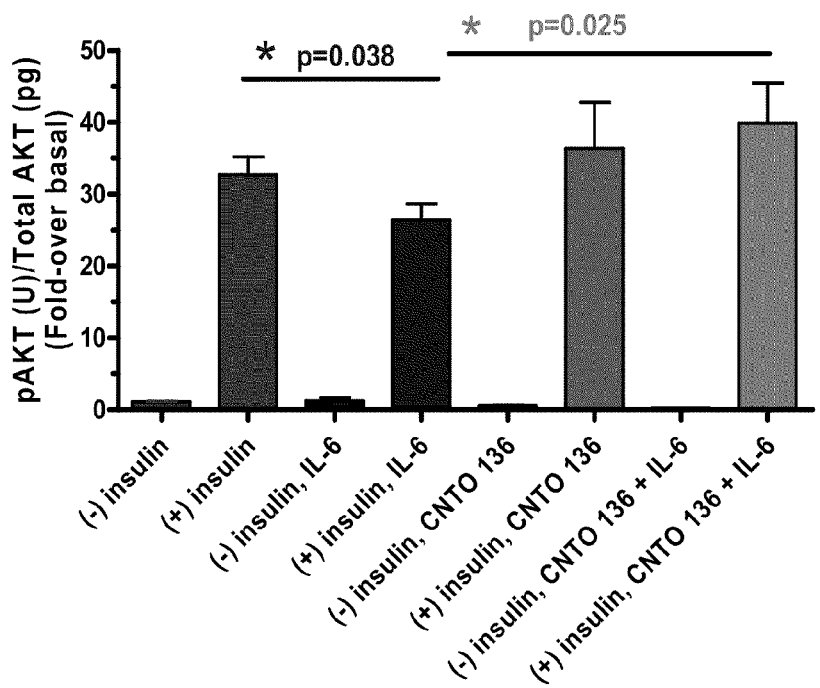
FIG. 12B shows the effect of IL-6 on signaling in rat hepatocytes with respect to the insulin-induced phosphorylation of Akt.

Primary hepatocytes represent a more relevant in vitro system suitable for testing the effect of IL-6 and anti-IL-6 antibodies (or other IL-6 antagonists) on insulin signaling and the insulin effect on liver glucose production. To determine PI3 kinase (PI3K) activation in rat hepatocytes treated by insulin, IL-6 and/or IL-6 mAb, isolated cells were treated with insulin in the presence and absence of 5 ng/ml IL-6, and the phosphorylation of the insulin receptor, IRS-1 (FIG. 12A), and Akt (FIG. 12B) was determined using ELISA assays and Western blot analysis. In addition, the effects of IL-6 on insulin stimulated IRS1/p85 association were examined (FIGS. 11A and B). The experiments were performed as follows:

Primary rat hepatocytes (~2 months old) in 6 well collagen coated plates were equilibrated overnight in Hepatoczyme media. On the next day, cells were starved for 6 hours in DMEM-1% BSA-penn strep; then incubated with hIL-6 (5 ng/ml); anti-IL-6 antibody (AME-19a) (20 ng/ml) or anti-IL-6 antibody (AME-19a)+hIL-6 for 90 minutes at 37° C. Cells were pretreated for 1 hour with anti-IL-6 antibody (AME-19a) prior to addition of the combination. The combination was also preincubated prior to addition to the cells. 5 nM of insulin (from BioSource) was added to cells for 5 minutes; then cells were aspirated and lysed immediately with BioSource extraction buffer+protease inhibitors. Lysates were centrifuged and the supernatants were diluted 1:10 and tested in ELISAs (from Biosource).

IRS1/p85 Association:

Equal amounts of protein (45 μg) were incubated overnight with 2 μg of anti-IRS-1 polyclonal antibody (from Upstate, Item #06-248). The samples were than immunoprecipitated with protein A beads for 1 hour and eluted with 3× sample buffer for SDS-PAGE. The IP samples were than run on 4-12% SDS-Page gel and then transferred to membrane for Western blot analysis. The membranes were probed with: (1) 1:100 diluted p85 mAb (from Upstate, Item #05-217) for IRS-1 associated p85, i.e., the active PI3K (as shown in FIG.

Figure 11B:
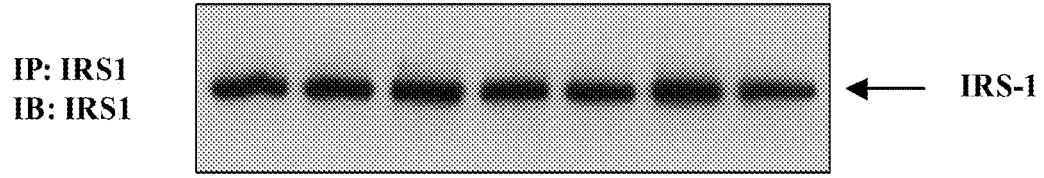
FIG. 11B shows the control for the study of PI3 kinase activation in rat hepatocytes.

11A); and (2) 1:600 diluted IRS-1 mAb (from BD Biosciences, Item #611395) for total IRS-1 as a loading control (as shown in FIG. 11B).

The data indicate that IL-6 treatment leads to a decrease of insulin-induced phosphorylation of IR, IRS-1 and Akt. This effect of IL-6 was abolished when cells were pretreated with anti-IL-6 antibody (clone AME-19a). In addition, IL-6 inhibited insulin induced p85 (subunits of PI3K) association with IRS-1. Again, this effect of IL-6 was inhibited by pretreatment with anti-IL-6 antibody.

In Vivo Experiments

The effects of IL-6 on insulin sensitivity have not been extensively tested in animals. In order to evaluate whether anti-IL-6 therapy would improve insulin sensitivity and T2DM, db/db mice and C57/B16 males on a high fat diet have been treated with commercial anti-mouse IL-6 antibody (obtained from R&D Systems).

db/db Mice

The effects of anti IL-6 treatment are tested using db/db mice of different ages. Mice between 8-10 weeks of age are characterized by hyperinsulinemia and insulin resistance, thus representing earlier stages of the disease, while mice 12-14 weeks of age are characterized by elevated glucose levels in addition to hyperinsulinemia, thus representing advanced stages of T2DM. Both age groups of mice are used to test the ability of anti IL-6 therapy to improve insulin sensitivity and glycemic control in intraperitoneal glucose tolerance test (ipGTT).

Figure 15:
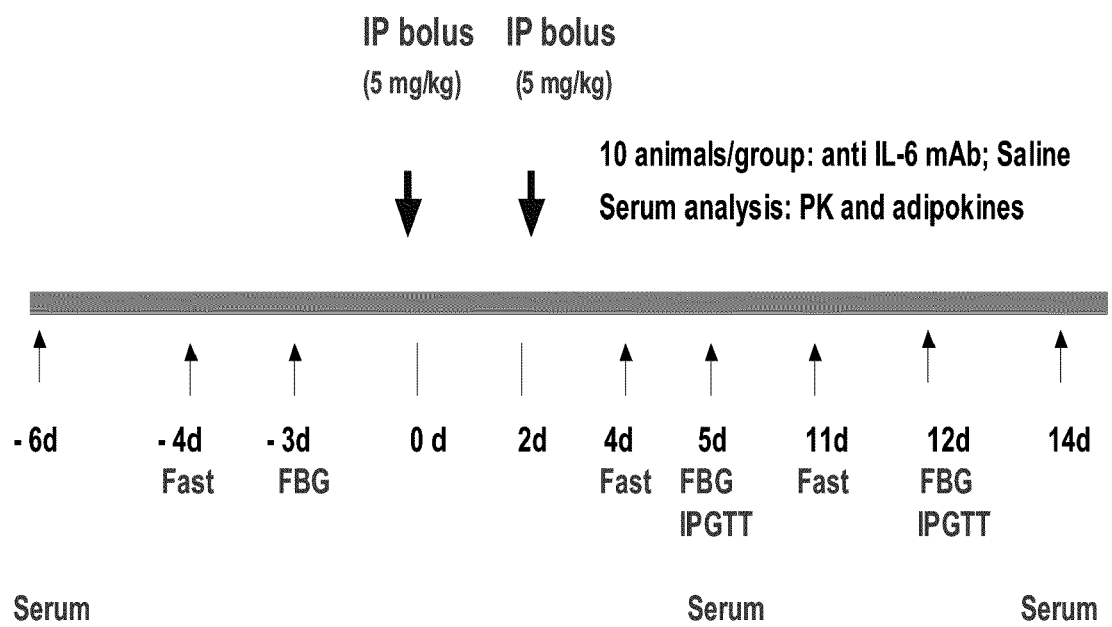
FIG. 15 shows the treatment schedule of mice with anti IL-6 mAb for an intraperitoneal glucose tolerance test (ipGTT).

The db/db mice have non-functional leptin signaling due to the mutation within the leptin receptor. These mice develop obesity, hyperinsulinemia and insulin resistance as the mice age, with the first symptoms being detected when the mice are 6-8 weeks old. Two groups of mice of different ages—8 and 12 weeks old—have been treated with 5 mg/kg of anti IL-6 mAb and an intraperitoneal glucose tolerance test (ipGTT) was performed one day and 7 days post treatment. The treatment schedule is shown in FIG. 15.

In 8-week old animals, treatment with anti IL-6 mAb did not have an effect on glucose clearance during GTT. Anti IL-6 mAb treatment lead to improvement in glucose tolerance (GT) in 12 week old animals, although the effect was not statistically significant (p=0.063). This improvement in GTT was seen at day 7 post treatment. In addition, serum samples before and after the completion of the study were analyzed for their adipokine and adiponectin profiles. The levels of IL-6, TNFα and MCP-1 were below the detection levels. This data taken together with results from ipGTT may suggest that: db/db animals are not a good model to study anti IL-6 effects on insulin resistance; and tissue levels of IL-6 are more relevant for a possible role that IL-6 may play in development of insulin resistance and T2DM.

Diet Induced Obesity (DIO)—Animal Model for Obesity and Insulin Resistance

C57/B1 male mice were fed a diet comprising 60% fat for 20-35 weeks. They developed obesity (average body weight was 50.5 grams) and an increase in fasting blood glucose levels (FBG>145 mg/dl). In addition, they have impaired GT. DIO animals were treated with 10 mg/kg of murine anti IL-6 Ab (R&D Systems). Overall, they received 50 mg/kg of anti IL-6 mAb over the period of 3 weeks. ipGTT was performed after the first 2 doses (day 5), after the 4th dose (days 12 and 16) and after the 5th dose (day 23). At the same time, blood was obtained for measurements of adipocytokines and adiponectin.

Anti IL-6 treatment did not improve glucose tolerance at days 5 and 12; however, when performed at days 16 and 23, an improvement in glucose clearance as well as in levels of glucose excursion were observed. This improvement reached statistical significance at 39, 60 and 90 minutes during GTT.

In another set of experiments, DIO animals were treated weekly (2 doses during the first week and 1 dose each week for the subsequent 4 weeks) with 10 and 20 mg/kg of anti IL-6 Ab and 20 mg/kg IgG isotype control via i.p route. HOMA-IR (after 2, 4 and 6 weeks of treatment), ipGTT, ipITT and adipokine profile (at 6 weeks of treatment) have been performed.

HOMA-IR Analysis on Anti-IL-6 Ab Treated DIO Animals:

In these studies, there was a decrease in fasting blood glucose and insulin levels in DIO animals treated with 10 and 20 mg/kg of murine anti-IL-6 Ab and isotype control. Animals were bleed and fasting glucose and insulin levels were determined using Trace/DMA glucose (ox) (thermo Electron Corp) and Ultra Sensitive Rat Insulin Elisa (Crystal Chem), respectively. These values were used to determine HOMA-IR. The HOMA-IR index reflects the status of insulin sensitivity and it correlates well with the finding from the clamp study. HOMA-IR is calculated by the formula: (Fasting glucose (mM) X fasting Insulin (mIU/Lit))/22.5 (FIGS. 13A, B and C).

Figure 13A:
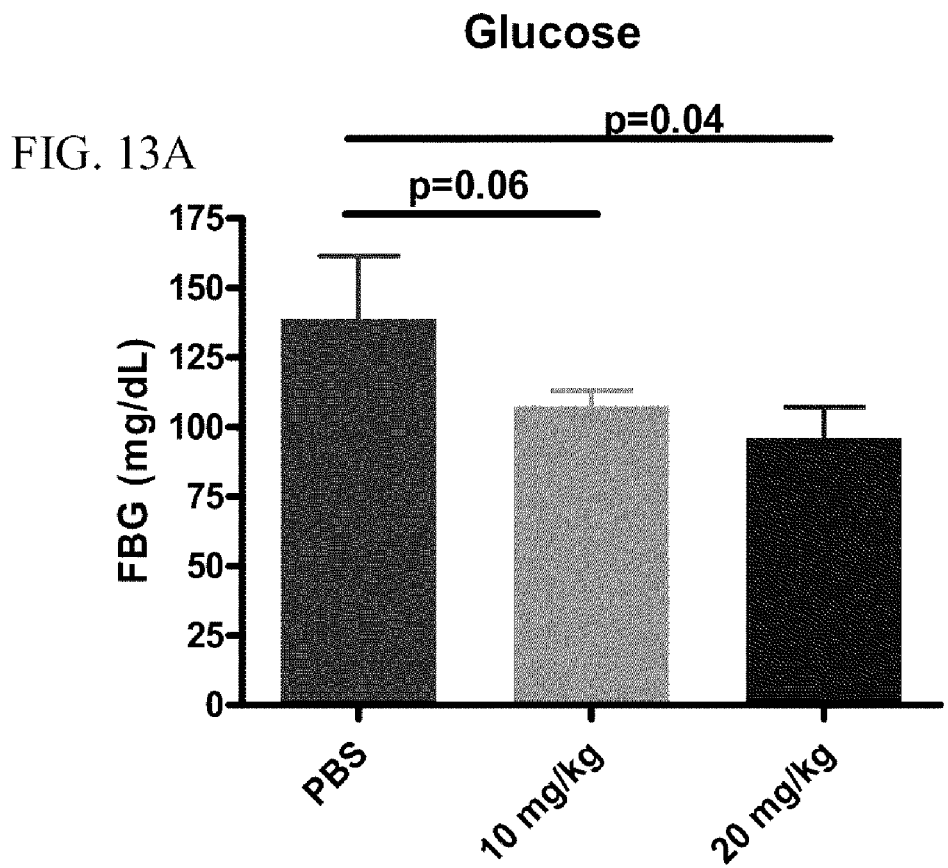
FIG. 13A shows the glucose level in DIO mice after treatment with anti-IL-6 antibody.
Figure 13B:
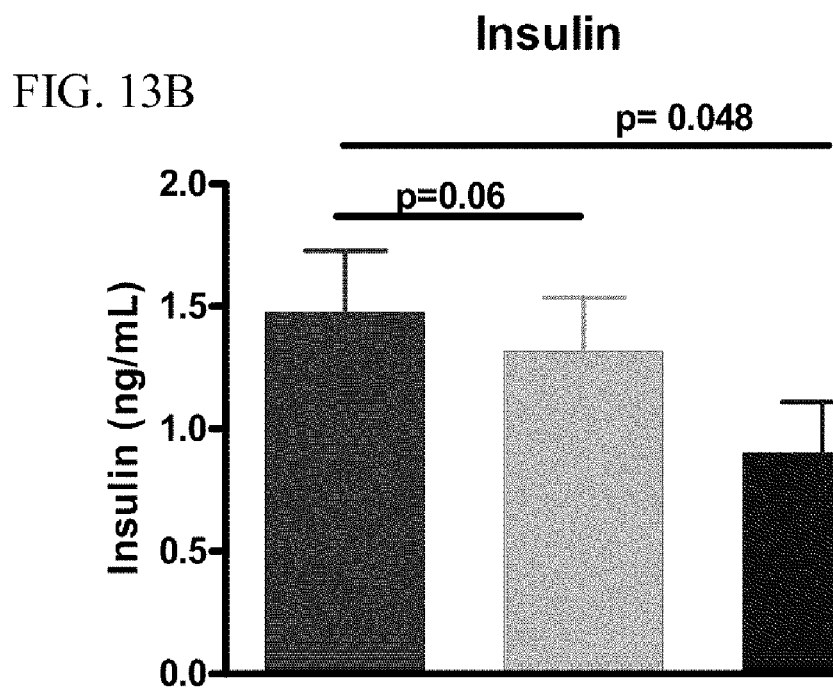
FIG. 13B shows the insulin level in DIO mice after treatment with anti-IL-6 antibody.
Figure 13C:
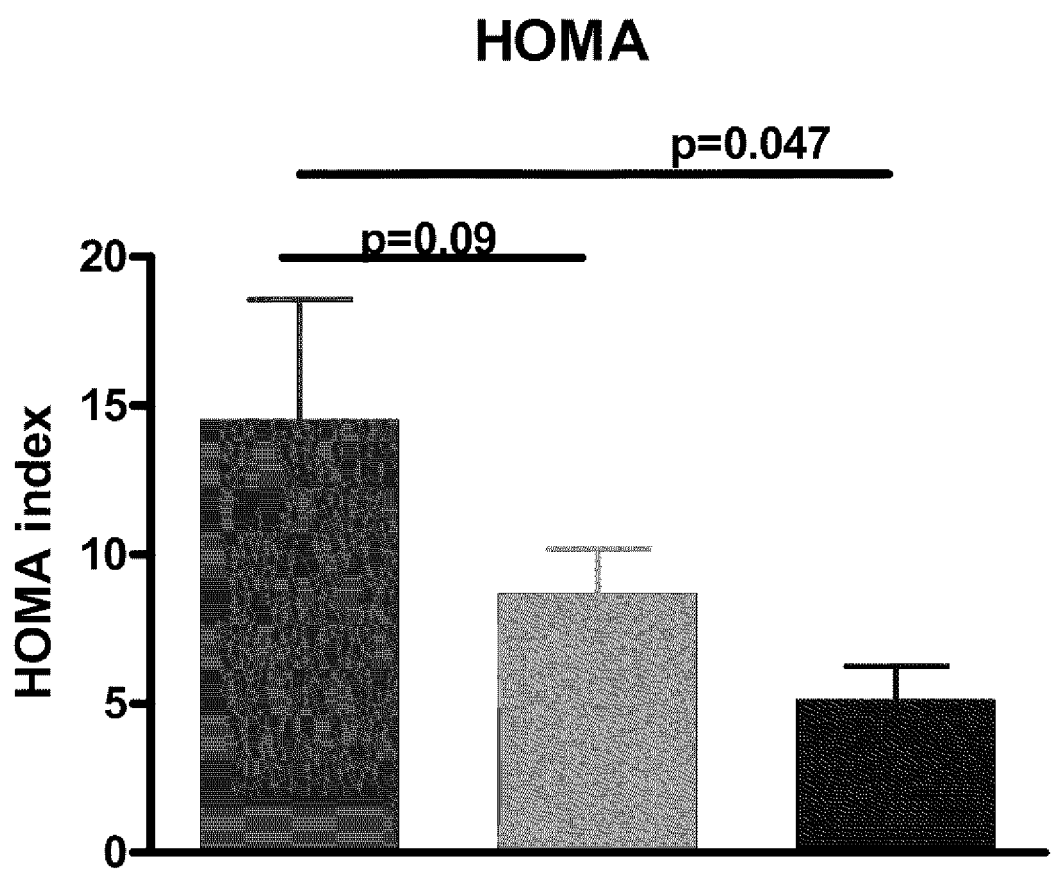
FIG. 13C shows the homeostatic model assessment (HOMA) index in DIO mice after treatment with anti-IL-6 antibody.

The improvements in HOMA-IR were observed after 2, 4 and 6 weeks of treatment (FIGS. 13A-C show the data after 6 weeks of treatment). At the end of the study, ipGTT and ipITT were performed. In both tests, anti-IL-6 treatment (20 mg/ml) significantly improved both glucose excursion and clearance when compared to isotype treated animals.

Adipokine and cytokine analysis of serum samples from control and anti-IL-6 treated animals indicated that IL-6 neutralization lead to a decrease in circulating IL-6 and TNFa levels along with the decreased trend of MCP-1 and resistin levels. In another set of data, adiponectin levels were increased with anti-IL-6 treatment.

Histological analysis of liver samples from the treatment and control groups was performed. The samples were stained with Oil Red O staining to determine the lipid content in the liver parenchyma. The liver lipid content in the DIO animals was reduced in response to treatment by the murine anti-IL-6 antibody.

Figure 14A:
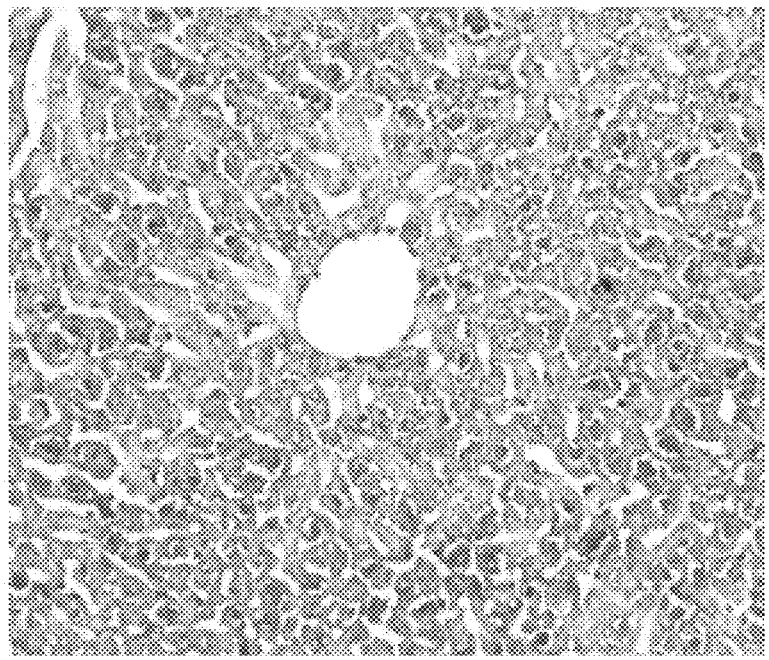
FIGS. 14A-F show the levels of lipids before and after treatment with anti-IL-6 antibody.
Figure 14B:
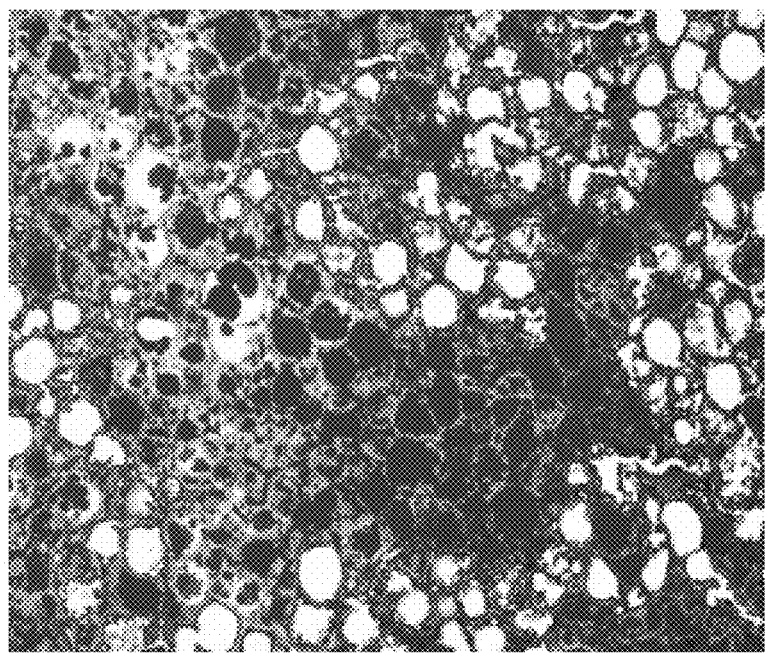
Figure 14C:
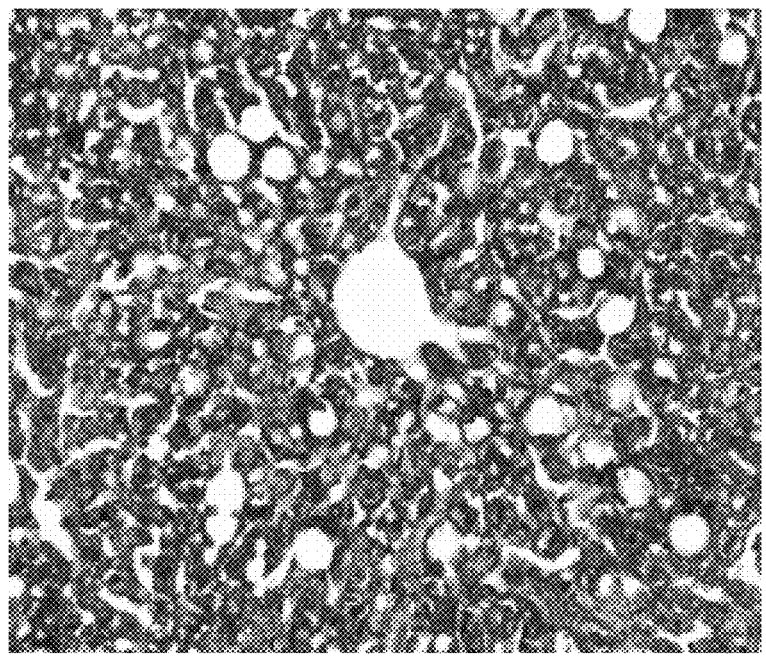
Figure 14D:
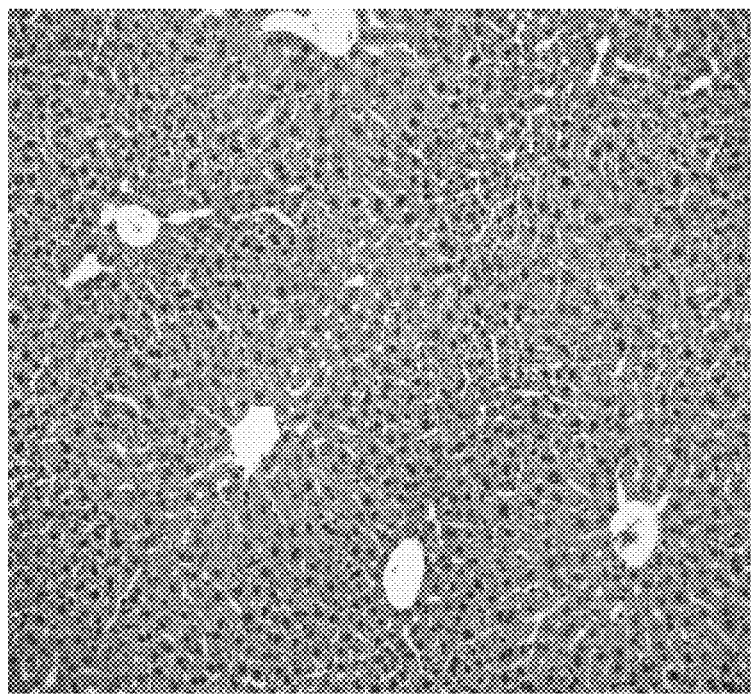
Figure 14E:
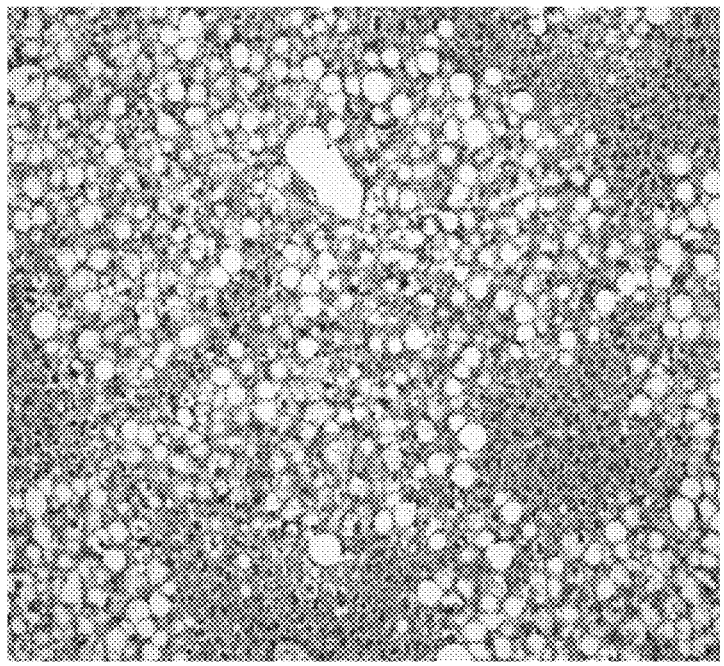
Figure 14F:
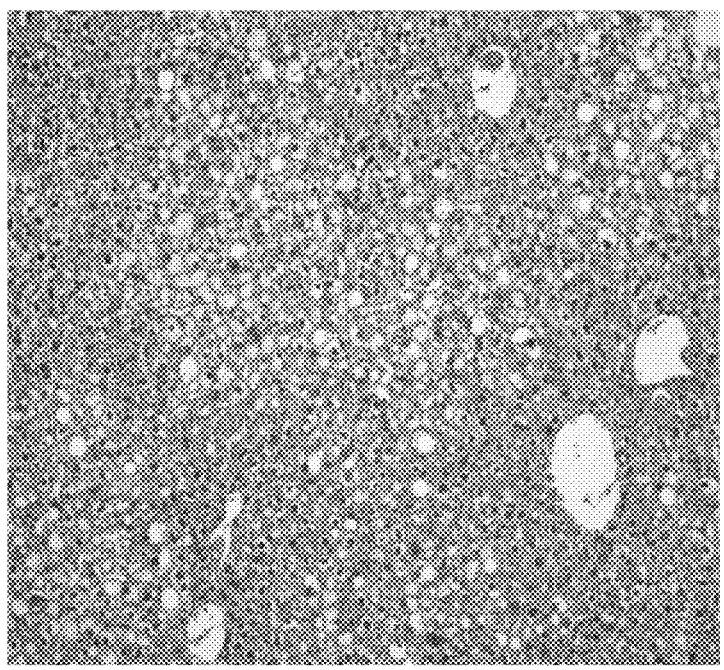

The staining reveals that 34% of vehicle treated liver sample were lipid related in untreated animals and only 8% in 20 mg/kg anti-IL-6 treated animals (FIGS. 14A-F). FIGS. 14A and D represent the control group; FIGS. 14B and E represent the untreated DIO animals; and FIGS. 14C and F represent the anti-IL-6 treated animals. The increased lipid liver content has been associated with development of insulin resistance and Type 2 Diabetes Mellitus. Thus, it is conceivable that IL-6 neutralization lead to the improvement in insulin sensitivity and T2DM by affecting liver lipid metabolism. These data taken together strongly suggest the role of IL-6 in the pathology of Type 2 Diabetes and that neutralization of IL-6 could improve insulin sensitivity.

Additional Studies

The effects of IL-6 in the presence or absence of human engineered anti-IL-6 antibody on insulin stimulated IRS1 phosphorylation, association with p85/PI3K, insulin receptor (IR) phosphorylation, glycogen syntheses, and the involvement of SOCS3 and STAT signaling in HepG2 cells are monitored. Additional experiments examine the effect of IL-6 on glucose induced insulin secretion from pancreatic islets. The data published to date describe both inhibitory as well as stimulatory effects of IL-6 on insulin secretion from rat islets. Freshly isolated rat islets (from Liefscann) are treated with IL-6 and human engineered anti-IL-6 antibody (AME-19a) in the presence or absence of glucose. Levels of insulin secreted from islets under various treatments are measured.

C2C12. C2C12 cells are used to study the effect of insulin on skeletal muscle. Experiments to examine IRS1 and Glut4 expression, insulin induced IRS 1 phosphorylation, and the effects of IL-6 on adiponectin action are performed.

Advantages:

Inhibition of IL-6 activity by the IL-6 antibody of the present invention could represent a significant therapeutic advance since it will be able to improve insulin sensitivity and metabolic control without the side effects of existing agents. In addition, current therapies do little to control systemic inflammation, which is suggested to be the underlining cause of T2DM, associated diabetic complications. A therapeutic like the IL-6 antibody of the present invention, in addition to increasing insulin sensitivity, would be expected to inhibit systemic inflammation and prevent development of diabetic complications.

The number of patients affected by T2DM is growing and it is estimated to extend to 300 million individuals by 2025. An anti IL-6 antibody could be used as a monotherapy or in combination with other already existing OAD, such as sulphonylureas, biguanides (e.g., Metphormin), thiazolidinediones, meglitinide (e.g., repaglinide), alpha-glucosidase inhibitors (e.g., acarbose). In addition, it could be used in combination with insulin or other therapeutics, such as to improve insulin sensitivity and glycemic control and avoid hypoglycemic events that are associated with insulin treatment. It is also expected that in addition to improvement of insulin sensitivity and regulation of glucose levels in T2D and Metabolic Syndrome patients, anti IL-6 therapy would have a beneficiary effect on CV changes often observed in these patients. See Saltiel, A R, and Kahn, C R. 2001. Nature 414:799-806; Hansen, B C., 1995. Diabetes Care 18:A2-A9; Diabetes Prevention Program research group. 2002. New Engl. J. Med., 346:393-403; Hansen, B C., 2000, Ann New York Academy of Science, 892:1-24; Hsueh, Wash., and Quinones, M J., 2003, Am. J. Cardiology, 93: 10J-17J; Resnick, H E and Howard, B V., 2002, Ann. Rev. Med., 53:245-267; Korner, J. and Aronne, L., 2003, J. Clin. Invest., 111(5):565-570; Skoog, T., et al., 2001. Diabetologia, 44:654:655; Fernandez-Real, J M., and Ricart W., 2003, Endocrine Reviews, 24(3):278-301; Fernandez-Real, J M., et al., 2001, J Clin Endocrinol Metab., 86:1154-1159; 10a. Fried, S., et al., 1998. J Clin Endocrinol Metab., 83:847-850; Senn, J J., et al., 2002, Diabetes, 51:3391-3399; Rotter, V., et al, 2003, JBC in press, Manus. #301977200; 12a. Stouthard, J M., et al., 1996, BBRC, 220:241-245; Southern, C., et al., 1990, Biochem J., 272:243-245; Sandler, S., et al., 1990, Endocrinology, 126:1288-1294; Pedersen, B K., et al., 2001, J. Physiol., 536:329-337; DiCosmo, B F, et al., 1994, Int. Immunol., 6:1829-1837; Wallenius, V., et al., 2002, Nature Medicine, 8:75-79; Vozarova, B., et al., 2003, Human Genetic, 112:409-413; Kubaszek, A., et al., 2003, Diabetes, 52:558-461; Tsigos, C., et al., 1997, J Clin Endocrinol Metab, 82:4167-4170; Stoutharad, J M., et al., 1995, Am J. Physiol., 268; E813-E819; Kern, Pa., et al., 2001, Am J Physiol Endocrinol Metab., 280:E745-E751; Bastard, J P., et al., 2000, J Clon Endocrinol Metab., 85:3338-3342; and Bastard, J P., et al, 2002, J. Clin. Endocrinol. Metab., 87:2084-2089.

It will be clear that the invention can be practiced otherwise than as particularly described in the foregoing description and examples. Numerous modifications and variations of the present invention are possible in light of the above teachings and, therefore, are within the scope of the appended claims.

TABLE 1

| | | Light Chain CDRs | |
|---|---|---|---|
| SEQ ID NO | CDR Name* | Clone | Sequence |
| SEQ ID NO: 1 | CDRL1 | 33 | SASHSVSYMY |
| SEQ ID NO: 2 | CDRL1 | 33 | AGTGCCAGCCATAGTGTAAGTTAC ATGTAC |
| SEQ ID NO: 3 | CDRL1 | 34 | SASISVSYMY |
| SEQ ID NO: 4 | CDRL1 | 34 | AGTGCCAGCATTAGTGTAAGTTA CATGTAC |
| SEQ ID NO: 5 | CDRL1 | 35 | SARSSVSYMY |
| SEQ ID NO: 6 | CDRL1 | 35 | AGTGCCCGGTCAAGTGTAAGTTA CATGTAC |
| SEQ ID NO: 7 | CDRL1 | 36 | SASYSVSYMY |
| SEQ ID NO: 8 | CDRL1 | 36 | AGTGCCAGCTATAGTGTAAGTTA CATGTAC |
| SEQ ID NO: 9 | CDRL1 | 37 | SASSSVFYMY |
| SEQ ID NO: 10 | CDRL1 | 37 | AGTGCCAGCTCAAGTGTATTTTA CATGTAC |
| SEQ ID NO: 11 | CDRL1 | 39 | SGSSYVSYMY |
| SEQ ID NO: 12 | CDRL1 | 39 | AGTGGCAGCTCATATGTAAGTT ACATGTAC |
| SEQ ID NO: 13 | CDRL1 | 40 | SALSSVSYMY |
| SEQ ID NO: 14 | CDRL1 | 40 | AGTGCCCTGTCAAGTGTAAGTTA CATGTAC |
| SEQ ID NO: 15 | CDRL1 | A9 | SASSSVSYMY |
| SEQ ID NO: 16 | CDRL1 | A9 | AGTGCCAGCTCAAGTGTAAGTTA CATGTAC |
| SEQ ID NO: 17 | CDRL2 | 41 | DFSNLAS |
| SEQ ID NO: 18 | CDRL2 | 41 | GACTTTTCCAACCTGGCTTCT |
| SEQ ID NO: 19 | CDRL2 | 43 | DLSNLAS |
| SEQ ID NO: 20 | CDRL2 | 43 | GACCTGTCCAACCTGGCTTCT |
| SEQ ID NO: 21 | CDRL2 | 44 | DMSNLAS |
| SEQ ID NO: 22 | CDRL2 | 44 | GACATGTCCAACCTGGCTTCT |
| SEQ ID NO: 23 | CDRL2 | 46 | DTSNLTS |
| SEQ ID NO: 24 | CDRL2 | 46 | GACACATCCAACCTGACGTCT |
| SEQ ID NO: 25 | CDRL2 | 48 | DTSELAS |

TABLE 1-continued

Light Chain CDRs

| SEQ ID NO | CDR Name* | Clone | Sequence |
|---|---|---|---|
| SEQ ID NO: 26 | CDRL2 | 48 | GACACATCCGAGCTGGCTTCT |
| SEQ ID NO: 27 | CDRL2 | A9 | DTSNLAS |
| SEQ ID NO: 28 | CDRL2 | A9 | GACACATCCAACCTGGCTTCT |
| SEQ ID NO: 29 | CDRL3 | 49 | MQWSGYPYT |
| SEQ ID NO: 30 | CDRL3 | 49 | ATGCAGTGGAGTGGTTACCCATACACG |
| SEQ ID NO: 31 | CDRL3 | 50 | CQWSGYPYT |
| SEQ ID NO: 32 | CDRL3 | 50 | TGTCAGTGGAGTGGTTACCCATACACG |
| SEQ ID NO: 33 | CDRL3 | 52 | SCWSGYPYT |
| SEQ ID NO: 34 | CDRL3 | 52 | TCTGTGTGGAGTGGTTACCCATACACG |
| SEQ ID NO: 35 | CDRL3 | A9 | SQWSGYPYT |
| SEQ ID NO: 36 | CDRL3 | A9 | TCTCAGTGGAGTGGTTACCCATACACG |
| SEQ ID NO: 138 | CDRL3 | Alt. | QQWSGYPYT |

*CDRs were as defined by Kabat with the exception of CDRH1 which is the sum of Kabat and Chothia definitions.

TABLE 2

Heavy Chain CDRs

| SEQ ID NO | CDR Name* | Clone | Sequence |
|---|---|---|---|
| SEQ ID NO: 37 | CDRH1 | 4 | GFTFSSFALS |
| SEQ ID NO: 38 | CDRH1 | 4 | GGATTCACCTTTAGTAGCTTTGCCCTTTCT |
| SEQ ID NO: 39 | CDRH1 | 5 | GFTFSPFAMS |
| SEQ ID NO: 40 | CDRH1 | 5 | GGATTCACCTTTAGTCCTTTTGCCATGTCT |
| SEQ ID NO: 41 | CDRH1 | 6 | GFQFSSFAMS |
| SEQ ID NO: 42 | CDRH1 | 6 | GGATTCCAGTTTAGTAGCTTTGCCATGTCT |
| SEQ ID NO: 43 | CDRH1 | 8 | GFTTSSFAMS |
| SEQ ID NO: 44 | CDRH1 | 8 | GGATTCACCACTAGTAGCTTTGCCATGTCT |
| SEQ ID NO: 45 | CDRH1 | Q + P | GFQFSPFAMS |
| SEQ ID NO: 46 | CDRH1 | Q + P | GGATTCCAGTTTAGTCCTTTTGCCATGTCT |
| SEQ ID NO: 47 | CDRH1 | A9 | GFTFSSFAMS |
| SEQ ID NO: 48 | CDRH1 | A9 | GGATTCACCTTTAGTAGCTTTGCCATGTCT |
| SEQ ID NO: 49 | CDRH2 | 10 | KASSGGSYTYYPDTVTG |
| SEQ ID NO: 50 | CDRH2 | 10 | AAAGCGAGTAGTGGTGGGAGTTACACCTACTATCCTGACACTGTGACGGGC |
| SEQ ID NO: 51 | CDRH2 | 11 | KISSGGSYEYYPDTVTG |
| SEQ ID NO: 52 | CDRH2 | 11 | AAAATTAGTAGTGGTGGGAGTTACGAGTACTATCCTGACACTGTGACGGGC |
| SEQ ID NO: 53 | CDRH2 | 12 | KISSGGSYYYYPDTVTG |
| SEQ ID NO: 54 | CDRH2 | 12 | AAAATTAGTAGTGGTGGGAGTTACTATTACTATCCTGACACTGTGACGGGC |
| SEQ ID NO: 55 | CDRH2 | 14 | KISSGGSWTYYPDTVTG |
| SEQ ID NO: 56 | CDRH2 | 14 | AAAATTAGTAGTGGTGGGAGTTGGACCTACTATCCTGACACTGTGACGGGC |
| SEQ ID NO: 57 | CDRH2 | 16 | KISPGGSYTYYPDTVTG |

TABLE 2-continued

Heavy Chain CDRs

| SEQ ID NO | CDR Name* | Clone | Sequence |
|---|---|---|---|
| SEQ ID NO: 58 | CDRH2 | 16 | AAAATTAGTCCGGGTGGGAGTTACACCTACTATCCTGA CACTGTGACGGGC |
| SEQ ID NO: 59 | CDRH2 | P + W + S (18a, 19a) | KISPGGSWTYYSDTVTG |
| SEQ ID NO: 60 | CDRH2 | P + W + S (18a, 19a) | AAAATTAGTCCGGGTGGGAGTTGGACCTACTATTCTGA CACTGTGACGGGC |
| SEQ ID NO: 61 | CDRH2 | A9 | KISSGGSYTYYPDTVTG |
| SEQ ID NO: 62 | CDRH2 | A9 | AAAATTAGTAGTGGTGGGAGTTACACCTACTATCCTGA CACTGTGACGGGC |
| SEQ ID NO: 113 | CDRH2 | Alt. | EISSGGSYTYYPDTVTG |
| SEQ ID NO: 63 | CDRH2 | 17 | KISSGGSYTYFPDTVTG |
| SEQ ID NO: 64 | CDRH2 | 17 | AAAATTAGTAGTGGTGGGAGTTACACCTACTTTCCTGA CACTGTGACGGGC |
| SEQ ID NO: 65 | CDRH2 | 19 | KISSGGSYTYYPDTVAG |
| SEQ ID NO: 66 | CDRH2 | 19 | AAAATTAGTAGTGGTGGGAGTTACACCTACTATCCTGA CACTGTGGCTGGC |
| SEQ ID NO: 67 | CDRH2 | 20 | KISSGGSYTYYDDTVTG |
| SEQ ID NO: 68 | CDRH2 | 20 | AAAATTAGTAGTGGTGGGAGTTACACCTACTATGATGA CACTGTGACGGGC |
| SEQ ID NO: 69 | CDRH2 | 21 | KISSGGSYTYYSDTVTG |
| SEQ ID NO: 70 | CDRH2 | 21 | AAAATTAGTAGTGGTGGGAGTTACACCTACTATTCTGA CACTGTGACGGGC |
| SEQ ID NO: 71 | CDRH2 | 22 | KISSGGSYTYYPDTVTP |
| SEQ ID NO: 72 | CDRH2 | 22 | AAAATTAGTAGTGGTGGGAGTTACACCTACTATCCTGA CACTGTGACGCCG |
| SEQ ID NO: 73 | CDRH2 | 23 | KISSGGSYTYYPDTDTG |
| SEQ ID NO: 74 | CDRH2 | 23 | AAAATTAGTAGTGGTGGGAGTTACACCTACTATCCTGA CACTGATACGGGC |
| SEQ ID NO: 75 | CDRH2 | P + S (20b, 23a) | KISPGGSYTYYSDTVTG |
| SEQ ID NO: 76 | CDRH2 | P + S (20b, 23a) | AAAATTAGTCCGGGTGGGAGTTACACCTACTATTCTGA CACTGTGACGGGC |
| SEQ ID NO: 77 | CDRH2 | P + W + D (22a) | KISPGGSWTYYDDTVTG |
| SEQ ID NO: 78 | CDRH2 | P + W + D (22a) | AAAATTAGTCCGGGTGGGAGTTGGACCTACTATGATGA CACTGTGACGGGC |
| SEQ ID NO: 79 | CDRH3 | 25 | QLWGSYALDY |
| SEQ ID NO: 80 | CDRH3 | 25 | CAGTTATGGGGGTCGTATGCTCTTGACTAC |
| SEQ ID NO: 81 | CDRH3 | 26 | QLWGYYALDT |
| SEQ ID NO: 82 | CDRH3 | 26 | CAGTTATGGGGGTACTATGCTCTTGACACG |
| SEQ ID NO: 83 | CDRH3 | 29 | QLWGTYALDY |
| SEQ ID NO: 84 | CDRH3 | 29 | CAGTTATGGGGGACTTATGCTCTTGACTAC |

TABLE 2-continued

Heavy Chain CDRs

| SEQ ID NO | CDR Name* | Clone | Sequence |
|---|---|---|---|
| SEQ ID NO: 85 | CDRH3 | 30 | QLWGNYALDY |
| SEQ ID NO: 86 | CDRH3 | 30 | CAGTTATGGGGGAATTATGCTCTTGACTAC |
| SEQ ID NO: 87 | CDRH3 | 31 | QLWGYYALDF |
| SEQ ID NO: 88 | CDRH3 | 31 | CAGTTATGGGGTACTATGCTCTTGACTTT |
| SEQ ID NO: 89 | CDRH3 | 32 | QLWGYYALDI |
| SEQ ID NO: 90 | CDRH3 | 32 | CAGTTATGGGGTACTATGCTCTTGACATT |
| SEQ ID NO: 91 | CDRH3 | A9 | QLWGYYALDY |
| SEQ ID NO: 92 | CDRH3 | A9 | CAGTTATGGGGTACTATGCTCTTGACTAC |
| SEQ ID NO: 114 | CDRH3 | Alt. | GLWGYYALDY |

*CDRs were as defined by Kabat with the exception of CDRH1 which is the sum of Kabat and Chothia definitions.

TABLE 3

Mutations from Individual CDR libraries

| Clone | CDRH1 |
|---|---|
| 4 | M34L |
| 5 | S31P |
| 6 | T28Q |
| 8 | F29T |

| Clone | CDRH2 |
|---|---|
| 10 | I51A |
| 11 | T57E |
| 12 | T57Y |
| 14 | Y56W |
| 16 | S52aP |
| 17 | Y59F |
| 19 | T64A |
| 20 | P60D |
| 21 | P60S |
| 22 | G65P |
| 23 | V63D |

| Clone | CDRH3 |
|---|---|
| 25 | Y99S |
| 26 | Y102T |
| 27 | Y99S |
| 29 | Y99T |
| 30 | Y99N |
| 31 | Y102F |
| 32 | Y102I |

| Clone | CDRL1 |
|---|---|
| 33 | S27H |
| 34 | S27I |
| 35 | S26R |
| 36 | S27Y |
| 37 | S30F |
| 38 | S27I |
| 39 | A25G, S28Y |
| 40 | S26L |

| Clone | CDRL2 |
|---|---|
| 41 | T51F |
| 43 | T51L |
| 44 | T51M |
| 46 | A55T |
| 47 | T51L |
| 48 | N53E |

| Clone | CDRL3 |
|---|---|
| 49 | Q89M |
| 50 | Q89C |
| 52 | Q90C |

TABLE 4

Mutations Included in the Combinatorial Library

| CDRH1 | CDRH2 | CDRH3 | CDRL1 | CDRL2 | CDRL3 |
|---|---|---|---|---|---|
| T28Q | S52aP | Y102F | S27I | T51F | Q89M |
| S31P | Y56W | Y102I | S27Y | T51M | |
| | P60S | | | | |
| | V63D | | | | |

TABLE 5A

Positive Library Clones

| | Light | | | Heavy | | | | | | | |
|---|---|---|---|---|---|---|---|---|---|---|---|
| CDR--> | L1 | L2 | L3 | H1 | H2 | | | | | | H3 |
| WT--> CNTO328 | S | T | Q | T | S | E | S | Y | P | V | G | Y |
| Clone | 27 | 51 | 89 | 28 | 31 | 50 | 52a | 56 | 60 | 63 | 95 | 102 |
| AME-A9 | | | | | | S | | K | | | Q | |
| AME-16 | | | | | | S | | K | P | | Q | |
| AME-18a | | F | M | Q | | P | K | P | W | S | Q | I |
| AME-19a | I | M | M | | | P | K | P | W | S | Q | I |
| AME-20b | I | M | M | Q | | | K | P | | S | Q | I |
| AME-22a | Y | F | M | Q | | P | K | P | W | D | Q | F |
| AME-23a | Y | M | M | Q | | | K | P | | S | Q | F |

TABLE 5B

Human Engineered Anti-IL-6 Antibody Clones and Corresponding CDRs

| | CDR | | | | | |
|---|---|---|---|---|---|---|
| | L1 | L2 | L3 | H1 | H2 | H3 |
| AME-A9 | SEQ ID: 15 | SEQ ID: 27 | SEQ ID: 35 | SEQ ID: 47 | SEQ ID: 61 | SEQ ID: 91 |
| AME-16 | SEQ ID: 15 | SEQ ID: 27 | SEQ ID: 35 | SEQ ID: 47 | SEQ ID: 57 | SEQ ID: 91 |
| AME-18a | SEQ ID: 15 | SEQ ID: 17 | SEQ ID: 29 | SEQ ID: 45 | SEQ ID: 59 | SEQ ID: 89 |
| AME-19a | SEQ ID: 3 | SEQ ID: 21 | SEQ ID: 29 | SEQ ID: 39 | SEQ ID: 59 | SEQ ID: 89 |
| AME-20b | SEQ ID: 3 | SEQ ID: 21 | SEQ ID: 29 | SEQ ID: 41 | SEQ ID: 75 | SEQ ID: 89 |
| AME-22a | SEQ ID: 7 | SEQ ID: 17 | SEQ ID: 29 | SEQ ID: 45 | SEQ ID: 77 | SEQ ID: 87 |
| AME-23a | SEQ ID: 7 | SEQ ID: 21 | SEQ ID: 29 | SEQ ID: 41 | SEQ ID: 75 | SEQ ID: 87 |

TABLE 6

$EC_{50}$ Values

| Clone | EC50 Value |
|---|---|
| CNTO328 | $2.7 \times 10^{-11}$M |
| AME-19a | $2.7 \times 10^{-12}$M (10-fold improvement) |

TABLE 7

Kinetic Constants for Anti-IL-6 IgG's

| Clone | Antibody Concentration (pM) | $K_D$ (pM) | Improvement Ratio (as compared to chimeric ab) | $k_{on}$ ($M^{-1}$ $sec^{-1}$) | Improvement Ratio | $k_{off}$($sec^{-1}$) (calculated) | Improvement Ratio |
|---|---|---|---|---|---|---|---|
| Chimeric antibody | 5 | 3 | 1 | $4.4 \times 10^6$ | 1 | $1.3 \times 10^{-5}$ | 1 |
| AME-16 | 1 | 0.83 | 3.6 | $1 \times 10^6$ | 0.22 | $8.3 \times 10^{-7}$ | 15.7 |
| AME-18a | 0.5 | 0.12 | 25 | $2 \times 10^7$ | 4.4 | $2.4 \times 10^{-6}$ | 5.4 |
| AME-19a | 0.5 | 0.037 | 81.1 | $5.5 \times 10^6$ | 1.2 | $2 \times 10^{-7}$ | 65 |
| AME-20b | 1 | 0.78 | 3.8 | $4.7 \times 10^6$ | 1 | $3.7 \times 10^{-6}$ | 3.5 |
| AME-22a | 1 | 0.18 | 16.7 | $6 \times 10^6$ | 1.3 | $1.1 \times 10^{-6}$ | 11.8 |
| AME-23a | 1 | 0.006 | 500 | $7.4 \times 10^6$ | 1.6 | $4.4 \times 10^{-8}$ | 295 |

TABLE 8

Cross-species reactivity of Human Engineered and Chimeric Antibody

| | Species | Inhibition (Chimeric and Human Engineered) |
|---|---|---|
| Cross-reactive | Human | + |
| | Marmoset | + |
| | Cynomolgous | + |
| | Chimp | + |
| | Rhesus | + |
| | Baboon | + |
| | Pig-Tail | + |
| | Cotton Top | + |
| Unknown | Rabbit | N/D |
| Non-reactive | Dog | − |
| | Mouse | − |
| | Rat | − |
| | Guinea Pig | − |
| | Yucatan mini-pig | − |

Cross-species reactivity of Human Engineered and Chimeric Antibody. The human engineered and chimeric antibodies are able to neutralize the proliferation of 7TD1 cells that were stimulated by conditioned supernatants from PBMCs of human, marmoset, cynomolgus monkey, chimpanzee, rhesus monkey, baboon, pigtail monkey, and cotton top monkeys. "+" positive in neutralization assay; "−" negative in neutralization assay; N/D, not determined.

TABLE 9

Impact of anti-IL-6 mAb treatment on renal pathology in NZB/W F1 mice

| Treatment group | Severe* | Moderate* | Mild* |
|---|---|---|---|
| Saline (n = 10) | 60% or 6/10 | 20% or 2/10 | 20% or 2/10 |
| Rat IgG (n = 10) | 70% or 7/10 | 30% or 3/10 | 0 or 0/10 |
| R&D anti-mouse IL-6 (n = 10) | 10% or 1/10 | 30% or 3/10 | 60% or 6/10 |

*Severe - Perivascular mixed lymphoid hyperplasia, mesangial hypercellularity, protein deposition, glomeruler basement membrane immune complex deposition
Moderate - Moderate perivascular mixed lymphoid hyperplasia, moderate mesangial hypercellularity, glomeruler basement membrane immune complex deposition, no protein deposition
Mild - Mild mesangial hypercellularity, mild glomeruler basement membrane immune complex deposition, no perivascular mixed lymphoid hyperplasia, no protein deposition

TABLE 10

Variable region sequences of clones

| SEQ ID NO | Clone | Heavy (H) or Light (L) Chain V Region | Sequence |
|---|---|---|---|
| 93 | A9 | L Chain AA | EIVLTQSPATLSLSPGERATLSCSASSSVS YMYWYQQKPGQAPRLLIYDTSNLASGIPAR FSGSGSGTDFTLTISSLEPEDFAVYYCSQW SGYPYTFGGGTKVEIK |
| 94 |  | L Chain Nucleotide | GAAATTGTGTTGACACAGTCTCCAGCCACCCTGTCTTTGTCTCCAGGGGA AAGAGCCACCCTCTCCTGCAGTGCCAGCTCAAGTGTAAGTTACATGTACT GGTACCAACAGAAACCTGGCCAGGCTCCCAGGCTCCTCATCTATGACACA TCCAACCTGGCTTCTGGCATCCCAGCCAGGTTCAGTGGCAGTGGGTCTGG GACAGACTTCACTCTCACCATCAGCAGCCTAGAGCCTGAAGATTTTGCAG TTTATTACTGTTCTCAGTGGAGTGGTTACCCATACACGTTCGGCGGAGGG ACCAAGGTGGAGATCAAA |
| 95 |  | H Chain AA | EVQLVESGGGLVQPGGSLRLSCAASGFTFS SFAMSWVRQAPGKGLEWVAKISSGGSYTYY PDTVTGRFTISRDNAKNSLYLQMNSLRAED TAVYYCARQLWGYYALDYWGQGTTVTSS |
| 96 |  | H Chain Nucleotie | GAGGTGCAGCTGGTGGAGTCTGGGGGAGGCTTGGTCCAGCCTGGGGGGTC CCTGAGACTCTCCTGTGCAGCCTCTGGATTCACCTTTAGTAGCTTTGCCA TGTCTTGGGTCCGCCAGGCTCCAGGGAAGGGGCTGGAGTGGGTGGCCAAA ATTAGTAGTGGTGGGAGTTACACCTACTATCCTGACACTGTGACGGGCCG ATTCACCATCTCCAGAGACAACGCCAAGAACTCACTGTATCTGCAAATGA ACAGCCTGAGAGCCGAGGACACGGCTGTGTATTACTGTGCGAGACAGTTA TGGGGGTACTATGCTCTTGACTACTGGGGCCAAGGGACCACGGTCACCGT CTCCTCA |
| 97 | 19A | L Chain AA | EIVLTQSPATLSLSPGERATLSCSASISVS YMYWYQQKPGQAPRLLIYDMSNLASGIPAR FSGSGSGTDFTLTISSLEPEDFAVYYCMQW SGYPYTFGGGTKVEIK |
| 98 |  | L Chain Nucleotide | GAAATTGTGTTGACACAGTCTCCAGCCACCCTGTCTTTGTCTCCAGGGGA AAGAGCCACCCTCTCCTGCAGTGCCAGCATTAGTGTAAGTTACATGTACT GGTACCAACAGAAACCTGGCCAGGCTCCCAGGCTCCTCATCTATGACATG TCCAACCTGGCTTCTGGCATCCCAGCCAGGTTCAGTGGCAGTGGGTCTGG GACAGACTTCACTCTCACCATCAGCAGCCTAGAGCCTGAAGATTTTGCAG TTTATTACTGTATGCAGTGGAGTGGTTACCCATACACGTTCGGCGGAGGG ACCAAGGTGGAGATCAAA |
| 99 |  | H Chain AA | EVQLVESGGGLVQPGGSLRLSCAASGFTFS PFAMSWVRQAPGKGLEWVAKISPGGSWTYY SDTVTGRFTISRDNAKNSLYLQMNSLRAED TAVYYCARQLWGYYALDIWGQGTTVTSS |
| 100 |  | H Chain Nucleotide | GAGGTGCAGCTGGTGGAGTCTGGGGGAGGCTTGGTCCAGCCTGGGGGGTC CCTGAGACTCTCCTGTGCAGCCTCTGGATTCACCTTTAGTCCTTTTGCCA TGTCTTGGGTCCGCCAGGCTCCAGGGAAGGGGCTGGAGTGGGTGGCCAAA ATTAGTCCGGGTGGGAGTTGGACCTACTATTCTGACACTGTGACGGGCCG ATTCACCATCTCCAGAGACAACGCCAAGAACTCACTGTATCTGCAAATGA ACAGCCTGAGAGCCGAGGACACGGCTGTGTATTACTGTGCGAGACAGTTA |

TABLE 10-continued

Variable region sequences of clones

| SEQ ID NO | Clone | Heavy (H) or Light (L) Chain V Region | Sequence |
|---|---|---|---|
| | | | TGGGGGTACTATGCTCTTGACATTTGGGGCCAAGGGACCACGGTCACCGT<br>CTCCTCA |
| 101 | 23A | L Chain AA | EIVLTQSPATLSLSPGERATLSCSASYSVS<br>YMYWYQQKPGQAPRLLIYDMSNLASGIPAR<br>FSGSGSGTDFTLTISSLEPEDFAVYYCMQW<br>SGYPYTFGGGTKVEIK |
| 102 | | L Chain Nucleotide | GAAATTGTGTTGACACAGTCTCCAGCCACCCTGTCTTTGTCTCCAGGGGA<br>AAGAGCCACCCTCTCCTGCAGTGCCAGCTATAGTGTAAGTTACATGTACT<br>GGTACCAACAGAAACCTGGCCAGGCTCCCAGGCTCCTCATCTATGACATG<br>TCCAACCTGGCTTCTGGCATCCCAGCCAGGTTCAGTGGCAGTGGGTCTGG<br>GACAGACTTCACTCTCACCATCAGCAGCCTAGAGCCTGAAGATTTTGCAG<br>TTTATTACTGTATGCAGTGGAGTGGTTACCCATACACGTTCGGCGGAGGG<br>ACCAAGGTGGAGATCAAA |
| 103 | | H Chain AA | EVQLVESGGGLVQPGGSLRLSCAASGFQFS<br>SFAMSWVRQAPGKGLEWVAKISPGGSYTYY<br>SDTVTGRFTISRDNAKNSLYLQMNSLRAED<br>TAVYYCARQLWGYYALDFWGQGTTVTVSS |
| 104 | | H Chain Nucleotie | GAGGTGCAGCTGGTGGAGTCTGGGGGAGGCTTGGTCCAGCCTGGGGGGTC<br>CCTGAGACTCTCCTGTGCAGCCTCTGGATTCCAGTTTAGTAGCTTTGCCA<br>TGTCTTGGGTCCGCCAGGCTCCAGGGAAGGGGCTGGAGTGGGTGGCCAAA<br>ATTAGTCCGGGTGGGAGTTACACCTACTATTCTGACACTGTGACGGGCCG<br>ATTCACCATCTCCAGAGACAACGCCAAGAACTCACTGTATCTGCAAATGA<br>ACAGCCTGAGAGCCGAGGACACGGCTGTGTATTACTGTGCGAGACAGTTA<br>TGGGGGTACTATGCTCTTGACTTTTGGGCCAAGGGACCACGGTCACCGT<br>CTCCTCA |
| 116 | AME-16 | L Chain AA | EIVLTQSPATLSLSPGERATLSCSASSSVS<br>YMYWYQQKPGQAPRLLIYDTSNLASGIPAR<br>FSGSGSGTDFTLTISSLEPEDFAVYYCSQW<br>SGYPYTFGGGTKVEIK |
| 117 | | L Chain Nucleotide | ATGGAAGCCCCAGCGCAGCTTCTCTTCCTCCTGCTACTCTGGCTCCCAGA<br>TACCACCGGAGAAATTGTGTTGACACAGTCTCCAGCCACCCTGTCTTTGT<br>CTCCAGGGGAAAGAGCCACCCTCTCCTGCAGTGCCAGCTCAAGTGTAAGT<br>TACATGTACTGGTACCAACAGAAACCTGGCCAGGCTCCCAGGCTCCTCAT<br>CTATGACACATCCAACCTGGCTTCTGGCATCCCAGCCAGGTTCAGTGGCA<br>GTGGGTCTGGGACAGACTTCACTCTCACCATCAGCAGCCTAGAGCCTGAA<br>GATTTTGCAGTTTATTACTGTTCTCAGTGGAGTGGTTACCCATACACGTT<br>CGGCGGAGGGACCAAGGTGGAGATCAAA |
| 118 | | H Chain AA | EVQLVESGGGLVQPGGSLRLSCAASGFTFS<br>SFAMSWVRQAPGKGLEWVAKISPGGSYTYY<br>PDTVTGRFTISRDNAKNSLYLQMNSLRAED<br>TAVYYCARQLWGYYALDYWGQGTTVTVSS |
| 119 | | H Chain Nucleotide | ATGGAGTTTGGCCTGAGCTGGGTTTTCCTTGTTGCTATTTTAGAAGGTGT<br>CCAGTGTGAGGTGCAGCTGGTGGAGTCTGGGGGAGGCTTGGTCCAGCCTG<br>GGGGGTCCCTGAGACTCTCCTGTGCAGCCTCTGGATTCACCTTTAGTAGC<br>TTTGCCATGTCTTGGGTCCGCCAGGCTCCAGGGAAGGGGCTGGAGTGGGT<br>GGCCAAAATTAGTCCCGGTGGGAGTTACACCTACTATCCTGACACTGTGA<br>CGGGCCGATTCACCATCTCCAGAGACAACGCCAAGAACTCACTGTATCTG<br>CAAATGAACAGCCTGAGAGCCGAGGACACGGCTGTGTATTACTGTGCGAG<br>ACAGTTATGGGGGTACTATGCTCTTGACTACTGGGGCCAAGGGACCACGG<br>TCACCGTCTCCTCA |
| 120 | AME-18a | L Chain AA | EIVLTQSPATLSLSPGERATLSCSASSSVS<br>YMYWYQQKPGQAPRLLIYDFSNLASGIPAR<br>FSGSGSGTDFTLTISSLEPEDFAVYYCMQW<br>SGYPYTFGGGTKVEIK |
| 121 | | L Chain Nucleotide | ATGGAAGCCCCAGCGCAGCTTCTCTTCCTCCTGCTACTCTGGCTCCCAGA<br>TACCACCGGAGAAATTGTGTTGACACAGTCTCCAGCCACCCTGTCTTTGT<br>CTCCAGGGGAAAGAGCCACCCTCTCCTGCAGTGCCAGCTCAAGTGTAAGT<br>TACATGTACTGGTACCAACAGAAACCTGGCCAGGCTCCCAGGCTCCTCAT<br>CTATGACTTCTCCAACCTGGCTTCTGGCATCCCAGCCAGGTTCAGTGGCA<br>GTGGGTCTGGGACAGACTTCACTCTCACCATCAGCAGCCTAGAGCCTGAA |

TABLE 10-continued

Variable region sequences of clones

| SEQ ID NO | Clone | Heavy (H) or Light (L) Chain V Region | Sequence |
|---|---|---|---|
| | | | GATTTTGCAGTTTATTACTGTATGCAGTGGAGTGGTTACCCATACACGTT CGGCGGAGGGACCAAGGTGGAGATCAAA |
| 122 | | H Chain AA | EVQLVESGGGLVQPGGSLRLSCAASGFQFS PFAMSWVRQAPGKGLEWVAKISPGGSWTYY SDTVTGRFTISRDNAKNSLYLQMNSLRAED TAVYYCARQLWGYYALDIWGQGTTVTSS |
| 123 | | H Chain Nucleotide | ATGGAGTTTGGCCTGAGCTGGGTTTTCCTTGTTGCTATTTTAGAAGGTGT CCAGTGTGAGGTGCAGCTGGTGGAGTCTGGGGGAGGCTTGGTCCAGCCTG GGGGGTCCCTGAGACTCTCCTGTGCAGCCTCTGGATTCCAGTTTAGTCCC TTTGCCATGTCTTGGGTCCGCCAGGCTCCAGGGAAGGGGCTGGAGTGGGT GGCCAAAATTAGTCCCGGTGGGAGTTGGACCTACTATAGCGACACTGTGA CGGGCCGATTCACCATCTCCAGAGACAACGCCAAGAACTCACTGTATCTG CAAATGAACAGCCTGAGAGCCGAGGACACGGCTGTGTATTACTGTGCGAG ACAGTTATGGGGGTACTATGCTCTTGACATTTGGGGCCAAGGGACCACGG TCACCGTCTCCTCA |
| 124 | AME-20b | L Chain AA | EIVLTQSPATLSLSPGERATLSCSASISVS YMYWYQQKPGQAPRLLIYDMSNLASGIPAR FSGSGSGTDFTLTISSLEPEDFAVYYCMQW SGYPYTFGGGTKVEIK |
| 125 | | L Chain Nucleotide | ATGGAAGCCCCAGCGCAGCTTCTCTTCCTCCTGCTACTCTGGCTCCCAGA TACCACCGGAGAAATTGTGTTGACACAGTCTCCAGCCACCCTGTCTTTGT CTCCAGGGGAAAGAGCCACCCTCTCCTGCAGTGCCAGCATTAGTGTAAGT TACATGTACTGGTACCAACAGAAACCTGGCCAGGCTCCCAGGCTCCTCAT CTATGACATGTCCAACCTGGCTTCTGGCATCCCAGCCAGGTTCAGTGGCA GTGGGTCTGGGACAGACTTCACTCTCACCATCAGCAGCCTAGAGCCTGAA GATTTTGCAGTTTATTACTGTATGCAGTGGAGTGGTTACCCATACACGTT CGGCGGAGGGACCAAGGTGGAGATCAAA |
| 126 | | H Chain AA | EVQLVESGGGLVQPGGSLRLSCAASGFQFS SFAMSWVRQAPGKGLEWVAKISPGGSYTYY SDTVTGRFTISRDNAKNSLYLQMNSLRAED TAVYYCARQLWGYYALDIWGQGTTVTSS |
| 127 | | H Chain Nucleotide | ATGGAGTTTGGCCTGAGCTGGGTTTTCCTTGTTGCTATTTTAGAAGGTGT CCAGTGTGAGGTGCAGCTGGTGGAGTCTGGGGGAGGCTTGGTCCAGCCTG GGGGGTCCCTGAGACTCTCCTGTGCAGCCTCTGGATTCCAGTTTAGTAGC TTTGCCATGTCTTGGGTCCGCCAGGCTCCAGGGAAGGGGCTGGAGTGGGT GGCCAAAATTAGTCCCGGTGGGAGTTACACCTACTATAGCGACACTGTGA CGGGCCGATTCACCATCTCCAGAGACAACGCCAAGAACTCACTGTATCTG CAAATGAACAGCCTGAGAGCCGAGGACACGGCTGTGTATTACTGTGCGAG ACAGTTATGGGGGTACTATGCTCTTGACATTTGGGGCCAAGGGACCACGG TCACCGTCTCCTCA |
| 128 | AME-22a | L Chain AA | EIVLTQSPATLSLSPGERATLSCSASYSVS YMYWYQQKPGQAPRLLIYDFSNLASGIPAR FSGSGSGTDFTLTISSLEPEDFAVYYCMQW SGYPYTFGGGTKVEIK |
| 129 | | L Chain Nucleotide | ATGGAAGCCCCAGCGCAGCTTCTCTTCCTCCTGCTACTCTGGCTCCCAGA TACCACCGGAGAAATTGTGTTGACACAGTCTCCAGCCACCCTGTCTTTGT CTCCAGGGGAAAGAGCCACCCTCTCCTGCAGTGCCAGCTACAGTGTAAGT TACATGTACTGGTACCAACAGAAACCTGGCCAGGCTCCCAGGCTCCTCAT CTATGACTTCTCCAACCTGGCTTCTGGCATCCCAGCCAGGTTCAGTGGCA GTGGGTCTGGGACAGACTTCACTCTCACCATCAGCAGCCTAGAGCCTGAA GATTTTGCAGTTTATTACTGTATGCAGTGGAGTGGTTACCCATACACGTT CGGCGGAGGGACCAAGGTGGAGATCAAA |
| 130 | | H Chain AA | EVQLVESGGGLVQPGGSLRLSCAASGFQFS PFAMSWVRQAPGKGLEWVAKISPGGSWTYY PDTDTGRFTISRDNAKNSLYLQMNSLRAED TAVYYCARQLWGYYALDFWGQGTTVTSS |
| 131 | | H Chain Nucleotide | ATGGAGTTTGGCCTGAGCTGGGTTTTCCTTGTTGCTATTTTAGAAGGTGT CCAGTGTGAGGTGCAGCTGGTGGAGTCTGGGGGAGGCTTGGTCCAGCCTG GGGGGTCCCTGAGACTCTCCTGTGCAGCCTCTGGATTCCAGTTTAGTCCC TTTGCCATGTCTTGGGTCCGCCAGGCTCCAGGGAAGGGGCTGGAGTGGGT GGCCAAAATTAGTCCCGGTGGGAGTTGGACCTACTATCCTGACACTGACA CGGGCCGATTCACCATCTCCAGAGACAACGCCAAGAACTCACTGTATCTG |

TABLE 10-continued

Variable region sequences of clones

| SEQ ID NO | Clone | Heavy (H) or Light (L) Chain V Region | Sequence |
|---|---|---|---|
| | | | CAAATGAACAGCCTGAGAGCCGAGGACACGGCTGTGTATTACTGTGCGAG ACAGTTATGGGGGTACTATGCTCTTGACTTCTGGGGCCAAGGGACCACGG TCACCGTCTCCTCA |

TABLE 11

Amino acid sequence of a human light chain framework region L6 with interspersed CDR sequences labeled (FRL1 - SEQ ID NO: 105)     CDRL1     (FRL2 - SEQ ID NO: 106) CDRL2
EIVLTQSPATLSLSPGERATLSCXXXXXXXXXXWYQQKPGQAPRLLIYXXXXXXX (FRL3 - SEQ ID NO: 107)               CDRL3     (FRL4 - SEQ ID NO: 108)
GIPARFSGSGSGTDFTLTISSLEPEDFAVYYCXXXXXXXXXFGGGTKVEIK

TABLE 12

Amino acid sequence of a human heavy chain framework region VH3-7 with interspersed CDR sequences labeled (FRH1 - SEQ ID NO: 109)     CDRH1     (FRH2 - SEQ ID NO: 110)
EVQLVESGGGLVQPGGSLRLSCAASXXXXXXXXXXWVRQAPGKGLEWVA CDRH2                    (FRH3 - SEQ ID NO: 111)
XXXXXXXXXXXXXXXXXXXRFTISRDNAKNSLYLQMNSLRAEDTAVYYCAR

CDRH3          (FRH4 - SEQ ID NO: 112)
XXXXXXXXXXWGQGTTVTVSS

TABLE 13

CDR Sequences

| SEQ ID NO: | CDR | AA Sequence* |
|---|---|---|
| 132 | CDRL1 | S$X_1$$X_2$$X_3$$X_4$V$X_5$YMY |
| 133 | CDRL2 | D$X_6$S$X_7$L$X_8$S |
| 134 | CDRL3 | $X_9$$X_{10}$WSGYPYT |
| 135 | CDRH1 | GF$X_{11}$$X_{12}$S$X_{13}$FA$X_{14}$S |
| 136 | CDRH2 | K$X_{15}$S$X_{16}$GGS$X_{17}$$X_{18}$Y$X_{19}$$X_{20}$DT$X_{21}$$X_{22}$$X_{23}$ |
| 137 | CDRH3 | QLWG$X_{24}$YALD$X_{25}$ |

*X denotes any suitable amino acid with exemplary, non-limiting amino acid substitutions shown in the sequences disclosed in SEQ ID NOS: 1-92 of Tables 1 and 2 and in Tables 3, 4, 5A, and 8. In addition, X can have the following values:
$X_1$ = A or G
$X_2$ = S or R
$X_3$ = H, I, S, or Y
$X_4$ = S or Y
$X_5$ = S or F
$X_6$ = F, L, M, or T
$X_7$ = N or E
$X_8$ = A or T
$X_9$ = M, C, or S
$X_{10}$ = Q or C
$X_{11}$ = T or Q TABLE 13-continued CDR Sequences

| SEQ ID NO: | CDR | AA Sequence* |
|---|---|---|

$X_{12}$ = F, S, or T
$X_{13}$ = S or P
$X_{14}$ = L or M
$X_{15}$ = A or I
$X_{16}$ = S or P
$X_{17}$ = Y or W
$X_{18}$ = T, E, or Y
$X_{19}$ = Y or F
$X_{20}$ = P, S, D, or F
$X_{21}$ = V or D
$X_{22}$ = T or A
$X_{23}$ = G or P
$X_{24}$ = S, Y, T, or N
$X_{25}$ = Y, T, F, or I

SEQ ID NO: 115 - AMINO ACID SEQUENCE OF IL-6 PROTEIN
MNSFSTSAFGPVAFSLGLLLVLPAAFPAPVPPGEDSKDVAAPHRQPLTS

SERIDKQIRYILDGISALRKETCNKSNMCESSKEALAENNLNLPKMAEK

DGCFQSGFNEETCLVKIITGLLEFEVYLEYLQNRFESSEEQARAVQMST

KVLIQFLQKKAKNLDAITTPDPTTNASLLTKLQAQNQWLQDMTTHLILR

SFKEFLQSSLRALRQM

What is claimed is:

1. A method for suppressing rheumatoid arthritis in an animal, comprising:
   administering a composition comprising an effective amount of an IL-6 antibody to said animal, wherein the IL-6 antibody comprises a light chain variable region amino acid sequence of SEQ ID NO:97 and a heavy chain variable region amino acid sequence of SEQ ID NO:99.

2. The method according to claim 1, wherein said effective amount is about 0.001-50 mg/kilogram of said animal.

3. The method according to claim 1, wherein said administering is by subcutaneous method.

4. The method according to 1, further comprising administering, prior, concurrently or after said administering, at least one composition comprising an effective amount of a cytokine antagonist.

5. A method for suppressing rheumatoid arthritis in an animal, comprising:
   administering a composition comprising an effective amount of an IL-6 antibody to said animal, wherein the IL-6 antibody comprises a complementarity determining region light chain 1 (CDRL1) amino acid sequence of SEQ ID NO:3, a CDRL2 amino acid sequence of SEQ ID NO:21, a CDRL3 amino acid sequence of SEQ ID NO:29, a complementarity determining region heavy chain 1 (CDRH1) amino acid sequence of SEQ ID NO:39, a CDRH2 amino acid sequence of SEQ ID NO:59, and a CDRH3 amino acid sequence of SEQ ID NO:89.

6. The method according to claim 5, wherein said effective amount is about 0.001-50 mg/kilogram of said animal.

7. The method according to claim 5, wherein said administering is by subcutaneous method.

8. The method according to claim 5, further comprising administering, prior, concurrently or after said administering, at least one composition comprising an effective amount of a cytokine antagonist.

9. A method for suppressing rheumatoid arthritis in an animal, comprising:
   administering a composition comprising an effective amount of an IL-6 antibody to said animal, wherein the IL-6 antibody comprises at least one light chain variable region and one heavy chain variable region, said light chain variable region comprising:
   a complementarity determining region light chain 1 (CDRL1) amino acid sequence of SEQ ID NO:132 comprising the sequence S-$X_1$-$X_2$-$X_3$-$X_4$-V-$X_5$-Y-M-Y, wherein $X_1$ is A or G, $X_2$ is S or R, $X_3$ is H, I, S, or Y, $X_4$ is S or Y, and $X_5$ is S or F;
   a CDRL2 amino acid sequence of SEQ ID NO:133 comprising the sequence D-$X_6$-S-$X_7$-L-$X_8$-S, wherein $X_6$ is F, L, M, or T, $X_7$ is N or E, and $X_8$ is A or T; and
   a CDRL3 amino acid sequence of SEQ ID NO:134 comprising the sequence $X_9$-$X_{10}$-W-S-G-Y-P-Y-T, wherein $X_9$ is M, C, or S, and $X_{10}$ is Q or C;
   said heavy chain variable region comprising:
   a complementarity determining region heavy chain 1 (CDRH1) amino acid sequence of SEQ ID NO:135 comprising the sequence G-F-$X_{11}$-$X_{12}$-S-$X_{13}$-F-A-$X_{14}$-S, wherein $X_{11}$ is T or Q, $X_{12}$ is F, S, or T, $X_{13}$ is S or P, and $X_{14}$ is L or M;
   a CDRH2 amino acid sequence of SEQ ID NO:136 comprising the sequence K-$X_{15}$-S-$X_{16}$-G-G-S-$X_{17}$-$X_{18}$-Y-$X_{19}$-$X_{20}$-D-T-$X_{21}$-$X_{22}$-$X_{23}$, wherein $X_{15}$ is A or I, $X_{16}$ is S or P, $X_{17}$ is Y or W, $X_{18}$ is T, E, or Y, $X_{19}$ is Y or F, $X_{20}$ is P, S, D, or F, $X_{21}$ is V or D, $X_{22}$ is T or A, and $X_{23}$ is G or P; and
   a CDRH3 amino acid sequence of SEQ ID NO:137 comprising the sequence Q-L-W-G-$X_{24}$-Y-A-L-D-$X_{25}$, wherein $X_{24}$ is S, Y, T, or N, and $X_{25}$ is Y, T, F, or I.

10. The method according to claim 9, wherein said effective amount is about 0.001-50 mg/kilogram of said animal.

11. The method according to claim 9, wherein said administering is by subcutaneous method.

12. The method according to 9, further comprising administering, prior, concurrently or after said administering, at least one composition comprising an effective amount of a cytokine antagonist.

* * * * *